(12) United States Patent
Chou et al.

(10) Patent No.: US 10,391,070 B2
(45) Date of Patent: *Aug. 27, 2019

(54) COMPOSITIONS AND METHODS FOR TREATING NEUROLOGICAL DISEASES OR INJURY

(71) Applicant: MUSC FOUNDATION FOR RESEARCH DEVELOPMENT, Charleston, SC (US)

(72) Inventors: C. James Chou, Charleston, SC (US); Sherine S. Chan, Charleston, SC (US); Jennifer J. Rahn, Charleston, SC (US); Benjamin J. Josey, Charleston, SC (US)

(73) Assignee: MUSC FOUNDATION FOR RESEARCH DEVELOPMENT, Charleston, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/833,159

(22) Filed: Dec. 6, 2017

(65) Prior Publication Data

US 2018/0185306 A1 Jul. 5, 2018

Related U.S. Application Data

(63) Continuation of application No. 14/440,155, filed as application No. PCT/US2013/069407 on Nov. 11, 2013, now Pat. No. 9,861,596.

(60) Provisional application No. 61/724,732, filed on Nov. 9, 2012.

(51) Int. Cl.
| | |
|---|---|
| A61K 31/167 | (2006.01) |
| C07C 211/45 | (2006.01) |
| A61K 31/136 | (2006.01) |
| A61K 31/137 | (2006.01) |
| A61K 31/222 | (2006.01) |
| A61K 31/352 | (2006.01) |
| A61K 31/4409 | (2006.01) |

(52) U.S. Cl.
CPC .......... *A61K 31/167* (2013.01); *A61K 31/136* (2013.01); *A61K 31/137* (2013.01); *A61K 31/222* (2013.01); *A61K 31/352* (2013.01); *A61K 31/4409* (2013.01)

(58) Field of Classification Search
None
See application file for complete search history.

(56) References Cited

U.S. PATENT DOCUMENTS 8,980,884 B2   3/2015   Puglielli

FOREIGN PATENT DOCUMENTS

| WO | WO 2004/089470 | 10/2004 |
|---|---|---|
| WO | WO 2005/053609 | 6/2005 |
| WO | WO 2010/026592 | 3/2010 |
| WO | WO 2011/113060 | 9/2011 |
| WO | WO 2012/019032 | 2/2012 |

OTHER PUBLICATIONS

Petersen, et al., Z. Krebsforsch., 72:162. (Year: 1969).*
Grundmann, et al, Z. Krebsforsch., 72:185. (Year: 1969).*
Albrecht et al., "Mechanisms of oxidative glutamate toxicity: the glutamate/cystine antiporter system $x_c^-$ as a neuroprotective drug target," CNS Neurol. Disord. Drug. Targets, 9:373-82, 2010.
Allison, "The possible role of vitamin K deficiency in the pathogenesis of Alzheimer's disease and in augmenting brain damage associated with cardiovascular disease," Med. Hypotheses, 57:151-5, 2001.
Alsdorf and Wyszynski, "Teratogenicity of sodium valproate," Expert Opin. Drug Saf., 4:345-53, 2005.
Baraban et al, "Pentylenetetrazole induced changes in zebrafish behavior, neural activity and c-fos expression," Neuroscience, 131:759-68, 2005.
Barton et al., "Pharmacological characterization of the 6 Hz psychomotor seizure model of partial epilepsy," Epilepsy Res., 47:217-227, 2001.
Beckman, et al., "The free radical theory of aging matures," Physiol. Rev., 78:547-81, 1998.
Bindoff and Engelsen, "Mitochondrial cytopathies," In: The Causes of Epilepsy, Shorvon, S. D. et al., eds., Cambridge University Press, pp. 147-157, 2011.
Bossy-Wetzel et al, "Mitochondrial fission in apoptosis, neurodegeneration and aging," Curr. Opin. Cell. Biol., 15:706-16, 2003.
Bradner et al., "Chemical phylogenetics of histone deacetylases," Nat. Chem. Biol., 6:238-243, 2010.
Butler et al., "Rational design and simple chemistry yield a superior, neuroprotective HDAC6 inhibitor, tubastatin A," Journal of the American Chemical Society, 132:10842-10846, 2010.
Chaix et al., "Chemoconvulsant-induced seizure susceptibility: toward a common genetic basis?" Epilepsia, 48(Suppl 5):48-52, 2005.
Chan et al., "Modulation of the W748S mutation in DNA polymerase {gamma} by the E1143G polymorphism in mitochondrial disorders," Hum. Mol. Genet., 15:3473-3483, 2006.
Chang and Blackstone, "Cyclic AMP-dependent protein kinase phosphorylation of Drp1 regulates its GTPase activity and mitochondrial morphology," J. Biol. Chem., 282:21583-7, 2007.
Cotticelli et al., "Primary and secondary drug screening assays for Friedreich ataxia," Journal of Biomolecular Screening, 17(3):303-313, 2012.
Davis and Maher "Protein kinase C activation inhibits glutamate-induced cytotoxicity in a neuronal cell line," Brain Res., 652:169-73, 1994.
Degterev et al., "Chemical inhibitor of nonapoptotic cell death with therapeutic potential for ischemic brain injury," Nat. Chem. Biol., 1:112-9, 2005.

(Continued)

Primary Examiner — Michael Barker
(74) Attorney, Agent, or Firm — Parker Highlander PLLC

(57) ABSTRACT

Provided are compounds for the treatment of neurological diseases or injuries, including neurodegenerative diseases, stroke, trauma, epilepsy, acute and chronic kidney injuries, diabetes mellitus, and/or seizures. In some embodiments, derivatives of vitamin K are provided.

26 Claims, 28 Drawing Sheets

Specification includes a Sequence Listing.

(56) References Cited

OTHER PUBLICATIONS

Fass et al., "Effect of Inhibiting Histone Deacetylase with Short-Chain Carboxylic Acids and Their Hydroxamic Acid Analogs on Vertebrate Development and Neuronal Chromatin," *ACS Medicinal Chemistry Letters*, 2:39-42, 2010.
Ferland, "Vitamin K and the nervous system: an overview of its actions," *Advances in Nutrition*, 3:204-212, 2012.
Fukui et al., "Mechanism of glutamate-induced neurotoxicity in HT22 mouse hippocampal cells," *Eur. J. Pharmacol.*, 617:1-11, 2009.
Furian et al., "Methylene blue prevents methylmalonate-induced seizures and oxidative damage in rat striatum," *Neurochemistry International*, 50:164-171, 2007.
Gohil et al., "Nutrient-sensitized screening for drugs that shift energy metabolism from mitochondrial respiration to glycolysis," *Nature Biotechnology*, 28:249-255, 2010.
Grohm et al., "Inhibition of Drp1 provides neuroprotection in vitro and in vivo," *Cell Death Differ*, 2012.
Halliwell et al., "Role of free radicals in the neurodegenerative diseases: therapeutic implications for antioxidant treatment," *Drugs Aging*, 18:685-716, 2001.
Inks et al., "A novel class of small molecule inhibitors of HDAC6," *ACS Chemical Biology*, 7:331-339, 2012.
Josey et al., "Structure-activity relationship study of Vitamin K derivatives yields highly potent neuroprotective agents," *Journal of Medicinal Chemistry*, 56:1007-1022, 2013.
Kroemer and Reed, "Mitochondrial control of cell death," *Nat. Med.*, 6:513-9, 2000.
Lemasters and Nieminen, "Mitochondrial oxygen radical formation during reductive and oxidative stress to intact hepatocytes," *Biosci. Rep.*, 17, 281-91, 1997.
Lheureux and Hantson, "Carnitine in the treatment of valproic acid-induced toxicity," *Clin. Toxicol.* (Phila), 47:101-11, 2009.
Li et al., "Novel role of vitamin k in preventing oxidative injury to developing oligodendrocytes and neurons," *J. Neurosci.*, 23:5816-26, 2003.
Lin and Beal, "Mitochondrial dysfunction and oxidative stress in neurodegenerative diseases," *Nature*, 443:787-95, 2006.
Matsumoto et al., "Secondary elevation of extracellular neurotransmitter amino acids in the reperfusion phase following focal cerebral ischemia," *J. Cereb. Blood Flow Metab.*, 16:114-24, 1996.
Nguyen et al., "The Nrf2-antioxidant response element signaling pathway and its activation by oxidative stress," *J. Biol. Chem.*, 284:13291-5, 2009.
Office Communication issued in U.S. Appl. No. 14/440,155, dated Aug. 18, 2017.
Office Communication issued in U.S. Appl. No. 14/440,155, dated May 26, 2017.
Office Communication issued in U.S. Appl. No. 14/440,155, dated Nov. 25, 2016.
PCT International Search Report and Writen Opinion issued in International Patent Application No. PCT/US2013/069407, dated Feb. 19, 2014.
Pelgrims et al., "Methylene blue in the treatment and prevention of ifosfamide-induced encephalopathy: report of 12 cases and a review of the literature," *British Journal of Cancer* 82:291-294, 2000.
Perucca, "Pharmacological and therapeutic properties of valproate: a summary after 35 years of clinical experience" *CNS Drugs*, 16:695-714, 2002.
Phiel et al., "Histone deacetylase is a direct target of valproic acid, a potent anticonvulsant, mood stabilizer, and teratogen," *J. Biol. Chem.*, 276:36734-36741, 2001.
Porter et al., "Synthesis of new 2-alkylamino 1,4-naphthoquinones as inhibitors of coenzyme Q and as antimalarials," *J. Med. Chem.*, 15(5):504-506, 1972.
Price, "Role of vitamin-K-dependent proteins in bone metabolism," *Annu. Rev. Nutr.*, 8:565-83, 1988.

Reichard et al., "Heme oxygenase-1 induction by NRF2 requires inactivation of the transcriptional repressor BACH1," *Nucleic Acids Res.*, 35:7074-86, 2007.
Riederer et al., "Transition metals, ferritin, glutathione, and ascorbic acid in parkinsonian brains," *J. Neurochem.*, 52:515-20, 1989.
Sagara and Schubert, "The activation of metabotropic glutamate receptors protects nerve cells from oxidative stress," *J. Neurosci.*, 18:6662-71, 1998.
Sakaue et al., "Vitamin K has the potential to protect neurons from methylmercury-induced cell death in vitro," *J. Neurosci. Res.* 89:1052-8, 2011.
Saneto et al., "POLG DNA testing as an emerging standard of care before instituting valproic acid therapy for pediatric seizure disorders," *Seizure*, 19:140-6, 2010.
Shearer et al., "Chemistry, nutritional sources, tissue distribution and metabolism of vitamin K with special reference to bone health," *J. Nutr.*, 126:1181S-86S, 1996.
Silva et al., "Valproic acid metabolism and its effects on mitochondrial fatty acid oxidation: A review," *J. Inherit. Metab. Dis.*, 31(2):205-16, 2008.
Simonian et al., "Oxidative stress in neurodegenerative diseases," *Annu. Rev. Pharmacol. Toxicol.*, 36: 83-106, 1996.
Sims and Muyderman, "Mitochondria, oxidative metabolism and cell death in stroke," *Biochim. Biophys. Acta*, 1802:80-91, 2010.
Smirnova et al., "Dynamin-related protein Drp1 is required for mitochondrial division in mammalian cells," *Mol. Biol. Cell.*, 12:2245-56, 2001.
Sofic et al., "Reduced and oxidized glutathione in the substantia nigra of patients with Parkinson's disease," *Neurosci. Lett.*, 142:128-30, 1992.
Stewart et al., "Polymerase gamma gene POLG determines the risk of sodium valproate-induced liver toxicity," *Hepatology*, 52:1791-6, 2010.
Sundaram et al., "Regulation of sulfotransferase activity by vitamin K in mouse brain," *Arch. Biochem. Biophys.* 277: 109-13, 1990.
Suttie, "Mechanism of action of vitamin K: synthesis of gamma-calboxyglutamic acid," *CRC Crit. Rev. Biochem.*, 8:191-223, 1980.
Tan et al., "Oxytosis: A novel form of programmed cell death," *Curr. Top. Med. Chem.*, 1:497-506, 2001.
Tandon et al, "Synthesis and evaluation of novel 1,4-naphthoquinone derivatives as antiviral, antifungal and anticancer agents," *Bioorg. Med. Chem. Lett.*, 14:2901-4, 2004.
Ten and Starkov, "Hypoxic-ischemic injury in the developing brain: the role of reactive oxygen species originating in mitochondria," *Neurol. Res. Int.*, 2012: 542976, 2012.
Tessier et al., "Diphenylmethylene hydroxamic acids as selective class IIa histone deacetylase inhibitors," *Bioorganic & Medicinal Chemistry Letters*, 19:5684-5688, 2009.
Thijssen and Drittij-Reijnders, "Vitamin K status in human tissues: tissue-specific accumulation of phylloquinone and menaquinone-4," *Br. J. Nutr.*, 75:121-7, 1996.
Tsaioun, "Vitamin K-dependent proteins in the developing and aging nervous system," *Nutr. Rev.*, 57(8): 231-40, 1999.
Valente et al., "The 1,4-naphthoquinone scaffold in the design of cysteine protease inhibitors," *Bioorg. Med. Chem.*, 15:5340-50, 2007.
Vos et al., "Vitamin K2 is a mitochondrial electron carrier that rescues pink1 deficiency," *Science*, 336: 1306-10, 2012.
Waldbaum and Patel, "Mitochondria, oxidative stress, and temporal lobe epilepsy," *Epilepsy Res.*, 88:23-45, 2010.
Waldbaum and Patel, "Mitochondrial dysfunction and oxidative stress: a contributing link to acquired epilepsy?" *J. Bioenerg. Biomembr.*, 42:449-455, 2010.
Wang et al., "The mitochondrial phosphatase PGAM5 functions at the convergence point of multiple necrotic death pathways," *Cell*, 148:228-43, 2012.
Wen et al., "Alternative mitochondrial electron transfer as a novel strategy for neuroprotection," *J. Biol. Chem.*, 286:16504-16515, 2011.

\* cited by examiner

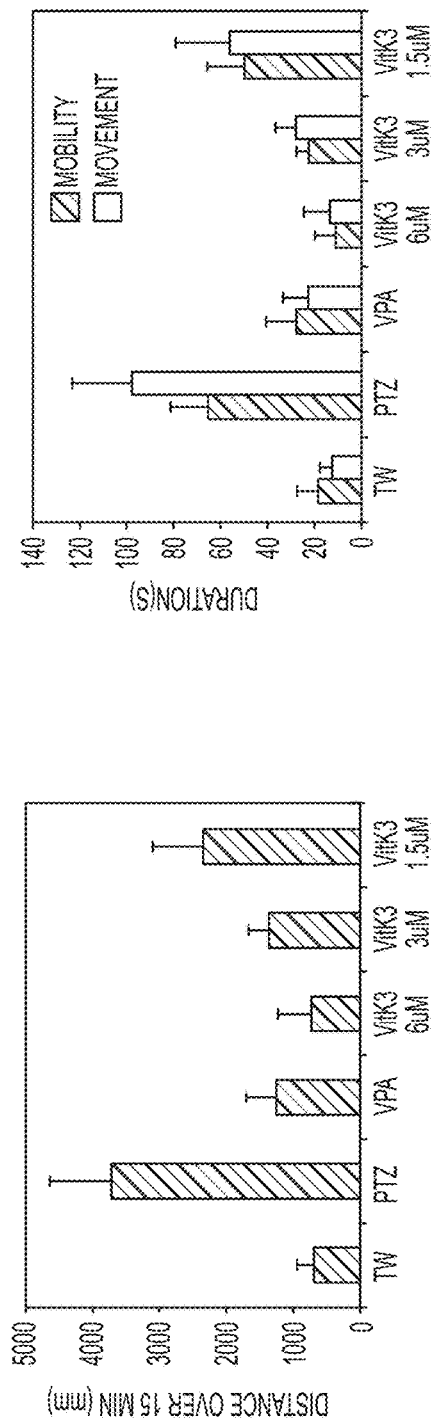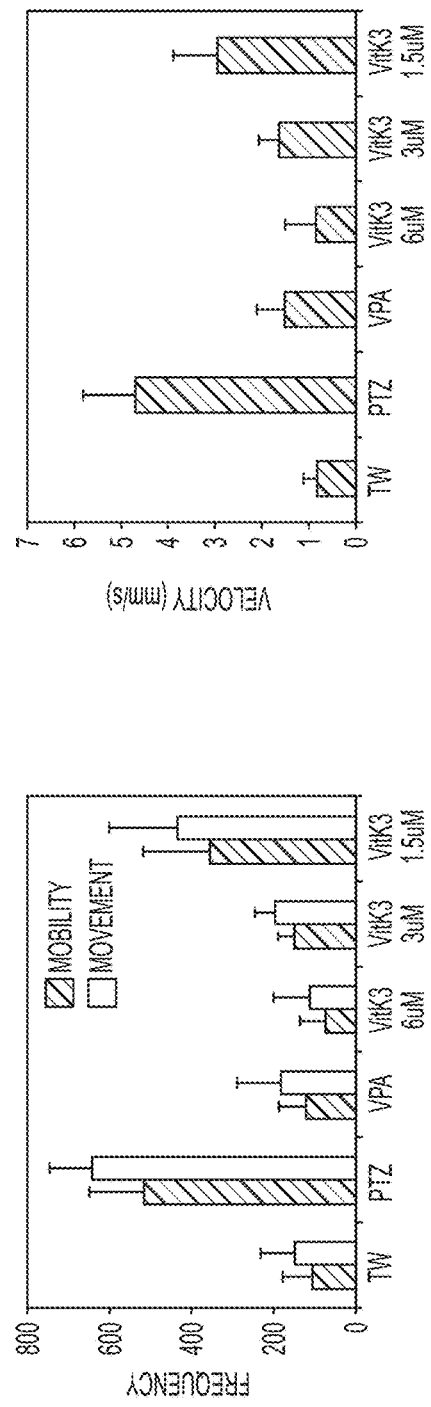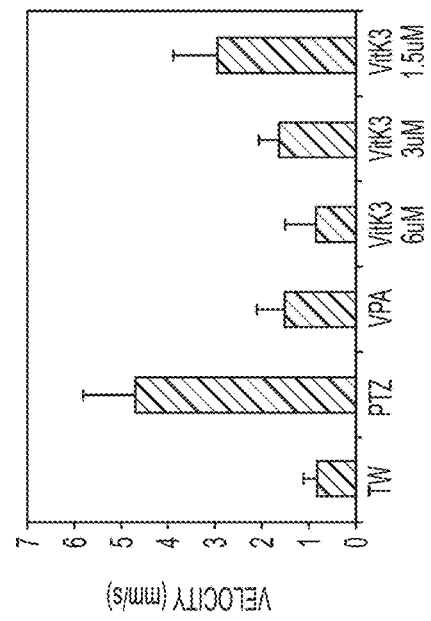

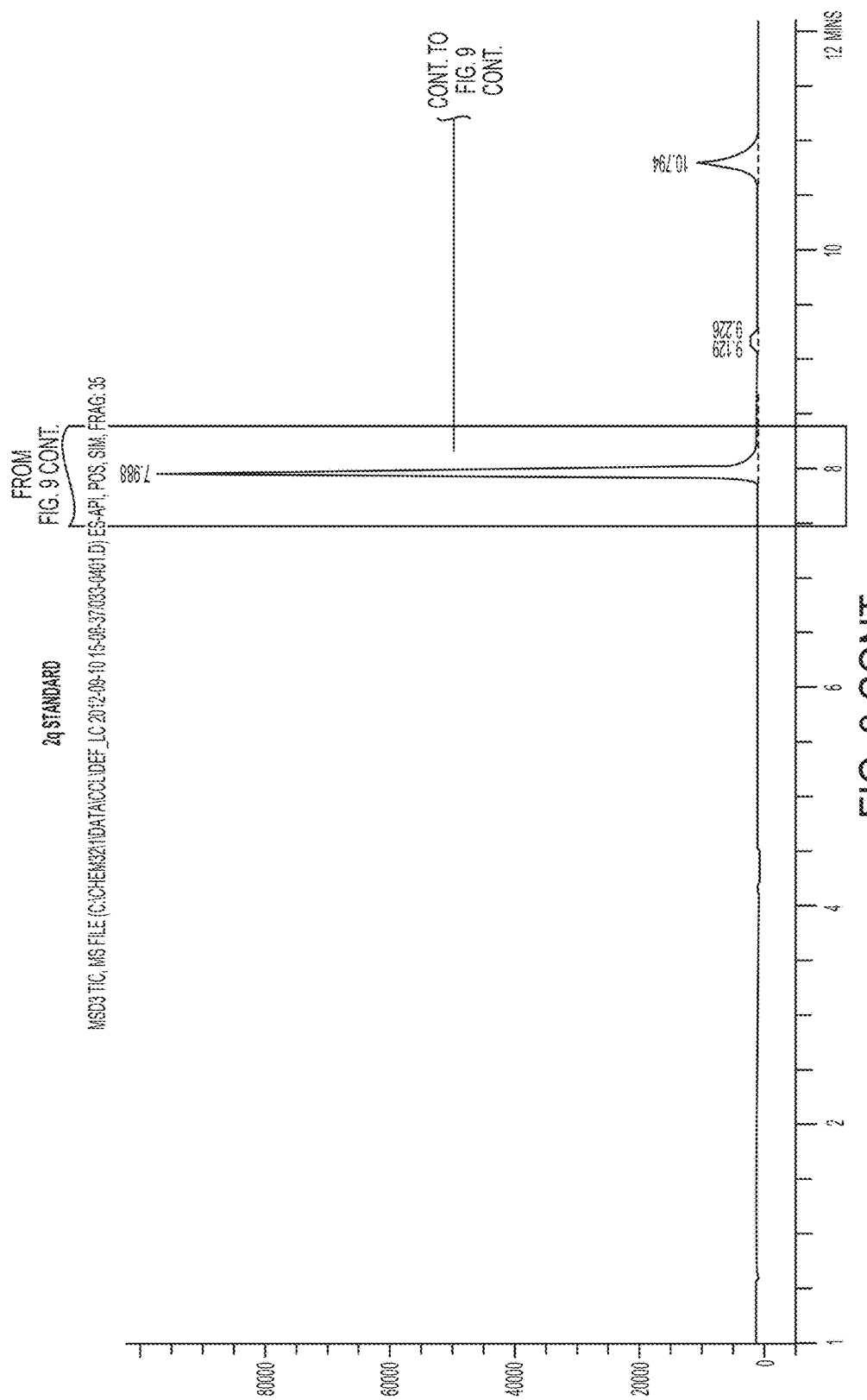

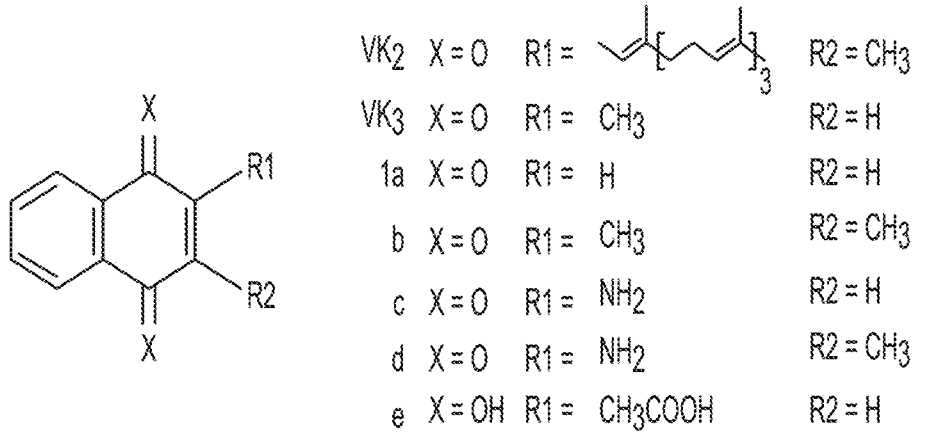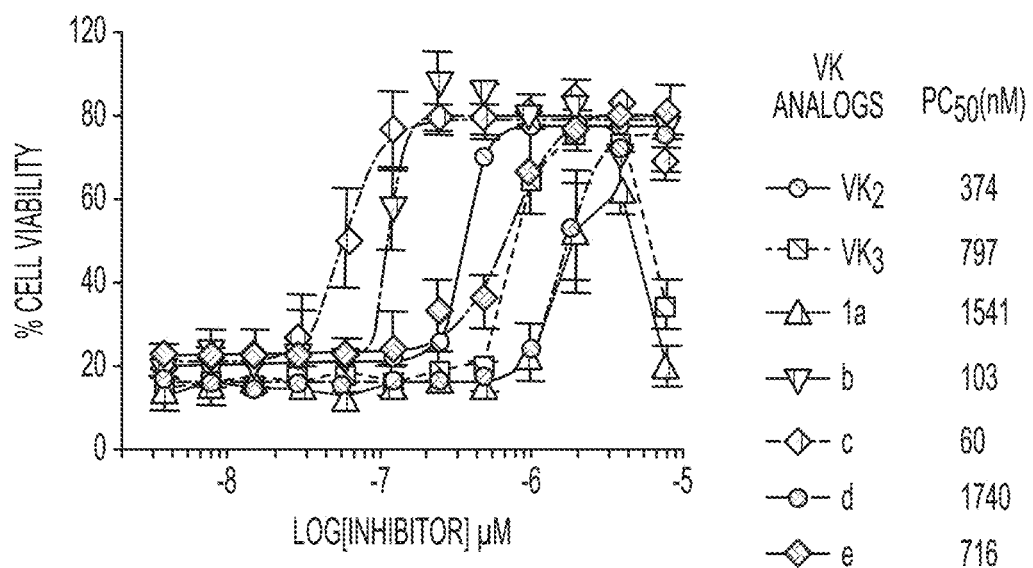
FIG. 16

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
gccaccaagg aggtacacat                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
gcttgttgcg ctctatctcc                                                   20

<210> SEQ ID NO 3
<211> LENGTH: 22
<212> TYPE: DNA
<213> ORGANISM: Artificial Sequence
<220> FEATURE:
<223> OTHER INFORMATION: Synthetic Primer

<400> SEQUENCE: 3
tgacaccatt aggtcgggaa ct                                                22

<210> SEQ ID NO 4
<211> LENGTH: 21
<212> TYPE: DNA
<213> ORGANISM: Artificial Sequence
<220> FEATURE:
<223> OTHER INFORMATION: Synthetic Primer

<400> SEQUENCE: 4
```

-continued

| tactgcacgg gtcatagagg a | 21 |

<210> SEQ ID NO 5
<211> LENGTH: 21
<212> TYPE: DNA
<213> ORGANISM: Artificial Sequence
<220> FEATURE:
<223> OTHER INFORMATION: Synthetic Primer

<400> SEQUENCE: 5

| aggatgggag gtactcgaat c | 21 |

<210> SEQ ID NO 6
<211> LENGTH: 22
<212> TYPE: DNA
<213> ORGANISM: Artificial Sequence
<220> FEATURE:
<223> OTHER INFORMATION: Synthetic Primer

<400> SEQUENCE: 6

| aggcgtcctt ccttatatgc ta | 22 |

<210> SEQ ID NO 7
<211> LENGTH: 21
<212> TYPE: DNA
<213> ORGANISM: Artificial Sequence
<220> FEATURE:
<223> OTHER INFORMATION: Synthetic Primer

<400> SEQUENCE: 7

| acccgcctca cattgaaatc c | 21 |

<210> SEQ ID NO 8
<211> LENGTH: 21
<212> TYPE: DNA
<213> ORGANISM: Artificial Sequence
<220> FEATURE:
<223> OTHER INFORMATION: Synthetic Primer

<400> SEQUENCE: 8

| ggcgtatgta tcagtctcag t | 21 |

<210> SEQ ID NO 9
<211> LENGTH: 21
<212> TYPE: DNA
<213> ORGANISM: Artificial Sequence
<220> FEATURE:
<223> OTHER INFORMATION: Synthetic Primer

<400> SEQUENCE: 9

| cactgcaagc tgaaactgac c | 21 |

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10

| gcggcgagga tgaactctaa | 20 |

COMPOSITIONS AND METHODS FOR TREATING NEUROLOGICAL DISEASES OR INJURY

This application is a continuation of U.S. patent application Ser. No. 14/440,155, filed May 1, 2015, which is a national phase application under 35 U.S.C. § 371 of International Application No. PCT/US2013/069407, filed Nov. 11, 2013, which claims the benefit of U.S. Provisional Patent Application No. 61/724,732, filed Nov. 9, 2012. The entire contents of the above-referenced disclosures are specifically incorporated herein by reference.

The invention was made with government support under Grant Nos. RR012546, HL007260, RR024485, and GM103542 awarded by the National Institutes of Health. The government has certain rights in the invention.

BACKGROUND OF THE INVENTION

Pursuant to 37 C.F.R. 1.821(c), a sequence listing is submitted herewith as an ASCII compliant text file named "MESCP0071USC1_ST25.txt", created on Dec. 5, 2017 and having a size of ~3 kilobytes. The content of the aforementioned file is hereby incorporated by reference in its entirety.

1. Field of the Invention

The present invention relates generally to the field of medicinal chemistry and medicine. More particularly, it concerns compositions and methods for treating neurological or mitochondrial diseases or injury.

2. Description of Related Art

An increasing amount of experimental evidence implicates oxidative stress as one of the major causes of delayed cell death in a variety of neurodegenerative diseases, as well as in stroke, trauma, and seizures. In many of these diseases and disorders, mitochondrial generated reactive oxygen species react with and damage cellular components, resulting in caspase independent cell death (Beckman and Ames, 1998; Simonian and Coyle, 1996; Halliwell, 2001). In addition, one of the hallmarks of oxidative stress is a decrease in the reduced form of the major cellular antioxidant, glutathione (GSH), which has been suggested to play a key role in the degeneration of dopaminergic neurons (Riederer et al., 1989; Sofic et al., 1992). Neuronal GSH synthesis is largely dependent on the exchange of intracellular glutamate for extracellular cystine via the cystine/glutamate antiporter. Concentrations of extracellular glutamate as low as 100 µM inhibit this antiporter (Sagara and Schubert, 1998), and it has been previously reported that extracellular levels of glutamate in the central nervous system (CNS) can reach concentrations as high as 10 mM following injury (Matsumoto et al., 1996). This depletion of GSH leads to a unique form of mitochondrial driven programmed necrotic cell death (necroapoptosis or oxytosis), which does not depend on caspase activation (Albrecht et al., 2010.). Recent studies have shown programmed necrotic cell death to be a tightly controlled process involving multiple inter-connected kinases, RIP1, RIP3, MLKL, and the mitochondrial phosphatase, phosphoglycerate mutase family member 5 (PGAM5), via its regulation of dynamin-related protein 1 (Drp-1) and subsequent mitochondrial fragmentation. In addition, PGAM5 has been shown to be at the convergent point of multiple cell death pathways. Knock-down of PGAM5 prevents both extrinsic (Tumor-necrosis factor-α) and intrinsic (tert-butyl hydroperoxide, and calcium ionophore) induced cell death (Wang et al., 2012).

Vitamin K (VK) is a group of structurally similar, fat soluble vitamins that play well known roles in the post-translational modification of proteins required for blood coagulation and bone metabolism (Suttie, 1980; Price, 1988). There are two forms of naturally occurring VK, phylloquinone ($VK_1$) and the menaquinones ($VK_2$). A synthetic form of VK, menadione ($VK_3$) is also available and used in animal feeds and supplements. All forms of VK possess a common 2-methyl-1,4-naphthoquinone core structure, but individual forms differ in the length and degree of saturation of an aliphatic side chain attached to the 3' position. $VK_1$, found primarily in green leafy vegetables (Shearer et al., 1996), is a single compound containing a saturated side chain consisting of four isoprenoid subunits. While it is the major dietary source of VK, post mortem (Thijssen and Drittij-Reijinders, 1996) and animal studies have indicated that concentrations are significantly lower in the brain and other tissues compared with the $VK_2$. There are several forms of $VK_2$ that are classified based on the length of the unsaturated 3' side chain. The major form of $VK_2$ (>90%) found in animal tissues has a four isoprenoid unit (geranylgeranyl) side chain. Although there is a small dietary presence of $VK_2$, it is primarily obtained by removal of the phytyl group of $VK_1$ followed by a subsequent geranylgeranylation that has been shown to occur in cultured primary brain slices and neurons, indicating an as of yet unknown but important function for $VK_2$ in brain function (Nagai, 1979).

$VK_2$ does not effectively cross the blood-brain barrier. Thus, there is a need for synthetic compositions that can cross the blood-brain barrier that may be used to treat conditions associated with a VK deficiency. Clearly there is a need for new compounds and methods for treating neurological diseases and injury.

SUMMARY OF THE INVENTION

The present invention overcomes limitations in the prior art by providing compositions and methods for the treatment of a neurological or mitochondrial disease or injury. In some aspects, derivatives of vitamin K (VK) are provided that may be therapeutically administered to a subject, such as a human patient, to promote neuroprotection or anti-epileptic effects, or to treat a neurological or mitochondrial disease or injury. In some embodiments, compositions are provided that exhibit potent neuroprotecitve and/or anti-eplipetic properties while exhibiting low or undetectable toxicity.

Historically known for its role in blood coagulation and bone formation, VK may be an important nutrient for brain function and homeostatsis. Without wishing to be bound by any theory, suboptimal VK status may be associated with or contribute to age-related cognitive decline. Oxidative stress can play a critical role in the pathogenesis of neurodegenerative diseases, and some evidence has been provided that VK may be able to protect neurons and oligodentrocytes from oxidative injury and/or promote recovery from mitochondrial defects associated with Parkinson's disease. As shown herein and in the below specification and examples, the inventors have used a chemical to define the optimal and minimum pharmacophore responsible for the neuroprotective effects. In doing so, the inventors have developed a series of VK analogs with favorable drug characteristics and potency that provide full protection at nanomolar concentrations in a well-defined model of neuronal oxidative stress. The inventors also have characterized key cellular responses and biomarkers consistent with the compounds' ability to rescue cells from oxidative stress induced cell death. In addition, these compounds exhibit potent anti-epileptic activity comparable to ovalporic acid, one of the most commonly used anti-epileptic drugs, in zebrafish epileptic model.

An aspect of the present invention relates to a method of treating a neurological disease or injury in a mammalian subject comprising administering to the subject a compound in an amount sufficient to treat the neurological disease or injury, wherein the compound is defined by the formula:

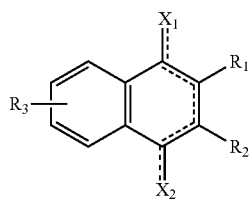

wherein $X_1$ and $X_2$ are each independently selected from the group consisting of =O, —O—CH$_3$, and C$_{1-6}$ alkoxy; wherein $R_3$ is —H or halogen; wherein $R_2$ is —H, —CH$_3$, or C$_{1-6}$ alkyl; wherein $R_1$ is selected from the group consisting of —NH$_2$, —C(O)OH,

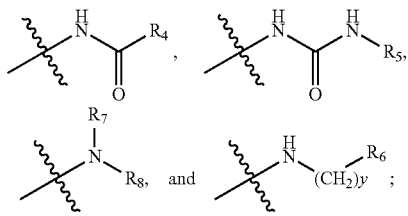

wherein $R_4$ is C$_{1-6}$ alkyl, C$_{3-8}$ cycloalkyl, C$_{6-12}$ aryl, —O—CH$_3$, —(CH$_2$)$_{y2}$—C$_{6-12}$ aryl, —CF$_3$, or

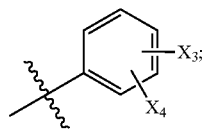

wherein $X_3$ and $X_4$ are each independently selected from the list consisting of —H, —CH$_3$, halogen, —O—CH$_3$, and phenyl; wherein y and y2 are each independently 1-3; wherein $R_5$ is C$_{1-12}$ alkyl, C$_{6-12}$ aryl, and —(CH$_2$)$_{y2}$—C$_{6-12}$ aryl; wherein $R_7$ is —H, —CH$_3$, or C$_{1-3}$ alkyl; wherein $R_6$ is C$_{1-12}$ alkyl, C$_{3-8}$ cycloalkyl, C$_{6-12}$ aryl, —O—CH$_3$, C$_{2-10}$ alkynyl, heteroatom-substituted C$_{6-12}$ aryl, C$_{2-10}$ alkenyl, or

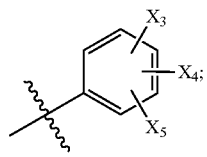

wherein $R_8$ is C$_{1-12}$ alkyl, C$_{3-8}$ cycloalkyl, C$_{6-12}$ aryl, —O—CH$_3$, —(CH$_2$)$_{y2}$—C$_{6-12}$ aryl, C$_{2-10}$ alkenyl, C$_{2-10}$ alkynyl, heteroatom-substituted C$_{6-12}$ aryl, —(CH$_2$)$_{y2}$—C$_{6-12}$ heteroatom-substituted aryl,

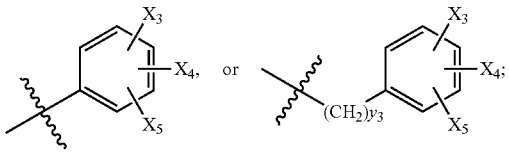

wherein $y_3$ is 1-3; wherein $X_3$, $X_4$, and $X_5$ are each independently —H, halogen, C$_{1-6}$ alkyl, —CF3, —C(O)O—CH$_3$, or —O—CH$_3$; or a pharmaceutically acceptable salt, hydrate or solvate thereof. The mammal may be a human, a horse, a dog, a cat, a primate, an ape, a monkey, a mouse, or a rat. The neurological disease or injury may comprises a stroke or trauma to the central nervous system of the subject. In some embodiments, the subject has a neurological disease. The neurological disease may be a neurodegenerative disease or may comprises a mitochondrial dysfunction. The neurological disease may comprise epilepsy, seizures, or ataxia. The epileptic disorder may be, e.g., Lennox-Gastaut syndrome (LGS), benign Rolandic epilepsy, frontal lobe epilepsy, infantile spasms, juvenile myoclonic epilepsy, juvenile absence epilepsy, childhood absence epilepsy (pyknolepsy), hot water epilepsy, Lennox-Gastaut syndrome, Landau-Kleffner syndrome, Dravet syndrome, progressive myoclonus epilepsies, reflex epilepsy, Rasmussen's syndrome, temporal lobe epilepsy, limbic epilepsy, status epilepticus, abdominal epilepsy, massive bilateral myoclonus, catamenial epilepsy, Jacksonian seizure disorder, Lafora disease, or photosensitive epilepsy, etc. In some embodiments, the neurological disease is Alzheimer's disease, Parkinson's disease, amyotrophic lateral sclerosis (ALS) or Lou Gehrig's disease, an ataxia disease, MERRF patients (patients with myoclonic epilepsy and ragged red fibers), Alpers syndrome, muscular dystrophy, autism, Huntington's disease, a progressive palsies, Charcot-Marie-Tooth disease, metabolic diaseases resulting in neuronal degradation such as Leigh syndrome, neuropathy, ataxia, retinitis pigmentosa, or neurological diseases with diabetes mellitus in Friedreich ataxia, or an ataxia resulting from a mitochondrial or metabolic disfunction. In some embodiments, the neurological disorder is an addition disorder such as, e.g., cocaine addition, methamphetamine addiction, alcoholism or alcohol dependence. In some preferred embodiments, the neurological disorder is an epileptic disorder. In some aspects, a compound of the present invention may be used to treat a migraine, bipolar disorder, borderline personality disorder, post traumatic stress disorder (PTSD), or to promote recovery from a hypoxic or ischemic injury or stroke.

In some embodiments, $R_3$ is —H and/or $R_2$ is —H. The compound may be defined by the formula:

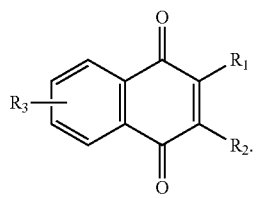

The compound may be defined by the formula:
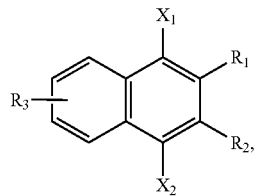
wherein X1 and X2 are each independently —O—CH$_3$ or C$_{1-6}$ alkoxy. In some embodiments, R$_3$ is —H and R$_2$ is —H. In some embodiments, X$_1$ and X$_2$ are =O. R$_1$ may be NH$_2$ or
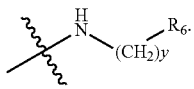
In some embodiments, y=1. R$_1$ may be selected from the list consisting of
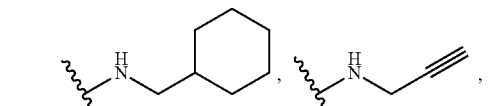
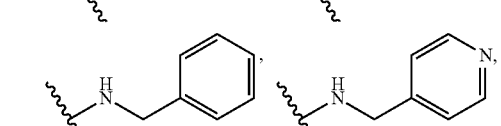
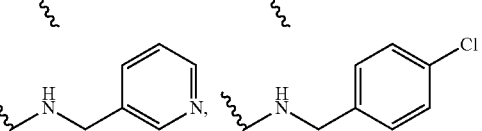
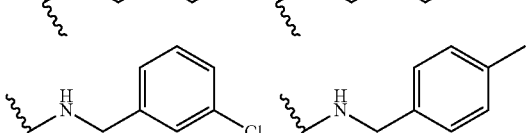
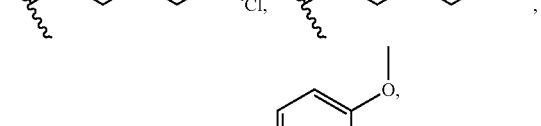
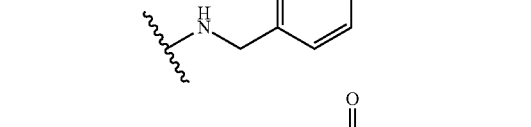
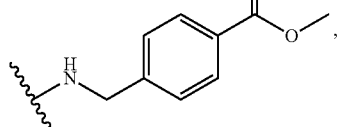
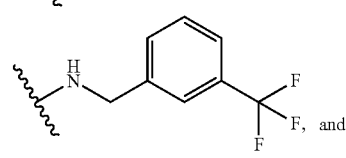
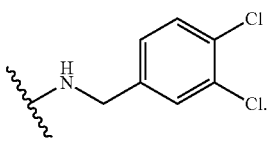
In some embodiments, R$_1$ is selected from the list consisting of
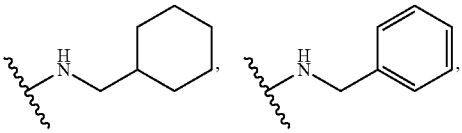
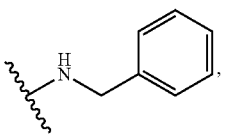
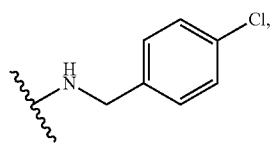
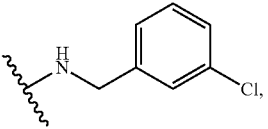
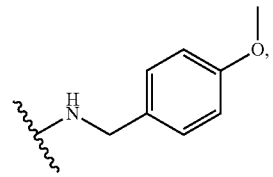
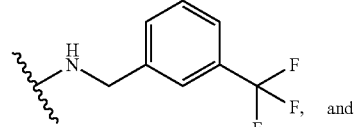
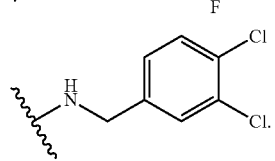
In some embodiments, R1 is
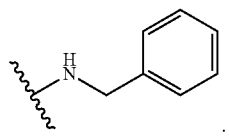 [SMILES: *NCc1ccccc1]

$R_1$ may be

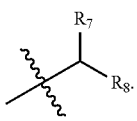

$R_7$ may be H. $R_8$ may be

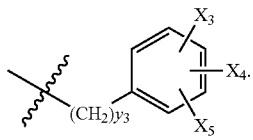

In some embodiments, y3=1. In some embodiments, $X_3$ is halogen, $X_4$ is halogen, and $X_5$ is hydrogen. In some embodiments, $X_3$ is halogen, $X_4$ is hydrogen, and $X_5$ is hydrogen. In some embodiments, $R_8$ is

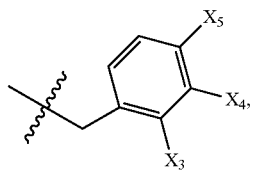

wherein $X_4$ is halogen. In some embodiments, $X_3$, $X_4$, and $X_5$ are —H. In some embodiments, the compound is

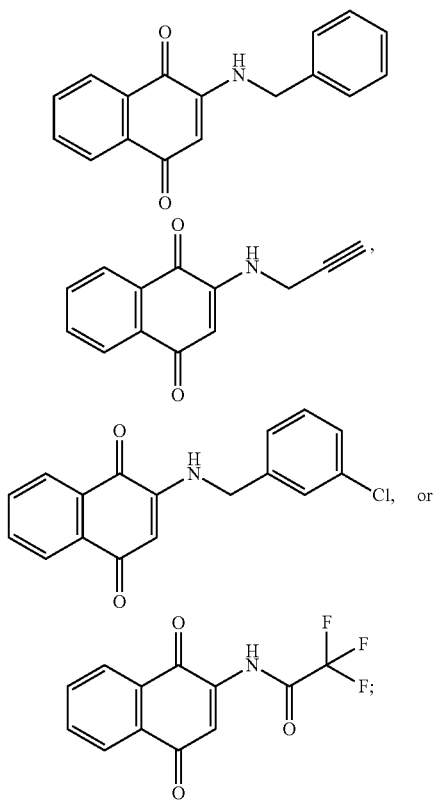

or a salt thereof.

Another aspect of the present invention relates to a method of treating a metabolic disease in a mammalian subject comprising administering to the subject a compound of the present invention in an amount sufficient to treat the metabolic disease. The subject may be a human. The metabolic disease may be a mitochondrial disease. The compound may be administered orally, intravenously, or via a method of delivery described herein. In some embodiments, the mitochondrial disease is Alpers syndrome, Leigh's Disease, autism, Parkinson's disease, Huntington's disease, Alzheimer's disease, amyotrophic lateral sclerosis (ALS) or Lou Gehrig's disease, muscular dystrophy, chronic fatigue, Friedreich ataxia, a progressive palsy, Charcot-Marie-Tooth disease, an acute kidney injury (AKI), a chronic kindney injury or disease, obesity, or diabetes mellitus. In some embodiments, the metabolic disease is characterized by a deficiency in the subject of metabolizing vitamin $K_3$ into vitamin $K_2$. The mitochondrial disease may be, e.g., a mitochondrial myopathy, Kearns-Sayre syndrome (KSS), chronic progressive external ophthalmoplegia (CPEO), diabetes mellitus and deafness (DAD), Leber's hereditary optic neuropathy (LHON), Leigh syndrome, "neuropathy, ataxia, retinitis pigmentosa, and ptosis" (NARP), "myoneurogenic gastrointestinal encephalopathy" (MNGIE), MERRF, "mitochondrial myopathy, encephalomyopathy, lactic acidosis, or stroke-like symptoms" (MELAS). In some preferred embodiments, the mitochondrial disease is Friedreich's ataxia. Without wishing to be bound by any theory, data is provided herein that is consistent with the idea that some of the compounds of the present invention that may affect or target mitochondrial function.

Yet another aspect of the present invention relates to a pharmaceutical preparation comprising a compound of the formula:

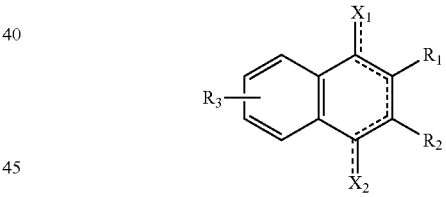

wherein $X_1$ and $X_2$ are each independently selected from the group consisting of =O, —O—$CH_3$, and $C_{1-6}$-alkoxy; wherein $R_3$ is —H or halogen; wherein $R_2$ is —H, —$CH_3$, or $C_{1-6}$ alkyl; wherein $R_1$ is selected from the group consisting of —$NH_2$, —C(O)OH,

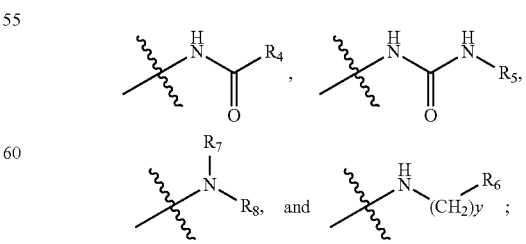

wherein $R_4$ is $C_{1-6}$ alkyl, $C_{3-8}$ cycloalkyl, $C_{6-12}$ aryl, —O—$CH_3$, —$(CH_2)_{y2}$—$C_{6-12}$ aryl, —$CF_3$, or

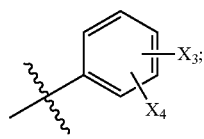

wherein $X_3$ and $X_4$ are each independently selected from the list consisting of —H, —CH$_3$, halogen, —O—CH$_3$, and phenyl; wherein y and y2 are each independently 1-3; wherein $R_5$ is $C_{1-12}$ alkyl, $C_{6-12}$ aryl, and —(CH$_2$)$_{y2}$—C$_{6-12}$ aryl; wherein $R_7$ is —H, —CH$_3$, or $C_{1-3}$ alkyl; wherein $R_6$ is $C_{1-12}$ alkyl, $C_{3-8}$ cycloalkyl, $C_{6-12}$ aryl, —O—CH$_3$, $C_{2-10}$ alkynyl, heteroatom-substituted $C_{6-12}$ aryl, $C_{2-10}$ alkenyl, or

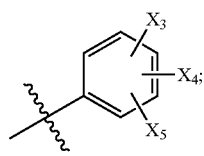

wherein $R_8$ is $C_{1-12}$ alkyl, $C_{3-8}$ cycloalkyl, $C_{6-12}$ aryl, —O—CH$_3$, —(CH$_2$)$_{y2}$—C$_{6-12}$ aryl, $C_{2-10}$ alkenyl, $C_{2-10}$ alkynyl, heteroatom-substituted $C_{6-12}$ aryl, —(CH$_2$)$_{y2}$—C$_{6-12}$ heteroatom-substituted aryl,

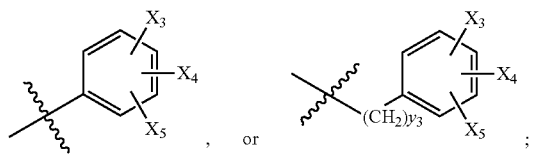

wherein $y_3$ is 1-3; wherein $X_3$, $X_4$, and $X_5$ are each independently —H, halogen, $C_{1-6}$ alkyl, —CF3, —C(O)O—CH$_3$, or —O—CH$_3$; or a pharmaceutically acceptable salt, hydrate or solvate thereof; and an excipient. The pharmaceutical preparation may be formulated for oral delivery. The pharmaceutical preparation may comprise a tablet, capsule, or powder. In some embodiments, the pharmaceutical preparation is formulated for intravenous, peritoneal, subcutaneous, intrathecal, intracerebral, intraspinal, intrathecal, nasal, inhalational, sublingual, intramuscular, or per os (oral) delivery. The compound may be comprised in a liposome, unilamellar liposome, multilamellar liposome, multivesicular liposome, nanoparticle, emulsion, or lipid formulation. In some embodiments, $R_3$ is —H and/or $R_2$ is —H. In some embodiments, the compound is defined by the formula:

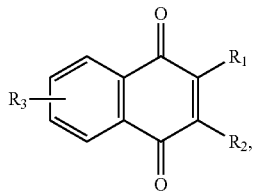

In some embodiments, the compound is defined by the formula:

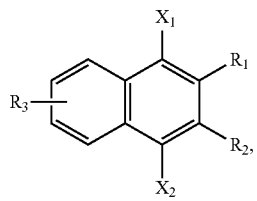

wherein X1 and X2 are each independently —O—CH$_3$ or $C_{1-6}$ alkoxy. In some embodiments, $R_3$ is —H and $R_2$ is —H. In some embodiments, $X_1$ and $X_2$ are =O. $R_1$ may be NH$_2$ or

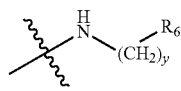

In some embodiments, y=1. $R_1$ may be selected from the list consisting of

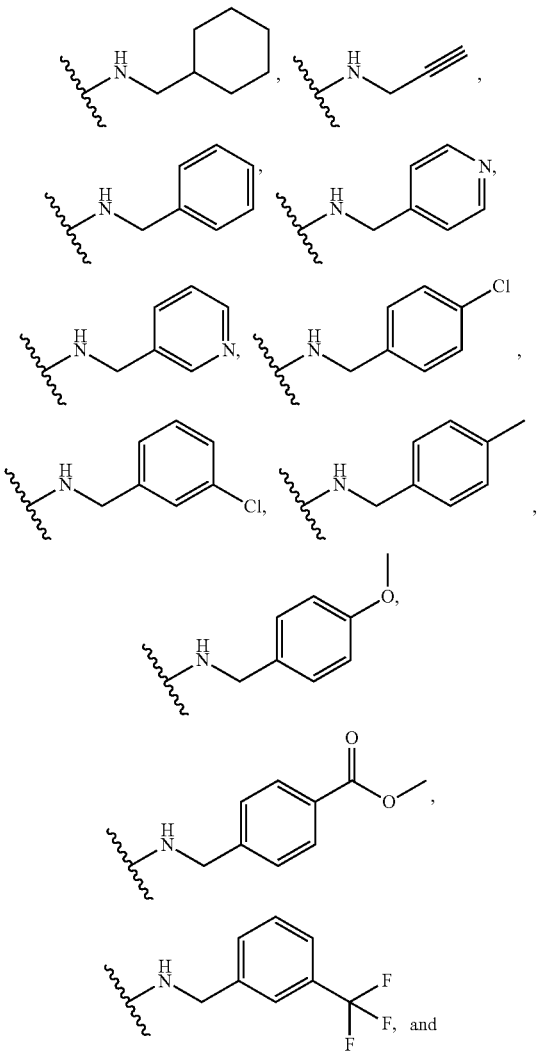

-continued

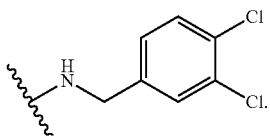

In some embodiments, $R_1$ is selected from the list consisting of

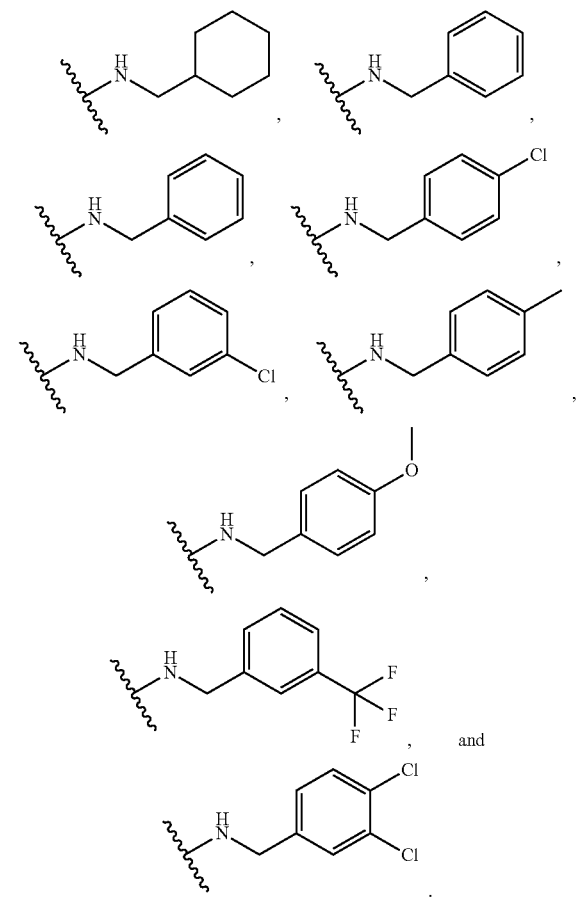

In some embodiments, R1 is

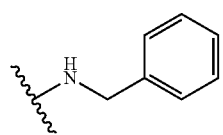

$R_1$ may be

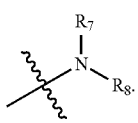

$R_7$ may be H. In some embodiments, $R_8$ is

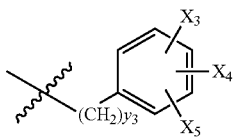

In some embodiments, y3=1. In some embodiments, $X_3$ is halogen, $X_4$ is halogen, and $X_5$ is hydrogen. In some embodiments, $X_3$ is halogen, $X_4$ is hydrogen, and $X_5$ is hydrogen. In some embodiments, R8 is

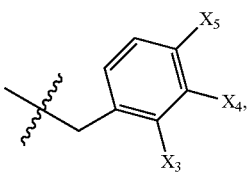

wherein X4 is halogen. In some embodiments, $X_3$, $X_4$, and $X_5$ are —H. In some embodiments, the compound is

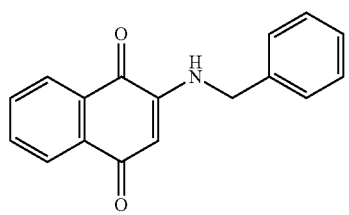

,

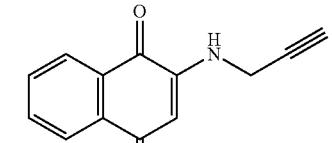

,

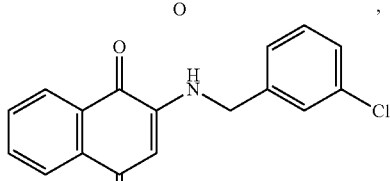

, or

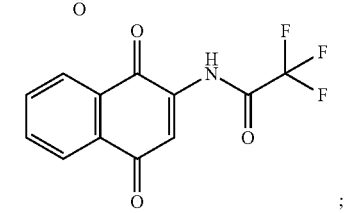

;

or a salt thereof.

In some embodiments, the compound is administered locally. In some embodiments, the compound is administered systemically. In some embodiments, the compound is administered orally, intraadiposally, intraarterially, intraarticularly, intracranially, intradermally, intralesionally, intramuscularly, intranasally, intraocularly, intrapericardially, intraperitoneally, intrapleurally, intraprostaticaly, intrarectally, intrathecally, intratracheally, intratumorally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, via localized perfusion, bathing target cells directly, or any combination thereof. For example, in some variations, the compound is administered intravenously, intra-arterially or orally. For example, in some variations, the compound is administered orally.

In some embodiments, the compound is formulated as a hard or soft capsule, a tablet, a syrup, a suspension, a wafer, or an elixir. In some variations, the soft capsule is a gelatin capsule. In some variations, hard capsule, soft capsule, tablet or wafer further comprising a protective coating. In some variations, the formulated compound comprises an agent that delays absorption. In some variations, the formulated compound further comprises an agent that enhances solubility or dispersibility. In some variations, the compound is dispersed in a liposome, an oil in water emulsion or a water in oil emulsion.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

FIG. 1B. Synthetic approach and selective criteria to generate more potent and non-toxic VK analogs.

FIG. 2A. Depletion of total cellular GSH occurs in HT22 cells treated with glutamate. Co-treatment with $VK_2$, 2j, or 2q (500 nM) does not prevent GSH. Nec-1 (50 µM), Ideb (5 µM), and Trolox (25 µM) also did not prevent GSH depletion. FIG. 2B. ROS accumulation measured using Rho123. Co-treatment with 250 nM 2j and 2q prevent the accumulation of ROS in response to glutamate treatment, with $VK_2$ being less effective. One-way ANOVA with Bonferroni's posttest was used to compare mean intensities. Drug treatments were all significantly less than glutamate treatment, with 2j and 2q treatments being statistically similar to control, p<0.01. FIG. 2C. Increase in ROS species is visualized with $CM-H_2DCFDA$. Results are consistent with those found with Rho123.

[a]In vitro neuroprotective activity and
[b]neurotoxicity assessed by treating HT22 cells with various concentrations of compounds with or without 10 mM glutamate for 24 hrs. Cell viability was estimated by treating cells with MTS and measuring absorbance at 490 nM. $PC_{50}$, concentration producing 50% protection, values calculated using GraphPad Prism based on 12 point titrations, n≥4; $TC_{50}$, concentration producing 50% toxicity, values calculated using GraphPad Prism based on 7 point titrations, n≥3.

Figure 3A:
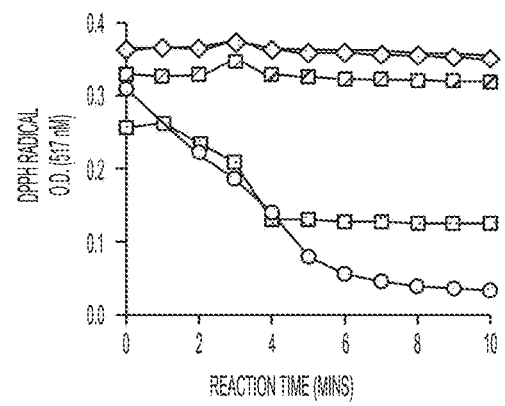
Figure 3B:
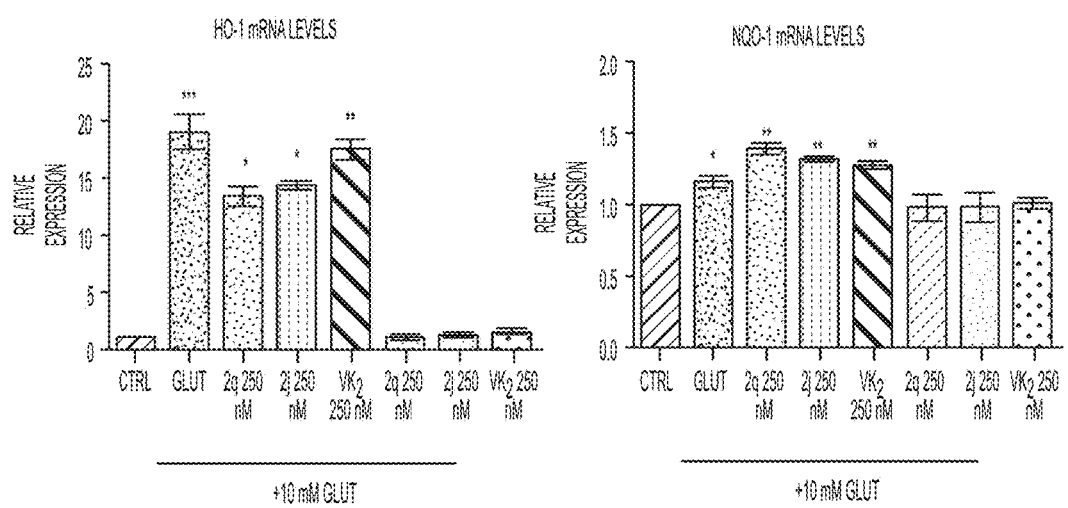

FIGS. 3A-3B—FIG. 3A. Free radical scavenging capacity determined by monitoring the disappearance of the optical absorbance of the stable free radical DPPH. Known free radical scavengers vitamin C (squares filled with dots) and Trolox (●) used as controls. $VK_2$ (squares filled with lines), 2j (▼), and 2q (▲) did not show direct antioxidant capacity. All compounds tested at 20 µM FIG. 3B. Expression of antioxidant response genes. Significant cellular antioxidant responses are elicited in glutamate treated HT22 cells with significant increase in HO-1 and NQO-1 gene expression. $VK_2$, 2q, and 2j significantly decreased HO-1 expression but did not affect NQO-1 expression. One-way ANOVA with Bonferroni's posttest was used to compare mean levels (n=3), p<0.01.

Figure 4A:
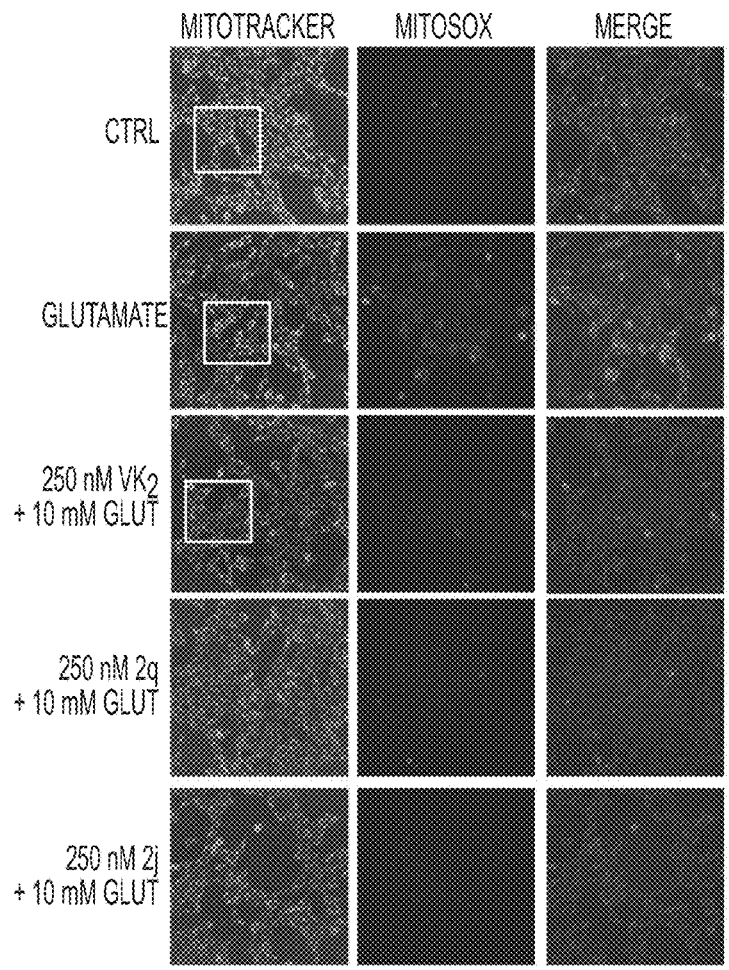
Figure 4B:
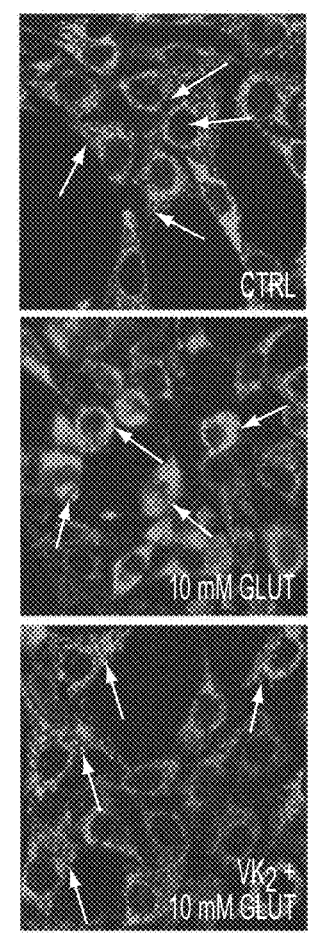

FIGS. 4A-4B—FIG. 4A. Glutamate treatment increases superoxide generation within mitochondria. MitoTracker DR (green) stains for active mitochondria and MitoSOX (red) selectively reacts with superoxide. Co-localization of MitoTracker and MitoSox indicates that the superoxide is likely generated by mitochondria. FIG. 4B. Mitochondria under normal cellular conditional exhibits a complex network morphology (arrows in "CTRL" and "$VK_2$+" panels). Under glutamate injury, mitochondrial fragmentation occurs (arrows in "10 mM Glut" panel) and $VK_2$ treatment maintains normal mitochondrial morphology.

Figure 5A:
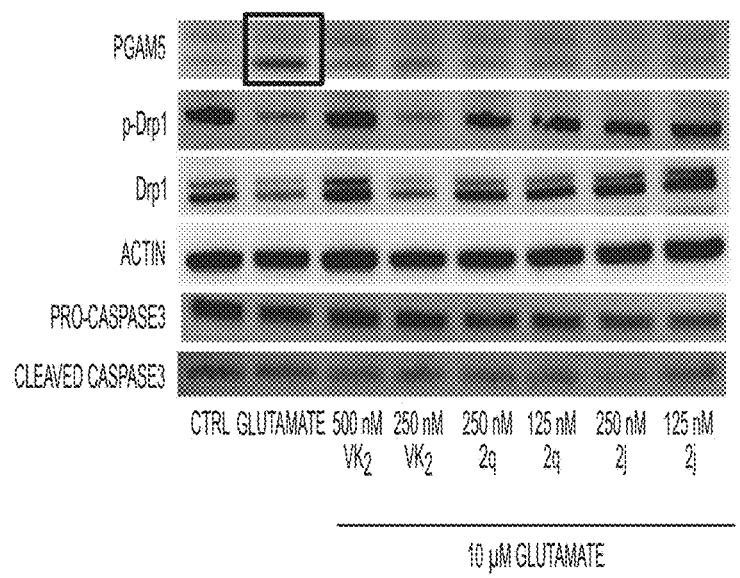
Figure 5B:
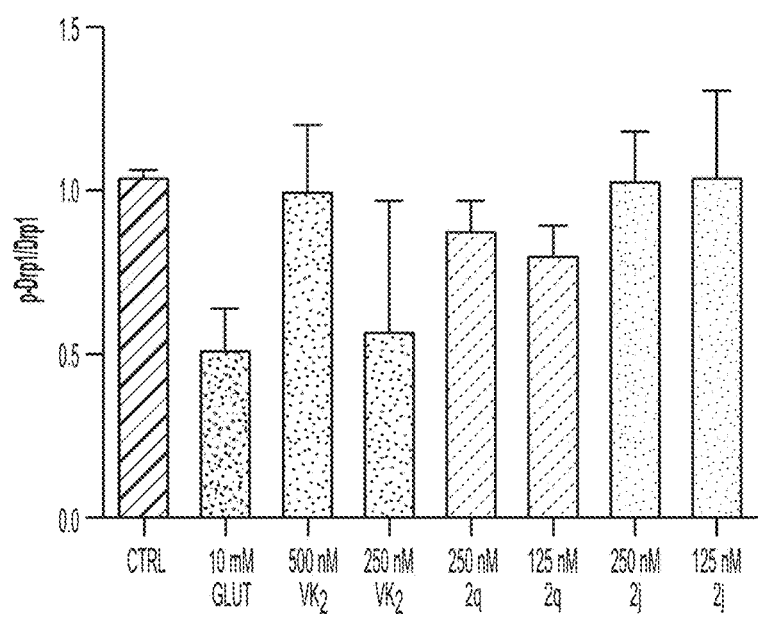

FIGS. 5A-5B—FIG. 5A. Western blot analysis of HT22 cells treated with 10 mM glutamate for 16 hrs. Glutamate treatment causes a dramatic increase in a cleavage product (lower band) of PGAM5-L (top band), as well as a decrease in phosphorylation of Drp1 at residue Ser b PGAM5 cleavage and activation and subsequent dephosphorylation of Drp1. FIG. 5B. Densitometric analysis confirms that there is a significant decrease in phosphorylation of Drp1 at residue Ser 637 with 10 mM glutamate treatment for 16 hrs, and the phosphorylation state is maintained by co-treatment with 500 nM $VK_2$ and compounds 2q or 2j at 250 and 125 nM. Co-treatment with 250 nM $VK_2$ was less effective. One-way ANOVA with Bonferroni's posttest was used to compare mean levels, p<0.01.

Figure 6A:
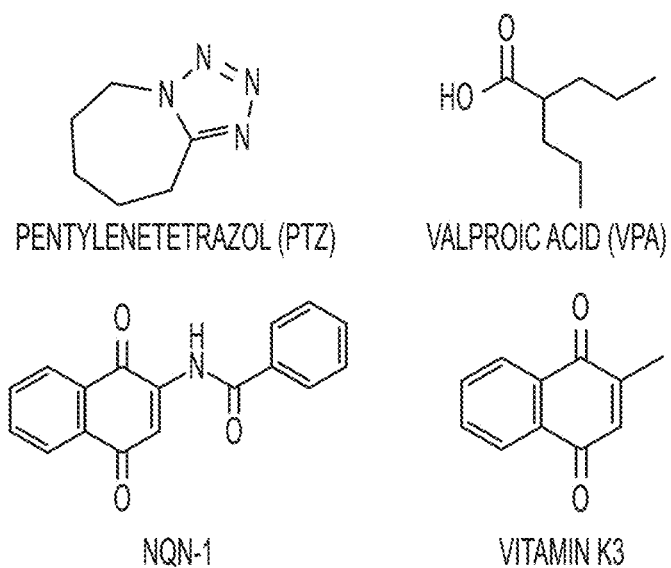
Figure 6B:
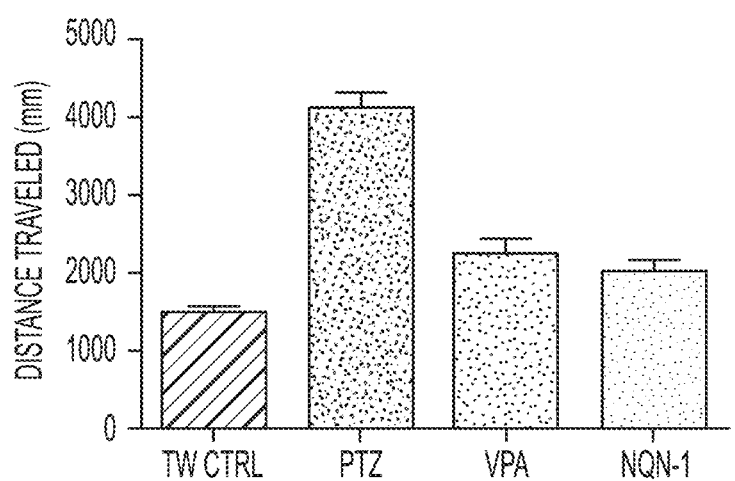

FIGS. 6A-6B—FIG. 6A. Chemical structures of pentylenetetrazol (PTZ), valproic acid (VPA), and NQN-1. FIG. 6B. NQN-1 significantly reduces seizure activity in PTZ-treated 6 dpf zebrafish to levels observed for VPA, but at a more than 1000-fold lower concentration than the required concentration of VPA.

FIGS. 7A-7D—Titration of Vitamin K3 reveals that efficacy against seizures is dose dependent and 6 µM is most effective. FIG. 7A. VPA's and $VK_3$'s effects on distance traveled, which directly correlates with degrees of seizure activities. FIG. 7B. Duration of mobility and movement in seconds. FIG. 7C. Frequency of mobility and movement. FIG. 7D. and velocity (mm/s) In PTZ and treated zebrafish.

Figure 8A:
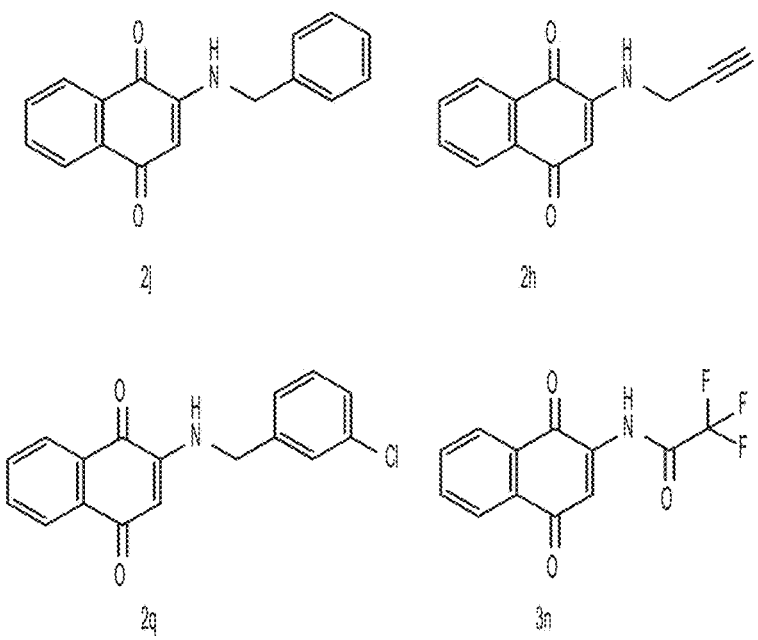
Figure 8B:
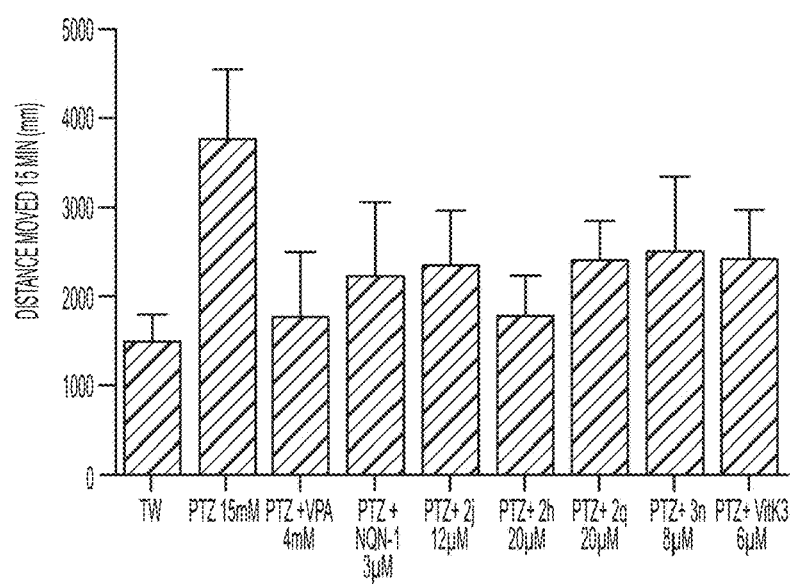

FIGS. 8A-B—VK$_3$ analogues significantly reduce seizure activity in 6 dpf zebrafish treated with PTZ to induce seizures. FIG. 8A. Structures of VK analogs FIG. 8B. and their activities against PTZ induced epileptic seizures in Zebrafish.

Figure 9:
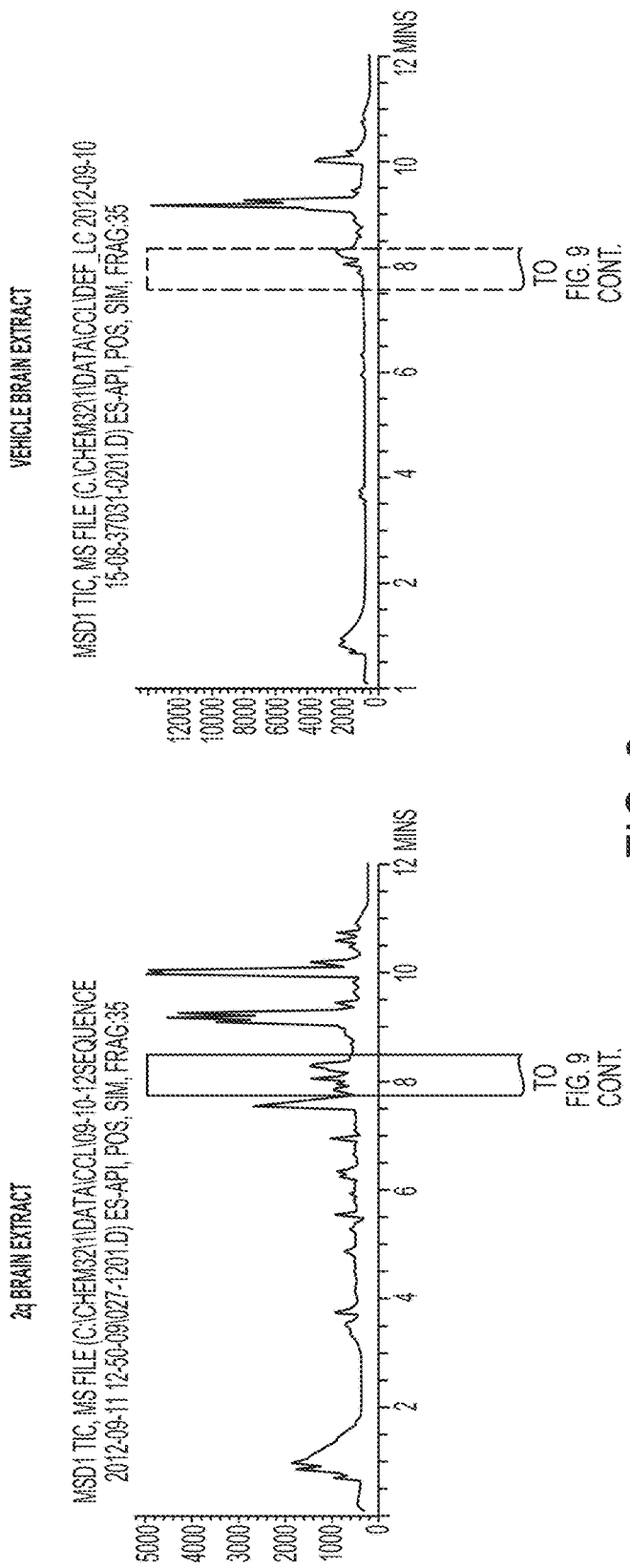
Figure 9:
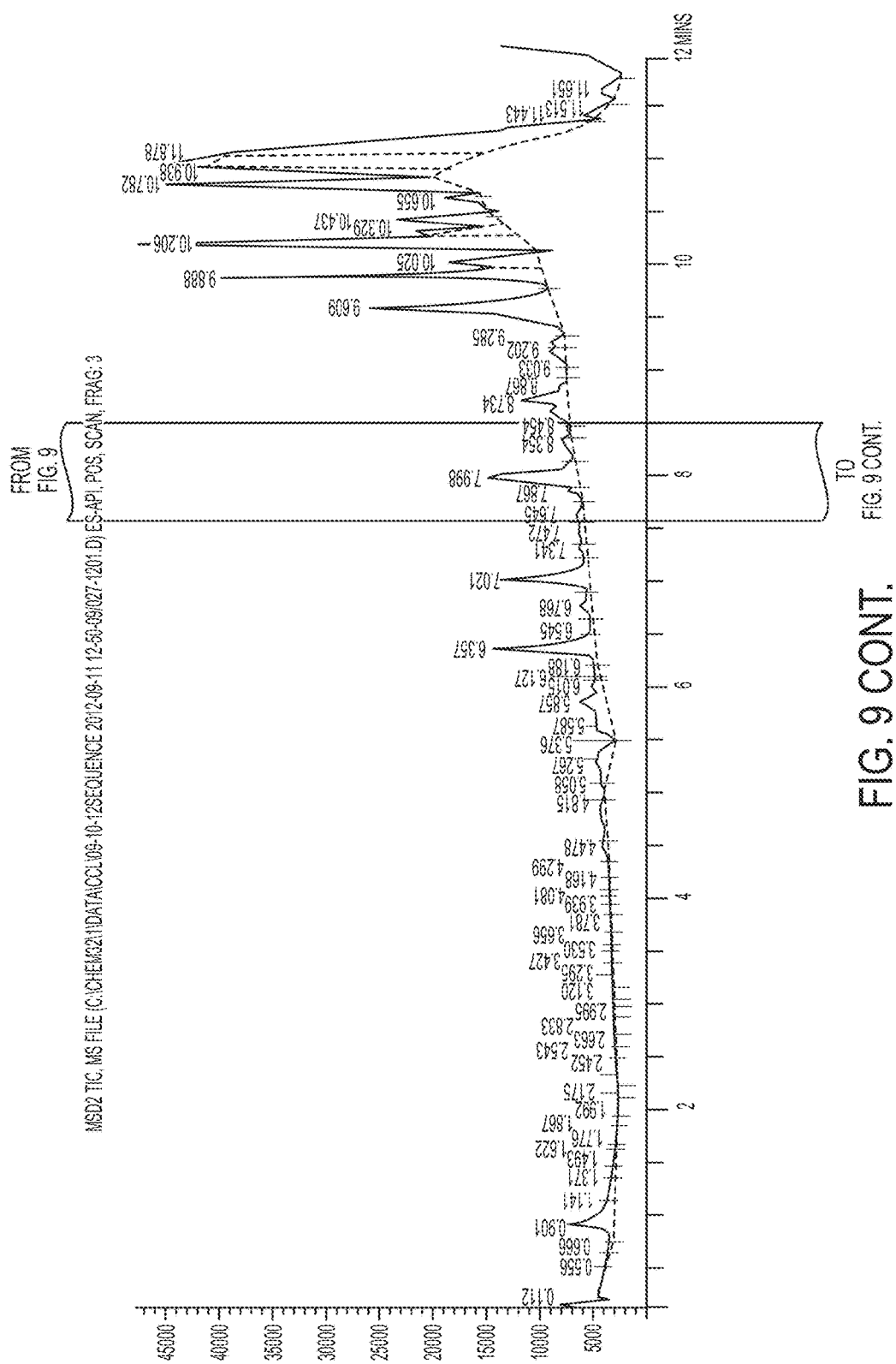
Figure 9:
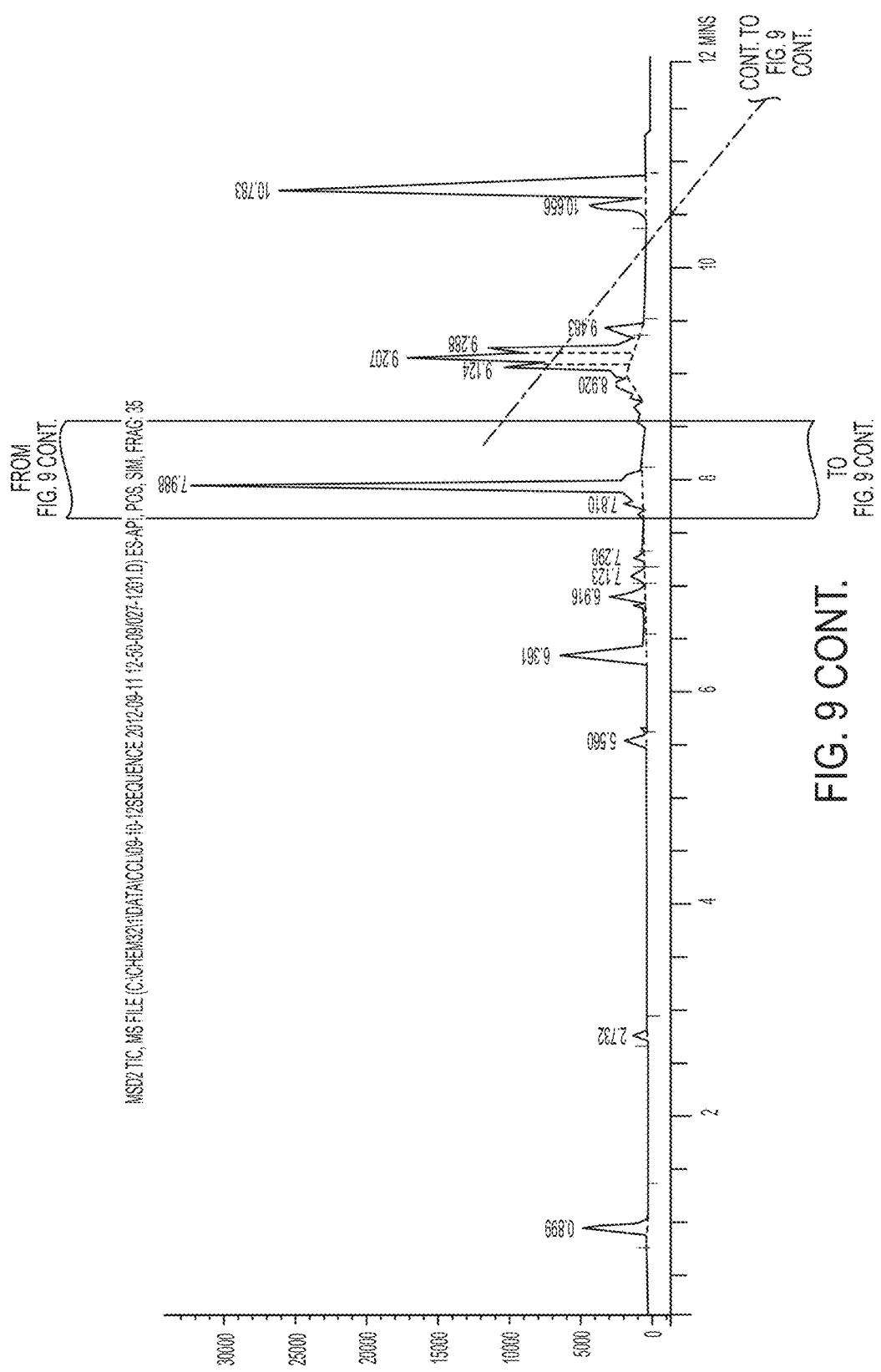
Figure 9:
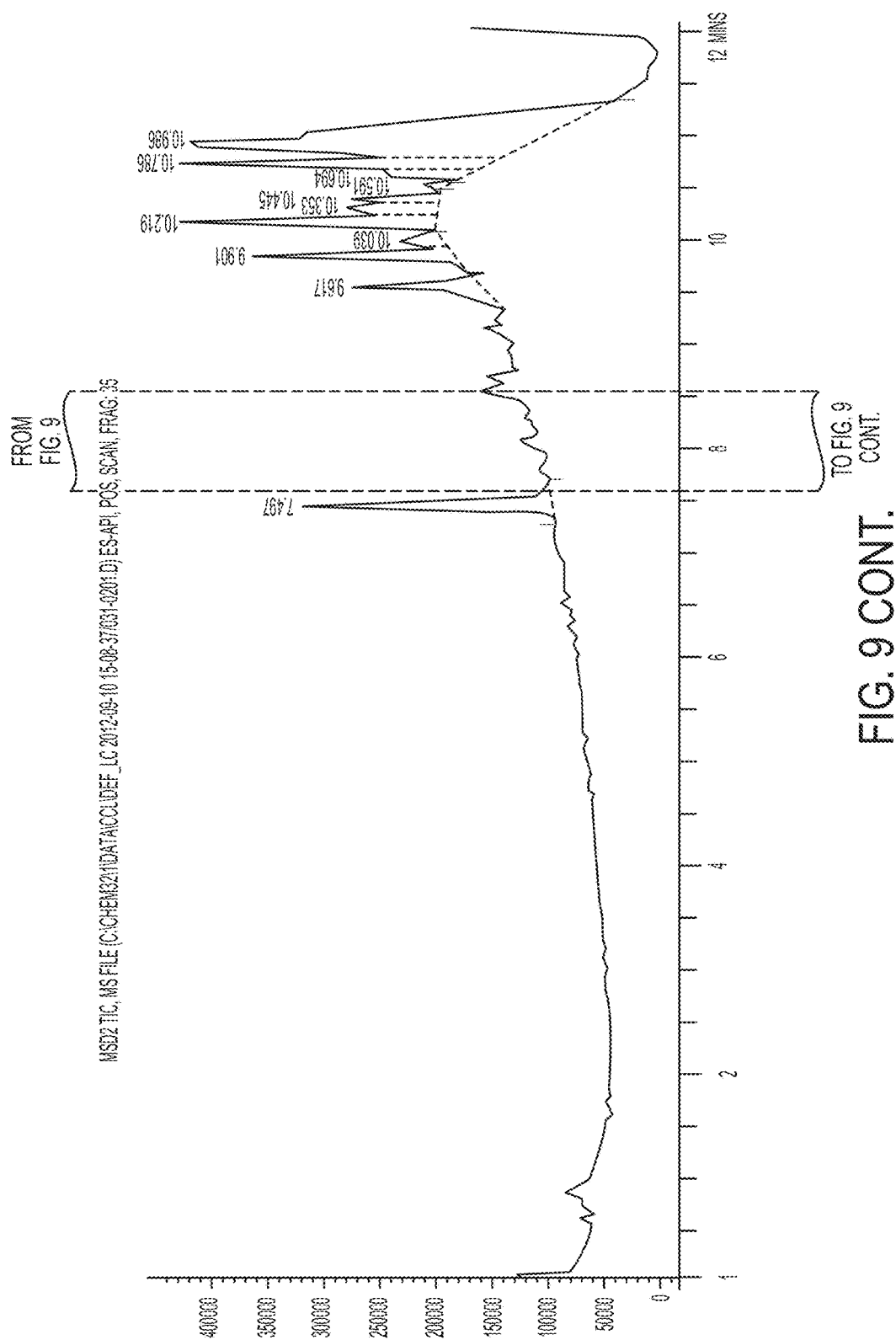
Figure 9:
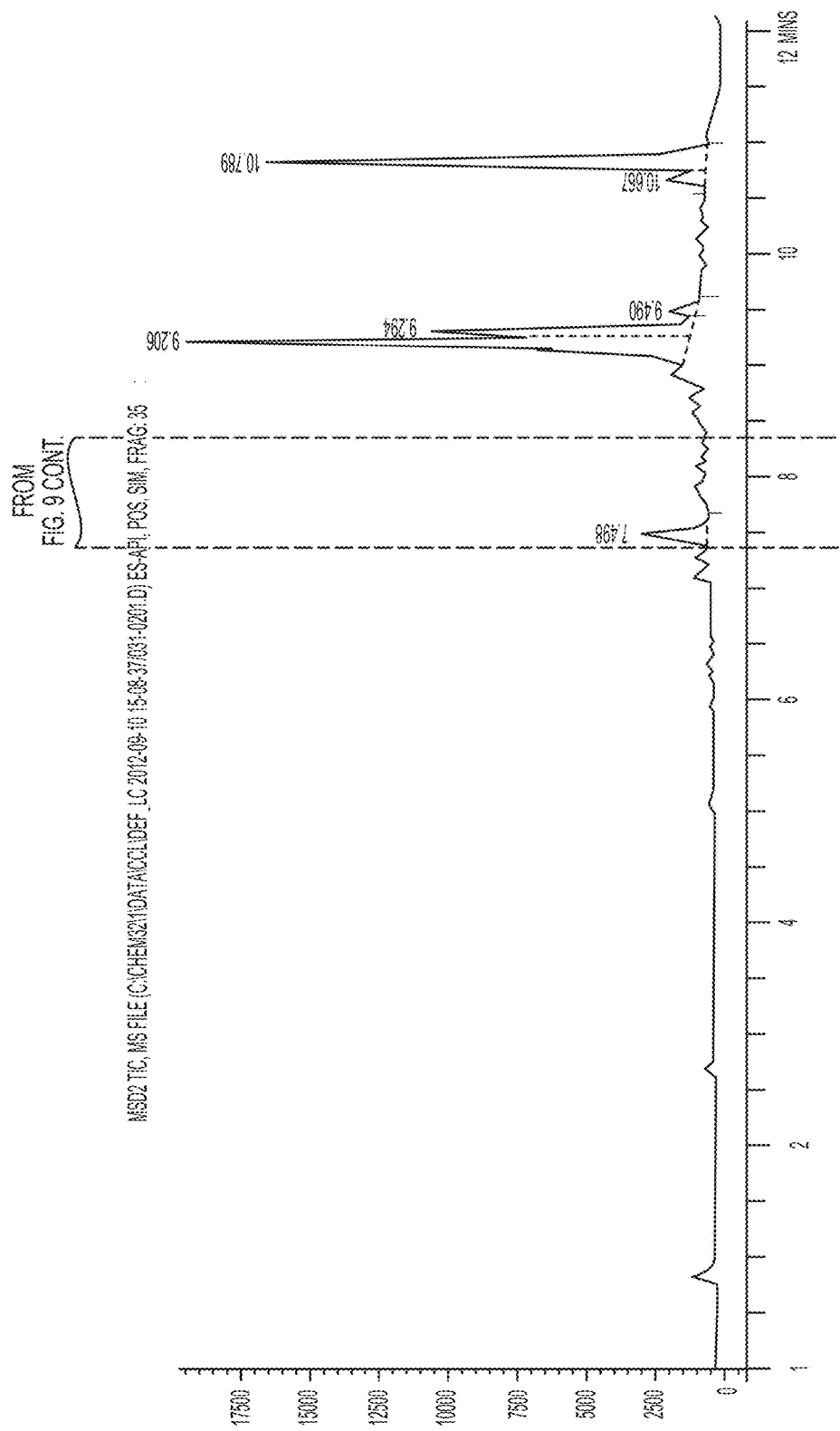
Figure 9:
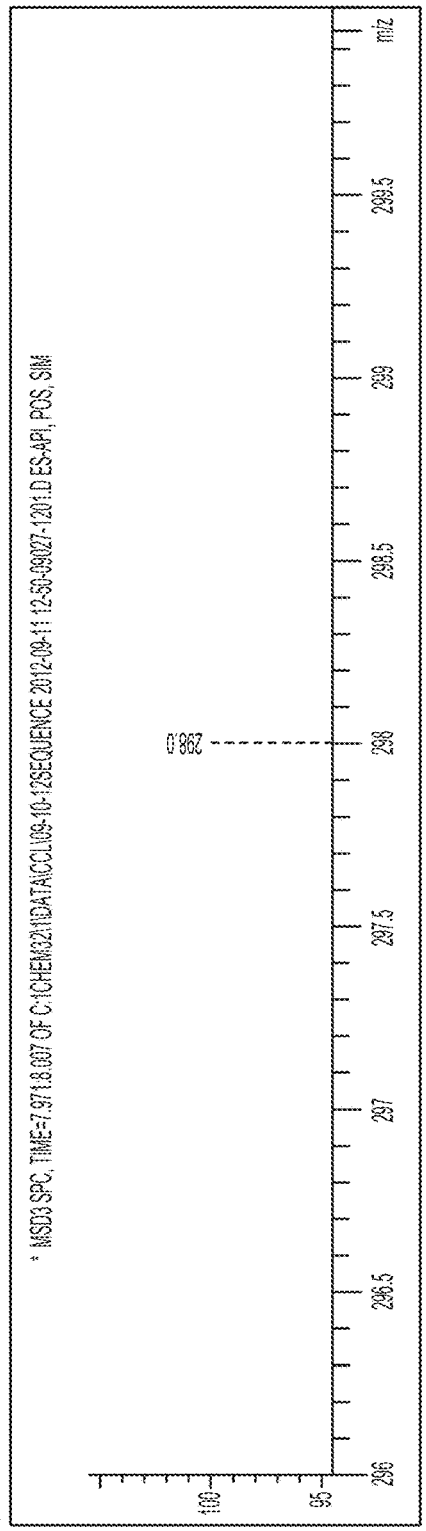

FIG. 9—VK analog, 2q, penetrates blood-brain barrier. Mice treated with 2q for 3 weeks and have brain analyzed 2 hrs after last injection. 2q is presented in 2q treated mice brain extract (left panel), but 2q is not observed in the vehicle treated mice brain extract (right panel). The expected mass and LC-retention time of 2q matches pure 2q standard under the same analytical conditions and mass spectrum setting.

Figure 10A:
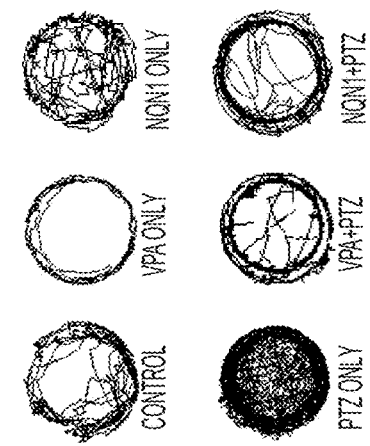
Figure 10C:
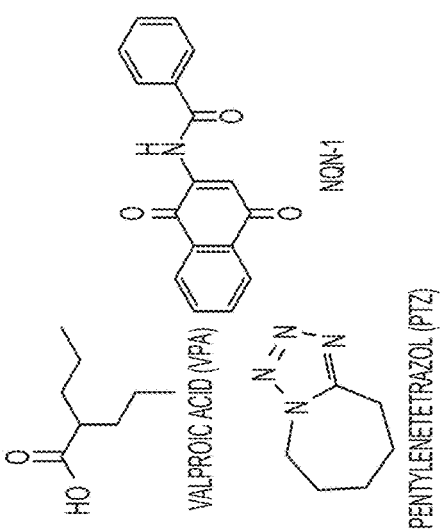
Figure 10B:
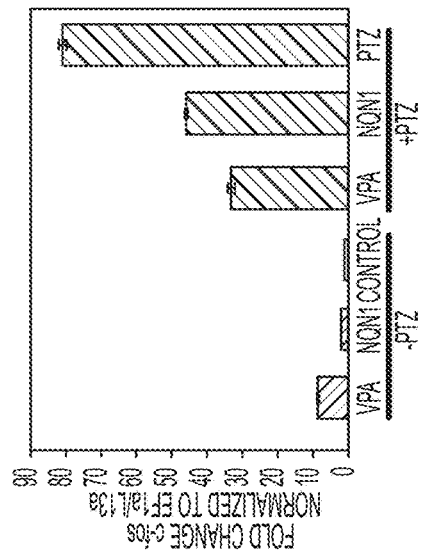
Figure 10D:
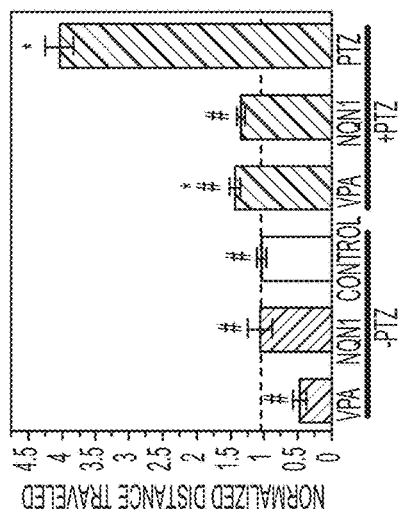

FIGS. 10A-10D—FIG. 10A. Chemical structures of pentylenetetrazol (PTZ), valproic acid (VPA) and NQN-1. FIG. 10B. Recording traces of zebrafish larval movement over 15 min for each compound with and without PTZ. FIG. 10C. Total mean distance traveled over the 15 min recording period normalized to control. Treatment of zebrafish larvae with VPA (4 mM) or NQN-1 (3 µM) alone did not induce any increase in swim activity. PTZ significantly increases the distance traveled compared to control (*p<0.05 compared to control). Pretreatment of zebrafish larvae with VPA or NQN-1 significantly reduced PTZ-induced swim activity (# p<0.05 compared to PTZ). Mean distance traveled +/−SEM are shown, n=23-25. FIG. 10D. Fold change of c-fos gene expression in treated zebrafish larvae. PTZ treatment increases c-fos gene expression 80-fold over control. Pretreatment with VPA or NQN-1 blunt this increase and treatment of these compounds alone does not induce dramatic changes in c-fos expression. Fold change is plotted with SEM (n=2).

Figure 11A:
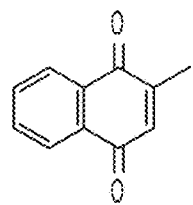
Figure 11B:
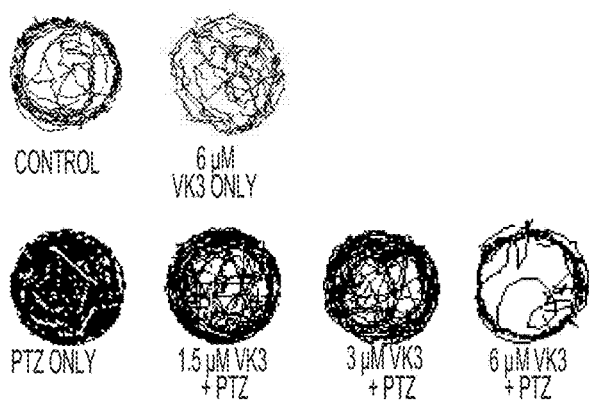
Figure 11C:
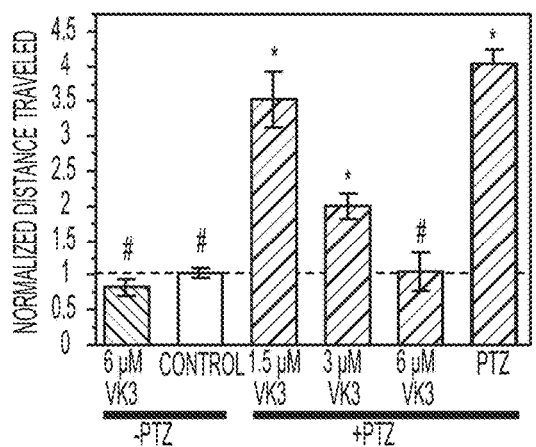
Figure 11D:
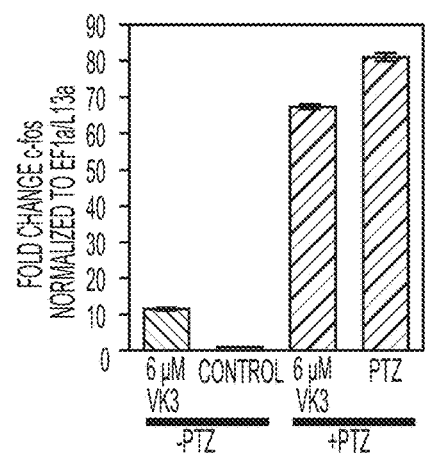

FIGS. 11A-11D—FIG. 11A. Structure of VK3. FIG. 11B. Recording traces of zebrafish larval movement over 15 min for VK3 with and without PTZ. FIG. 11C. Dose-dependent response of VK3 against PTZ-induced swim activity. Total mean distance traveled over the 15 min recording period. Zebrafish pretreated with VK3 prior to PTZ had a dose-dependent reduction in movement. 1.5 µM and 3 µM VK3 did not significantly reduce swim distance compared to PTZ and values remained significantly different from control (*p<0.05 compared to control). 6 uM VK3 significantly reduced distance traveled compared to PTZ (# p<0.05 compared to PTZ). Treatment of VK3 alone had no effect on swim distance. Mean distance traveled +/−SEM are shown, n=8 for each group. FIG. 11D. Fold change of c-fos gene expression in treated zebrafish larvae. PTZ treatment increases c-fos gene expression 80-fold over control. Pretreatment with 6 µM VK3 blunts this increase in c-fos and treatment of VK3 alone did not induce dramatic changes in c-fos expression. Fold change is plotted with SEM (n=2).

Figure 12A:
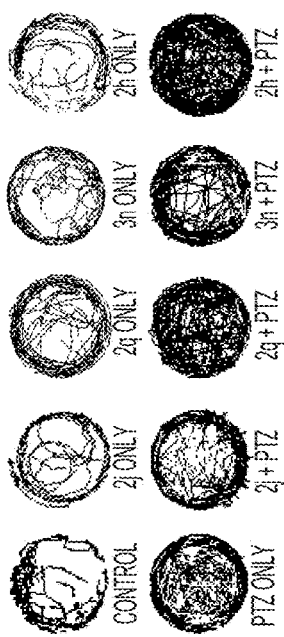
Figure 12B:
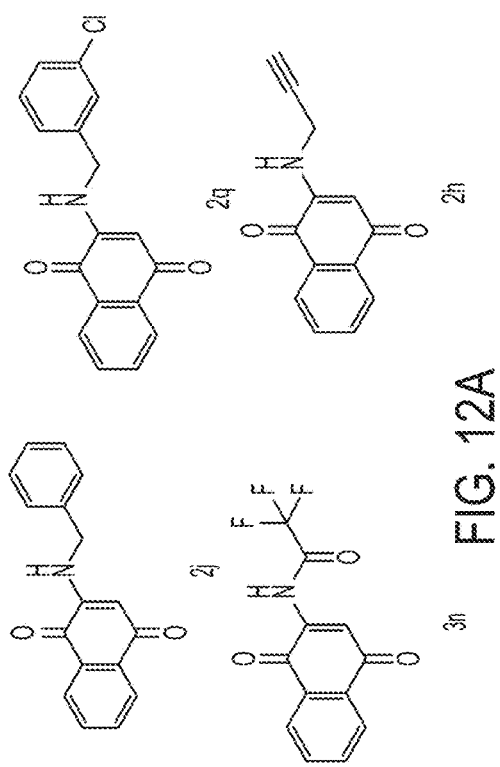
Figure 12C:
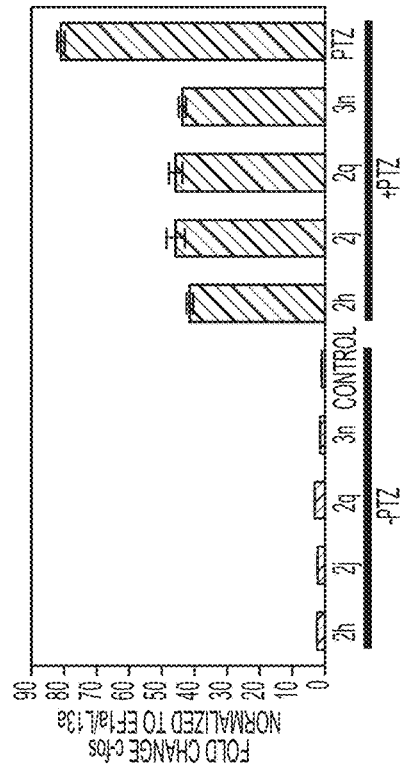
Figure 12D:
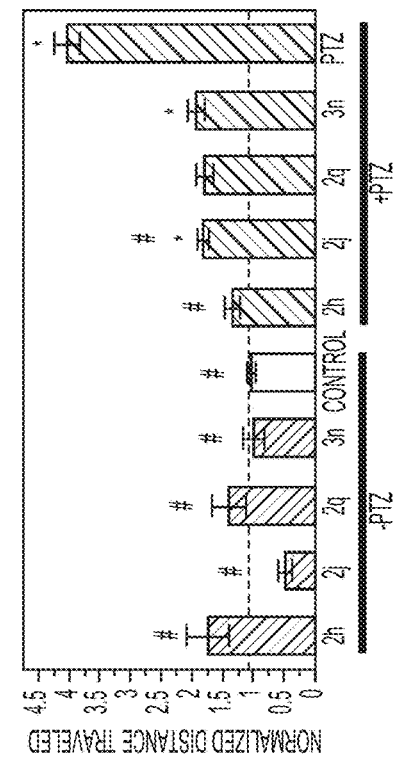

FIGS. 12A-12D—FIG. 12A. Structures of Vitamin K analogs that reduce PTZ-induced seizure activity in zebrafish. FIG. 12B. Recording traces of zebrafish larval movement over 15 min for all compounds with and without PTZ. FIG. 12C. Pre-treatment with Vitamin K analogs 2j (10 µM) and 2 h (20 µM) significantly reduced swim activity from PTZ only levels (# p<0.05 compared to PTZ). Compound 2q (20 uM) reduced swim levels but was not significantly different from PTZ. Compound 3n (8 µM) also reduced swim activity but to a level different from control but not from PTZ alone (*p<0.05 compared to control). Treatment of compounds in the absence of PTZ did not increase swim activity. Mean distance traveled +/−SEM are shown, n=8-40. FIG. 12D. Fold change of c-fos gene expression in treated zebrafish larvae. PTZ treatment increases c-fos gene expression 80-fold over control. Pretreatment with 2j, 2 h, 2q or 3n blunt this increase and treatment of compounds alone did not induce dramatic changes in c-fos expression. Fold change is plotted with SEM (n=2).

Figure 13A:
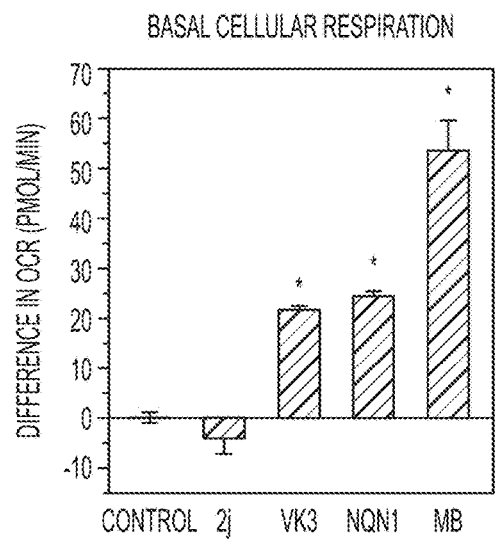
Figure 13B:
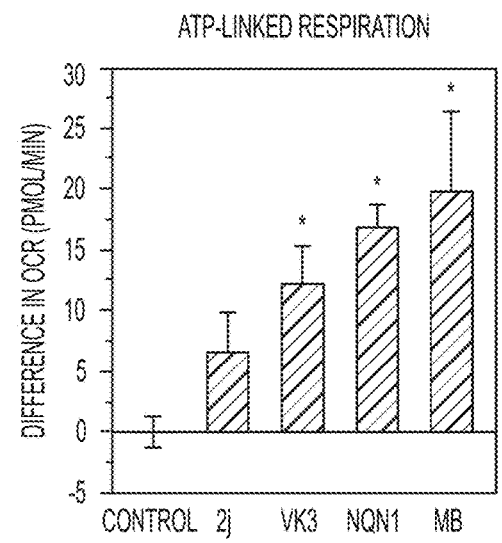
Figure 13C:
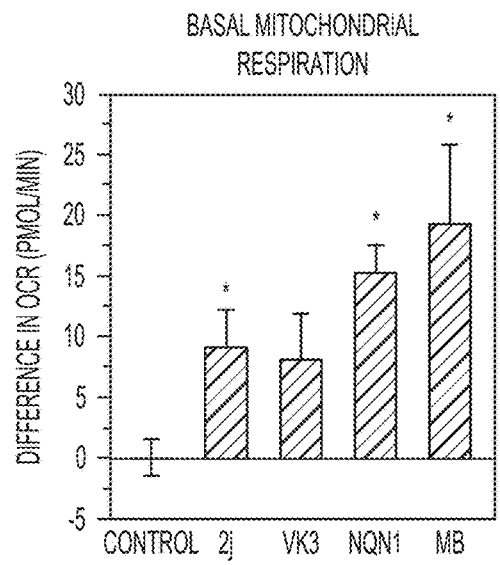
Figure 13D:
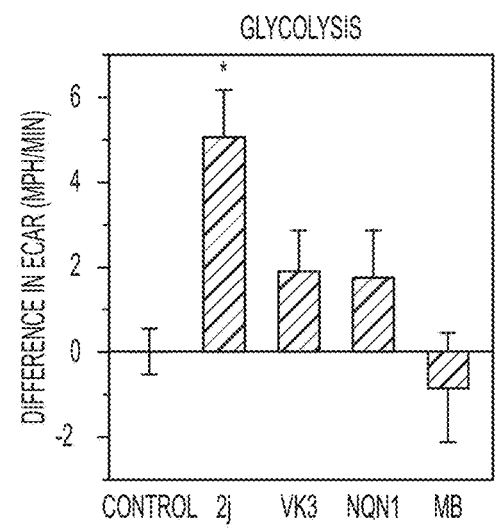

FIGS. 13A-13D—FIG. 13A. HT-22 neurons treated with 5 µM VK3, 5 µM NQN-1 or 12.5 µM MB showed significantly higher basal cellular respiration compared to control (measured as oxygen consumption rates, OCR) while VK3 analog 2j did not (*p<0.05). FIG. 13 B. ATP-linked respiration was significantly increased after treatment with VK3, NQN-1, or MB (*p<0.05). FIG. 13C. Basal mitochondrial respiration was significantly increased after treatment with 2j, NQN-1 or MB but not VK3 (*p<0.05). FIG. 13D. Glycolysis, as measured as media acidification (ECAR), did not change for VK3, NQN1 or MB but 2j showed significantly increased ECAR compared to control (*p<0.05). The OCR and ECAR levels are given as differences from the mean values +/−SEM, n=18-79.

Figure 14:
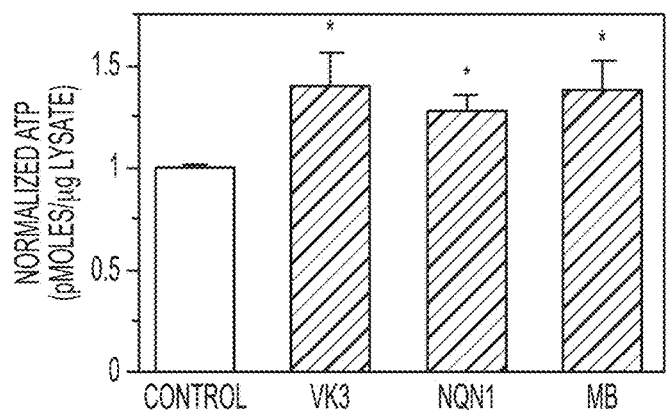

FIG. 14—Total ATP levels in pmol/µg lysate in HT-22 neurons treated with VK3, NQN-1 or MB. VK3, NQN-1 and MB significantly increase ATP levels from control (*p<0.05). Mean values (relative to control values) are plotted +/−SEM, n=7-13.

Figure 15:
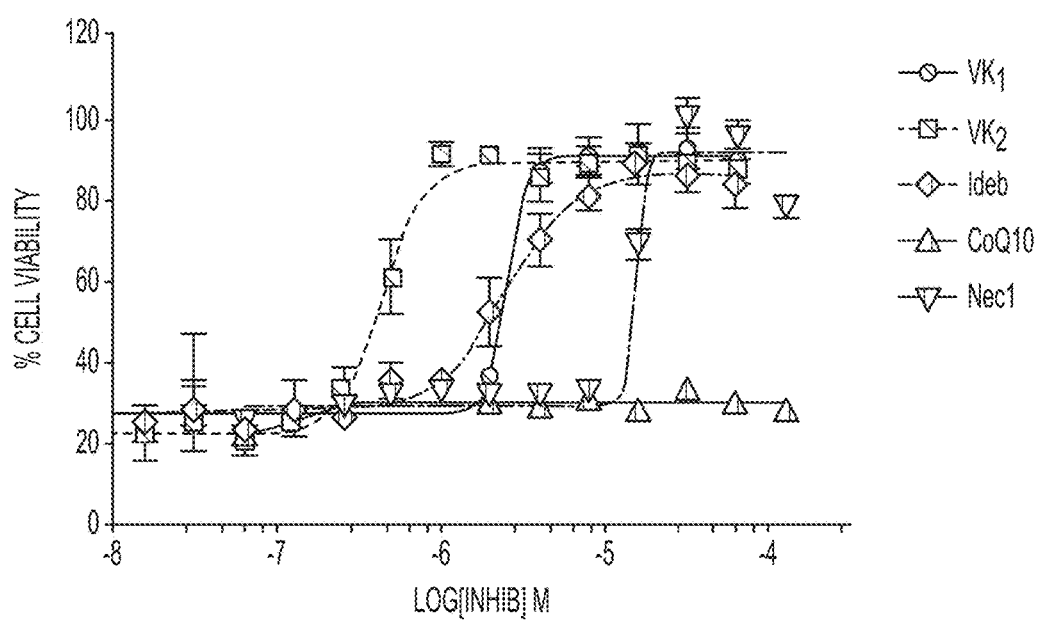

FIG. 15—Dose-response curves of Vitamin K1, Vitamin K2, and control compounds Necrostatin-1, Idebenone, Coenzyme Q10, and Trolox. Cell viability assay was conducted as described in the Methods sections of the main text.

FIG. 16—Scaffold optimization and cell viability assay results. Cell viability assay was conducted as described in the Experimental Methods sections.

Figure 17:
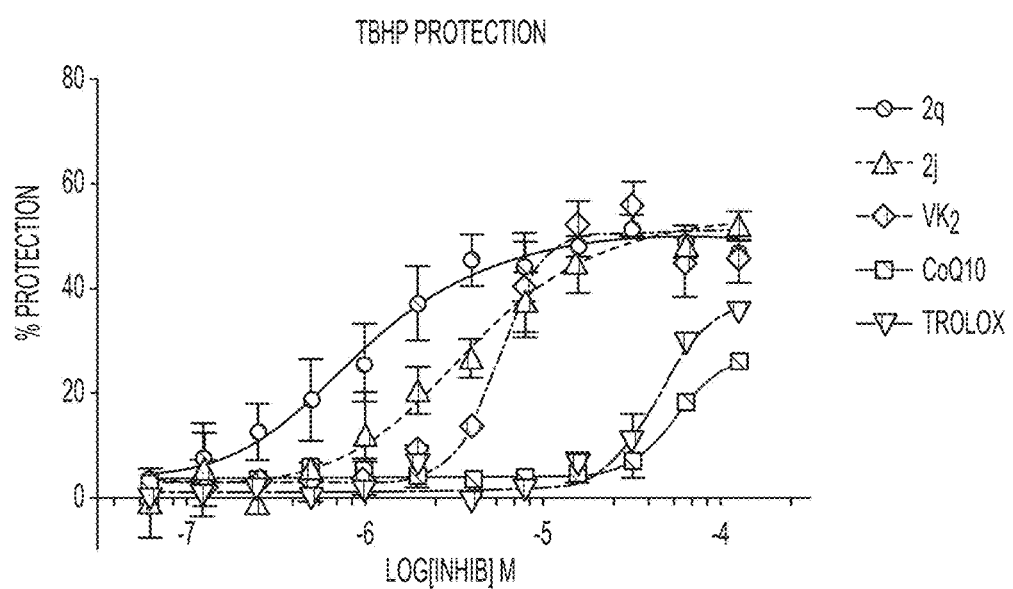

FIG. 17—t-BuOOH protection results. Cell viability assay was conducted as described in the Experimental Methods sections.

Figure 18A:
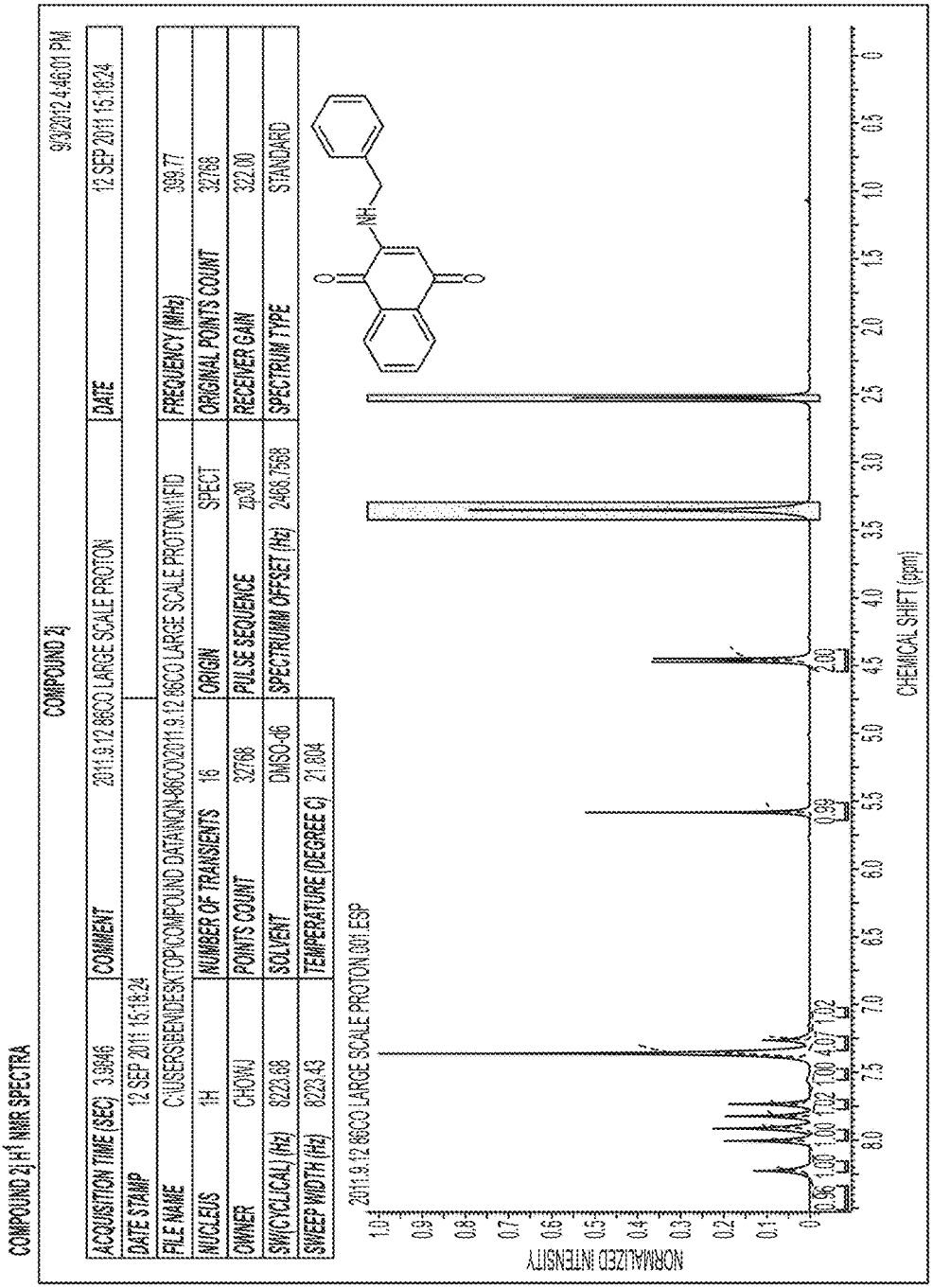
Figure 18B:
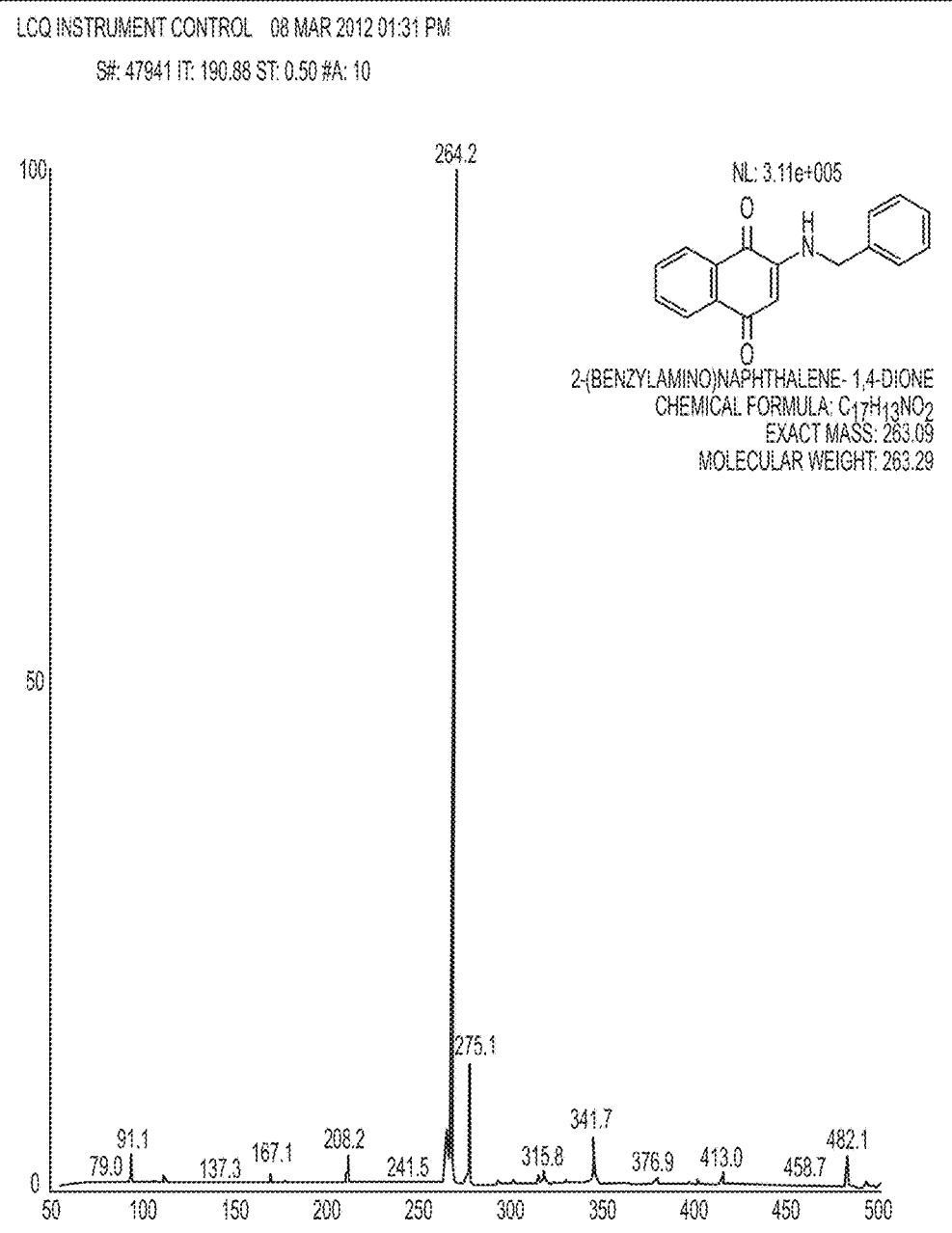
Figure 18C:
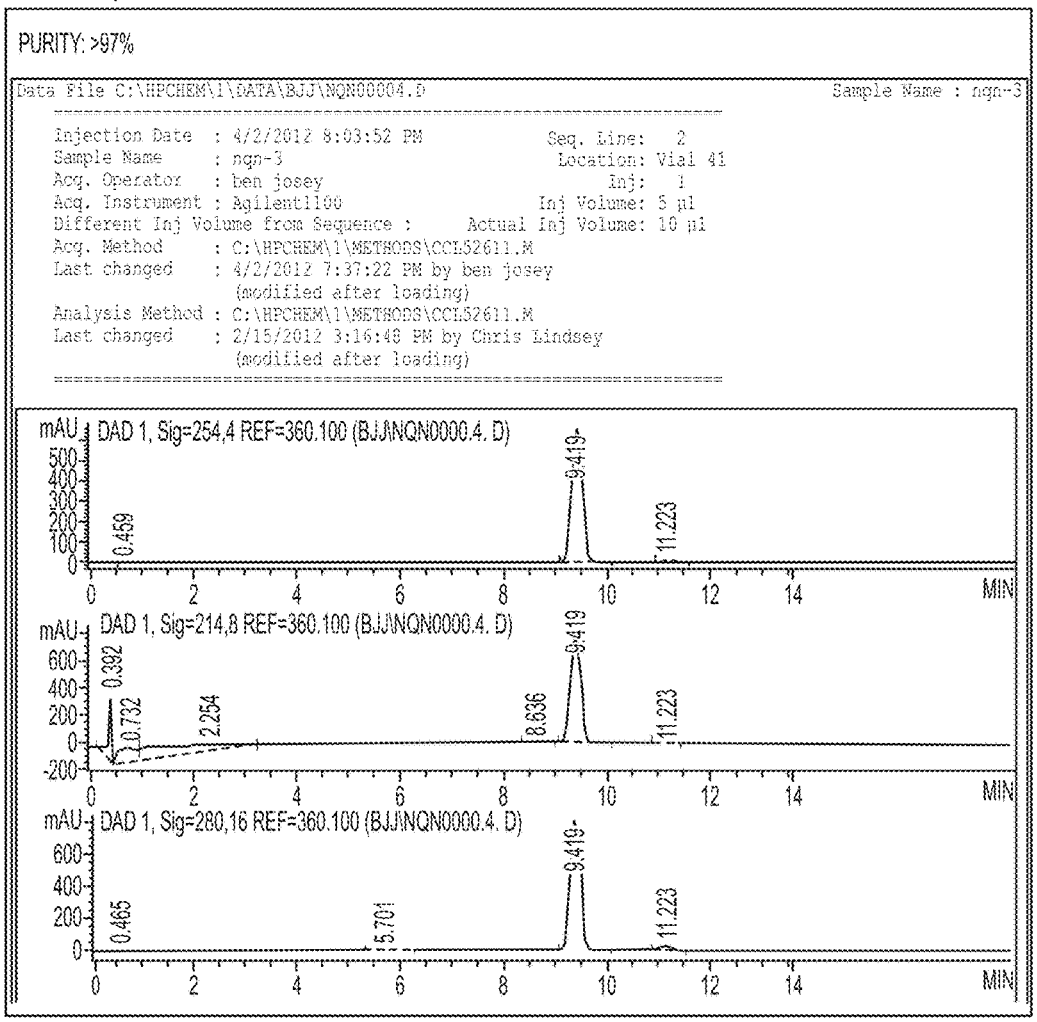

FIGS. 18A-18C—Analytical Characterization of Compound 2j. FIG. 18A, $^1$NMR Spectra. FIG. 18B, Mass Spectra. FIG. 18C, Analytical HPLC traces at 214, 254, and 280 nm.

Figure 19A:
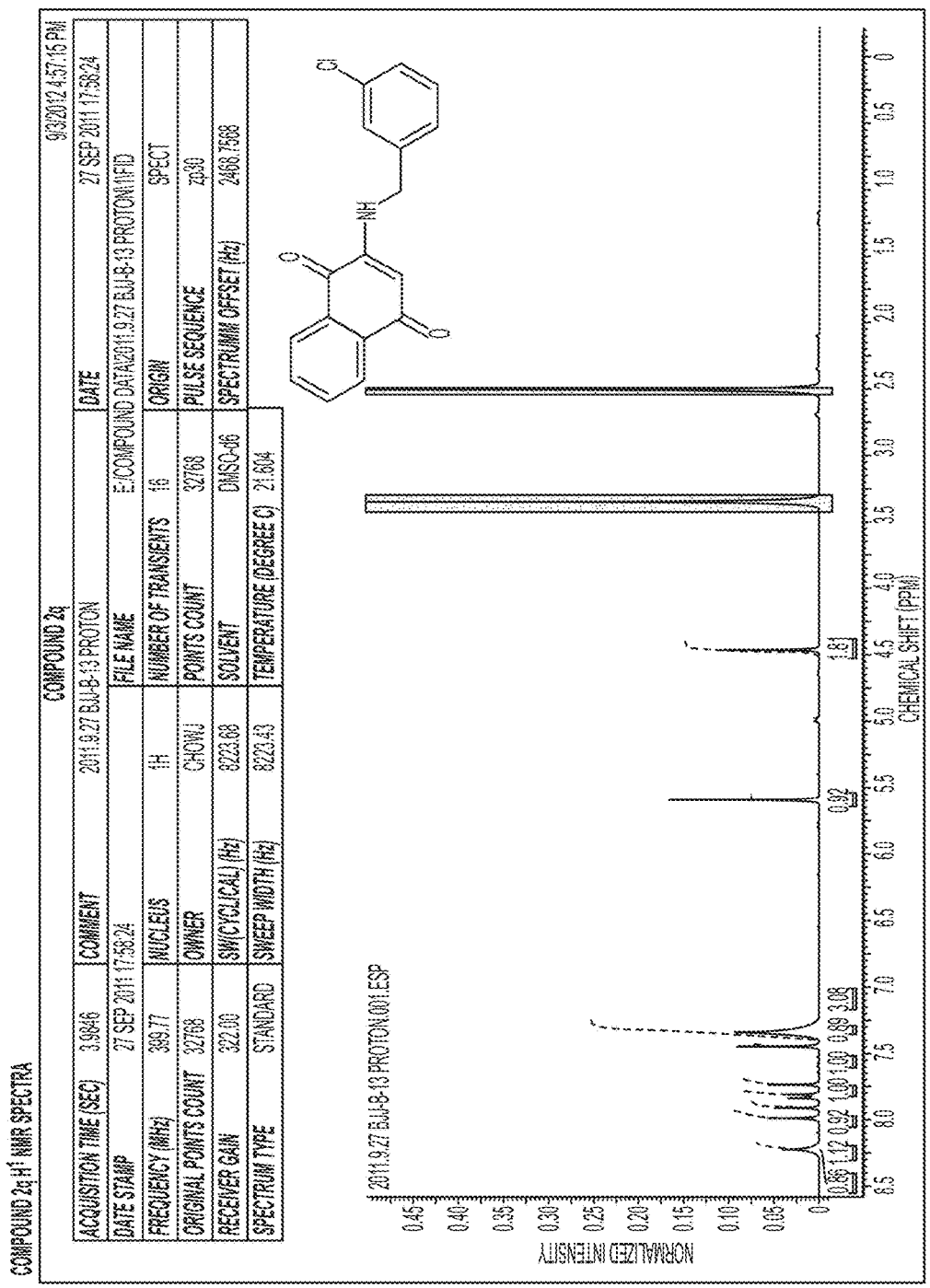
Figure 19B:
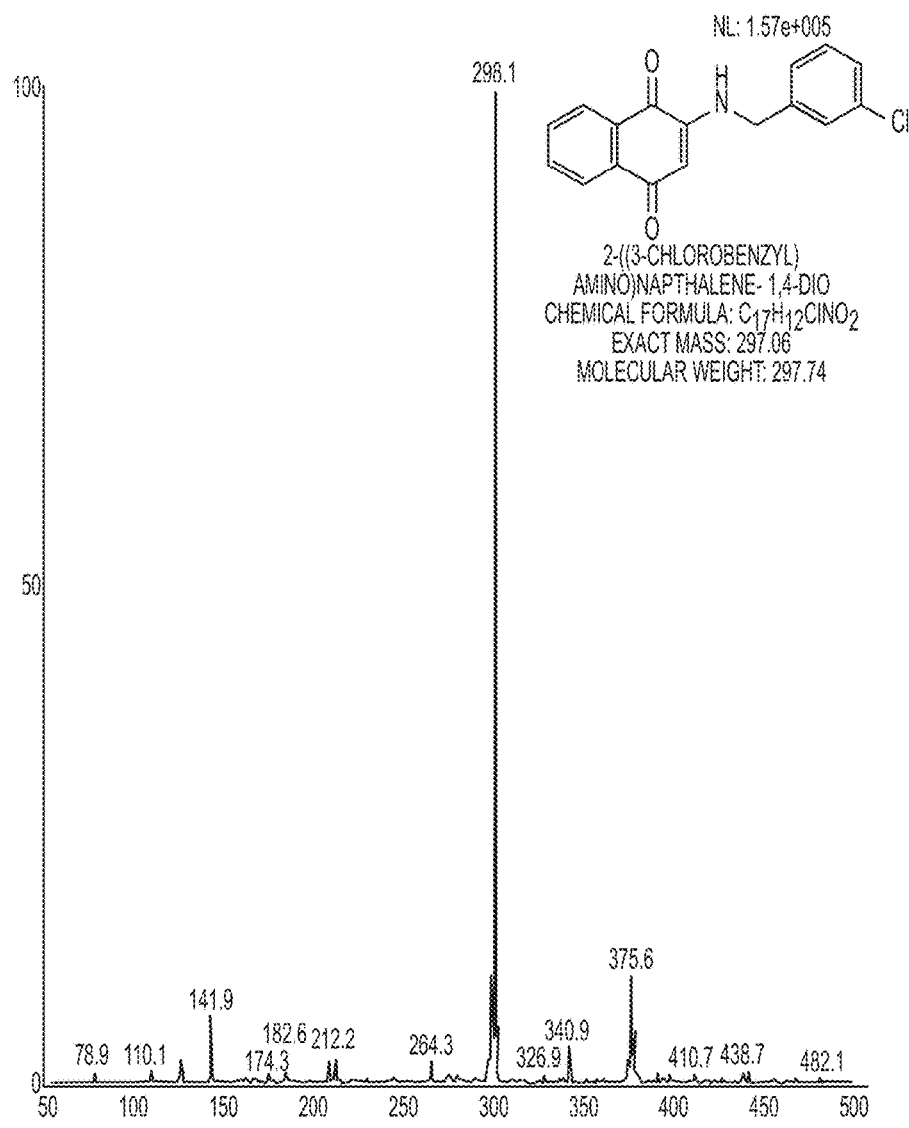
Figure 19C:
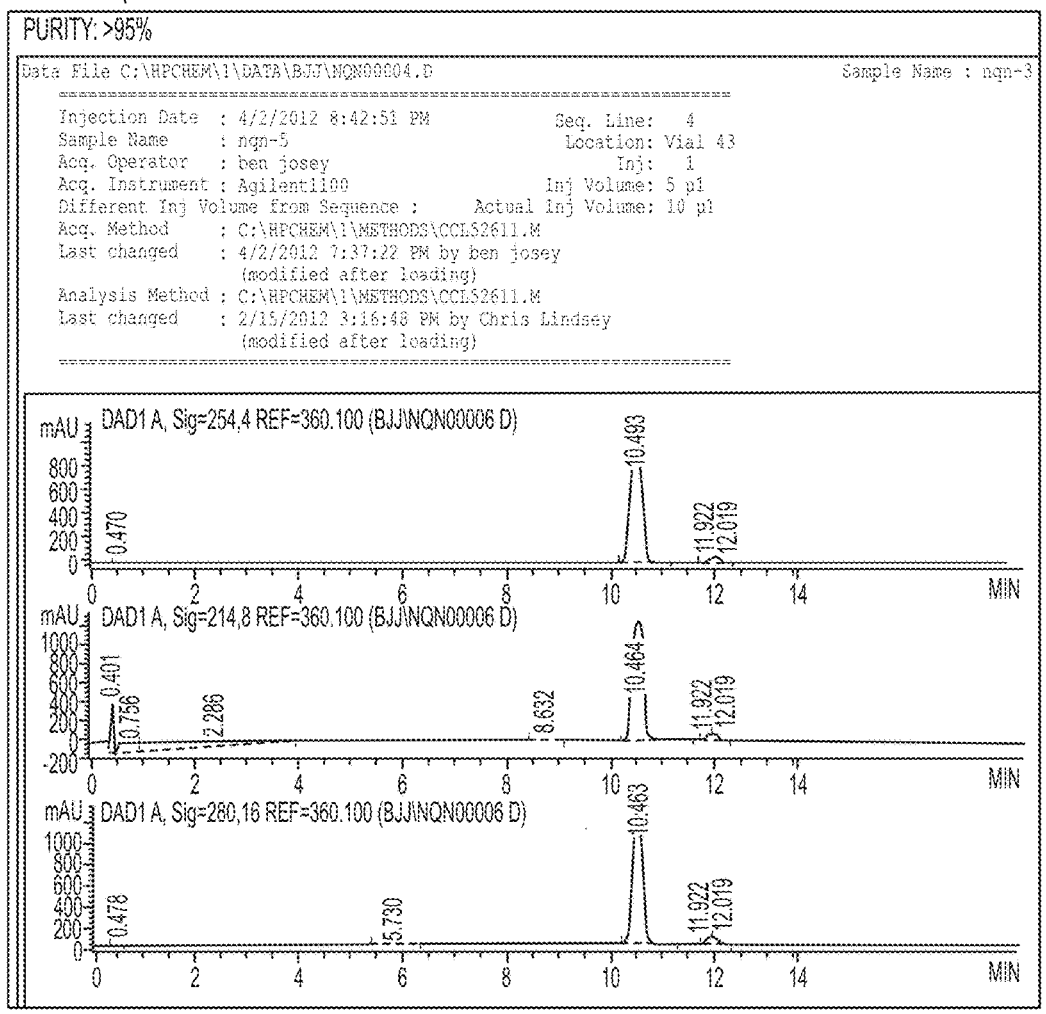

FIGS. 19A-19C—Analytical Characterization of Compound 2q. FIG. 19A, $^1$NMR Spectra. FIG. 19B, Mass Spectra. FIG. 19C, Analytical HPLC traces at 214, 254, and 280 nm.

DESCRIPTION OF ILLUSTRATIVE EMBODIMENTS

I. Definitions

As used herein, the term "amino" means —NH$_2$; the term "nitro" means —NO$_2$; the term "halo" designates —F, —Cl, —Br or —I; the term "mercapto" means —SH; the term "cyano" means —CN; the term "silyl" means —SiH$_3$, and the term "hydroxy" means —OH.

The term "heteroatom-substituted," when used to modify a class of organic radicals (e.g., alkyl, aryl, acyl, etc.), means that one, or more than one, hydrogen atom of that radical has been replaced by a heteroatom, or a heteroatom containing group. Examples of heteroatoms and heteroatom containing groups include: hydroxy, cyano, alkoxy, =O, =S, —NO$_2$, —N(CH$_3$)$_2$, amino, or —SH. Specific heteroatom-substituted organic radicals are defined more fully below.

The term "heteroatom-unsubstituted," when used to modify a class of organic radicals (e.g., alkyl, aryl, acyl, etc.) means that none of the hydrogen atoms of that radical have been replaced with a heteroatom or a heteroatom containing group. Substitution of a hydrogen atom with a carbon atom, or a group consisting of only carbon and hydrogen atoms, is not sufficient to make a group heteroatom-substituted. For example, the group —$C_6H_4C\equiv CH$ is an example of a heteroatom-unsubstituted aryl group, while —$C_6H_4F$ is an example of a heteroatom-substituted aryl group. Specific heteroatom-unsubstituted organic radicals are defined more fully below.

The term "heteroatom-unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The term "alkyl" includes straight-chain alkyl groups, branched-chain alkyl groups, cycloalkyl (alicyclic) groups, alkyl heteroatom-substituted cycloalkyl groups, and cycloalkyl heteroatom-substituted alkyl groups. The groups, —$CH_3$, —$CH_2CH_3$, —$CH_2CH_2CH_3$, —$CH(CH_3)_2$, —$CH(CH_2)_2$ (cyclopropyl), —$CH_2CH_2CH_2CH_3$, —$CH(CH_3)CH_2CH_3$, —$CH_2CH(CH_3)_2$, —$C(CH_3)_3$, —$CH_2C(CH_3)_3$, cyclobutyl, cyclopentyl, and cyclohexyl, are all examples of heteroatom-unsubstituted alkyl groups.

The term "heteroatom-substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all examples of heteroatom-substituted alkyl groups: trifluoromethyl, —$CH_2F$, —$CH_2Cl$, —$CH_2Br$, —$CH_2OH$, —$CH_2OCH_3$, —$CH_2OCH_2CH_3$, —$CH_2OCH_2CH_2CH_3$, —$CH_2OCH(CH_3)_2$, —$CH_2OCH(CH_2)_2$, —$CH_2OCH_2CF_3$, —$CH_2OCOCH_3$, —$CH_2NH_2$, —$CH_2NHCH_3$, —$CH_2N(CH_3)_2$, —$CH_2NHCH_2CH_3$, —$CH_2N(CH_3)CH_2CH_3$, —$CH_2NHCH_2CH_2CH_3$, —$CH_2NHCH(CH_3)_2$, —$CH_2NHCH(CH_2)_2$, —$CH_2N(CH_2CH_3)_2$, —$CH_2CH_2F$, —$CH_2CH_2Cl$, —$CH_2CH_2Br$, —$CH_2CH_2I$, —$CH_2CH_2OH$, —$CH_2CH_2OCOCH_3$, —$CH_2CH_2NH_2$, —$CH_2CH_2N(CH_3)_2$, —$CH_2CH_2NHCH_2CH_3$, —$CH_2CH_2N(CH_3)CH_2CH_3$, —$CH_2CH_2NHCH_2CH_2CH_3$, —$CH_2CH_2NHCH(CH_3)_2$, —$CH_2CH_2NHCH(CH_2)_2$, —$CH_2CH_2N(CH_2CH_3)_2$, —$CH_2CH_2NHCO_2C(CH_3)_3$, and —$CH_2Si(CH_3)_3$.

The term "heteroatom-unsubstituted $C_n$-alkenyl" refers to a radical, having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted $C_2$-$C_{10}$-alkenyl has 2 to 10 carbon atoms. Heteroatom-unsubstituted alkenyl groups include: —$CH=CH_2$, —$CH=CHCH_3$, —$CH=CHCH_2CH_3$, —$CH=CHCH_2CH_2CH_3$, —$CH=CHCH(CH_3)_2$, —$CH=CHCH(CH_2)_2$, —$CH_2CH=CH_2$, —$CH_2CH=CHCH_3$, —$CH_2CH=CHCH_2CH_3$, —$CH_2CH=CHCH_2CH_2CH_3$, —$CH_2CH=CHCH(CH_3)_2$, —$CH_2CH=CHCH(CH_2)_2$, and —$CH=CH$—$C_6H_5$.

The term "heteroatom-substituted $C_n$-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkenyl has 2 to 10 carbon atoms. The groups, —$CH=CHF$, —$CH=CHCl$ and —$CH=CHBr$, are examples of heteroatom-substituted alkenyl groups.

The term "heteroatom-unsubstituted $C_n$-alkynyl" refers to a radical, having a linear or branched, cyclic or acyclic structure, further having at least one carbon-carbon triple bond, a total of n carbon atoms, at least one hydrogen atom, and no heteroatoms. For example, a heteroatom-unsubstituted $C_2$-$C_{10}$-alkynyl has 2 to 10 carbon atoms. The groups, —$C\equiv CH$, —$C\equiv CCH_3$, and —$C\equiv CC_6H_5$ are examples of heteroatom-unsubstituted alkynyl groups.

The term "heteroatom-substituted $C_n$-alkynyl" refers to a radical, having a single nonaromatic carbon atom as the point of attachment and at least one carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkynyl has 2 to 10 carbon atoms. The group, —$C\equiv CSi(CH_3)_3$, is an example of a heteroatom-substituted alkynyl group.

The term "heteroatom-unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted $C_6$-$C_{10}$-aryl has 6 to 10 carbon atoms. Examples of heteroatom-unsubstituted aryl groups include phenyl, methylphenyl, (dimethyl)phenyl, —$C_6H_4CH_2CH_3$, —$C_6H_4CH_2CH_2CH_3$, —$C_6H_4CH(CH_3)_2$, —$C_6H_4CH(CH_2)_2$, —$C_6H_3(CH_3)CH_2CH_3$, —$C_6H_4CH=CH_2$, —$C_6H_4CH=CHCH_3$, —$C_6H_4C\equiv CH$, —$C_6H_4C\equiv CCH_3$, naphthyl, and the radical derived from biphenyl. The term "heteroatom-unsubstituted aryl" includes carbocyclic aryl groups, biaryl groups, and radicals derived from polycyclic fused hydrocarbons (PAHs).

The term "heteroatom-substituted $C_n$-aryl" refers to a radical, refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-heteroaryl has 1 to 10 carbon atoms. The term "heteroatom-substituted aryl" includes heteroaryl and heterocyclic aryl groups. It also includes those groups derived from the compounds: pyrrole, furan, thiophene, imidazole, oxazole, isoxazole, thiazole, isothiazole, triazole, pyrazole, pyridine, pyrazine, pyridazine, pyrimidine, and the like. Further examples of heteroatom-substituted aryl groups include the groups: —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OCOCH_3$, —$C_6H_4OC_6H_5$, —$C_6H_4NH_2$, —$C_6H_4NHCH_3$, —$C_6H_4NHCH_2CH_3$, —$C_6H_4CH_2Cl$, —$C_6H_4CH_2Br$, —$C_6H_4CH_2OH$, —$C_6H_4CH_2OCOCH_3$, —$C_6H_4CH_2NH_2$, —$C_6H_4N(CH_3)_2$, —$C_6H_4CH_2CH_2Cl$, —$C_6H_4CH_2CH_2OH$, —$C_6H_4CH_2CH_2OCOCH_3$, —$C_6H_4CH_2CH_2NH_2$, —$C_6H_4CH_2CH=CH_2$, —$C_6H_4CF_3$, —$C_6H_4CN$, —$C_6H_4C\equiv CSi(CH_3)_3$, —$C_6H_4COH$, —$C_6H_4COCH_3$, —$C_6H_4COCH_2CH_3$, —$C_6H_4COCH_2CF_3$, —$C_6H_4COC_6H_5$, —$C_6H_4CO_2H$, —$C_6H_4CO_2CH_3$, —$C_6H_4CONH_2$, —$C_6H_4CONHCH_3$, —$C_6H_4CON(CH_3)_2$, furanyl, thienyl, pyridyl, pyrrolyl, pyrimidyl, pyrazinyl, and imidazoyl.

The term "heteroatom-unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted $C_7$-$C_{10}$-aralkyl has 7 to 10 carbon atoms. An "aralkyl" includes an alkyl heteroatom-substituted with an aryl group. Examples of heteroatom-unsubstituted aralkyls include phenylmethyl (benzyl) and phenylethyl.

The term "heteroatom-substituted $C_n$-aralkyl" refers to a radical, having a single saturated carbon atom as the point of attachment, further having a total of n carbon atoms, 0, 1, or more than one hydrogen atom, and at least one heteroatom, wherein at least one of the carbon atoms is incorporated an aromatic ring structures, further wherein each heteroatom is independently selected from the group consisting of N, O, F, Cl, Br, I, Si, P, and S. For example, a heteroatom-substituted $C_2$-$C_{10}$-heteroaralkyl has 2 to 10 carbon atoms.

The term "heteroatom-unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted $C_1$-$C_{10}$-acyl has 1 to 10 carbon atoms. The groups, —COH, —$COCH_3$, —$COCH_2CH_3$, —$COCH_2CH_2CH_3$, —$COCH(CH_3)_2$, —$COCH(CH_2)_2$, —$COC_6H_5$, —$COC_6H_4CH_3$, —$COC_6H_4CH_2CH_3$, —$COC_6H_4CH_2CH_2CH_3$, —$COC_6H_4CH(CH_3)_2$, —$COC_6H_4CH(CH_2)_2$, and —$COC_6H_3(CH_3)_2$, are examples of heteroatom-unsubstituted acyl groups.

The term "heteroatom-substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-acyl has 1 to 10 carbon atoms. The term heteroatom-substituted acyl includes carbamoyl, thiocarboxylate, and thiocarboxylic acid groups. The groups, —$COCH_2CF_3$, —$CO_2H$, —$CO_2CH_3$, —$CO_2CH_2CH_3$, —$CO_2CH_2CH_2CH_3$, —$CO_2CH(CH_3)_2$, —$CO_2CH(CH_2)_2$, —$CONH_2$, —$CONHCH_3$, —$CONHCH_2CH_3$, —$CONHCH_2CH_2CH_3$, —$CONHCH(CH_3)_2$, —$CONHCH(CH_2)_2$, —$CON(CH_3)_2$, —$CON(CH_2CH_3)CH_3$, —$CON(CH_2CH_3)_2$ and —$CONHCH_2CF_3$, are examples heteroatom-substituted acyl groups.

The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: —$OCH_3$, —$OCH_2CH_3$, —$OCH_2CH_2CH_3$, —$OCH(CH_3)_2$, and —$OCH(CH_2)_2$.

The term "heteroatom-substituted $C_n$-alkoxy" refers to a group, having the structure —OR, in which R is a heteroatom-substituted $C_n$-alkyl, as that term is defined above. For example, —$OCH_2CF_3$ is a heteroatom-substituted alkoxy group.

The term "heteroatom-unsubstituted $C_n$-alkenyloxy" refers to a group, having the structure —OR, in which R is a heteroatom-unsubstituted $C_n$-alkenyl, as that term is defined above.

The term "heteroatom-substituted $C_n$-alkenyloxy" refers to a group, having the structure —OR, in which R is a heteroatom-substituted $C_n$-alkenyl, as that term is defined above.

The term "heteroatom-unsubstituted $C_n$-alkynyloxy" refers to a group, having the structure —OR, in which R is a heteroatom-unsubstituted $C_n$-alkynyl, as that term is defined above.

The term "heteroatom-substituted $C_n$-alkynyloxy" refers to a group, having the structure —OR, in which R is a heteroatom-substituted $C_n$-alkynyl, as that term is defined above.

The term "heteroatom-unsubstituted $C_n$-aryloxy" refers to a group, having the structure —OAr, in which Ar is a heteroatom-unsubstituted $C_n$-aryl, as that term is defined above. An example of a heteroatom-unsubstituted aryloxy group is —$OC_6H_5$.

The term "heteroatom-substituted $C_n$-aryloxy" refers to a group, having the structure —OAr, in which Ar is a heteroatom-substituted $C_n$-aryl, as that term is defined above.

The term "heteroatom-unsubstituted $C_n$-aralkyloxy" refers to a group, having the structure —OAr, in which Ar is a heteroatom-unsubstituted $C_n$-aralkyl, as that term is defined above.

The term "heteroatom-substituted $C_n$-aralkyloxy" refers to a group, having the structure —OAr, in which Ar is a heteroatom-substituted $C_n$-aralkyl, as that term is defined above.

The term "heteroatom-unsubstituted $C_n$-acyloxy" refers to a group, having the structure —OAc, in which Ac is a heteroatom-unsubstituted $C_n$-acyl, as that term is defined above. A heteroatom-unsubstituted acyloxy group includes alkylcarbonyloxy and arylcarbonyloxy groups. For example, —$OCOCH_3$ is an example of a heteroatom-unsubstituted acyloxy group.

The term "heteroatom-substituted $C_n$-acyloxy" refers to a group, having the structure —OAc, in which Ac is a heteroatom-substituted $C_n$-acyl, as that term is defined above. A heteroatom-substituted acyloxy group includes alkoxycarbonyloxy, aryloxycarbonyloxy, carboxylate, alkylcarbonyl, alkoxycarbonyl, aminocarbonyl, and alkylthiocarbonyl groups.

The term "heteroatom-unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_n$-alkylamino" includes groups, having the structure —NHR, in which R is a heteroatom-unsubstituted $C_n$-alkyl, as that term is defined above. A heteroatom-unsubstituted alkylamino group would include —$NHCH_3$, —$NHCH_2CH_3$, —$NHCH_2CH_2CH_3$, —$NHCH(CH_3)_2$, —$NHCH(CH_2)_2$, —$NHCH_2CH_2CH_2CH_3$, —$NHCH(CH_3)CH_2CH_3$, —$NHCH_2CH(CH_3)_2$, —$NHC(CH_3)_3$, —$N(CH_3)_2$, —$N(CH_3)CH_2CH_3$, —$N(CH_2CH_3)_2$, N-pyrrolidinyl, and N-piperidinyl.

The term "heteroatom-substituted $C_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted $C_n$-alkylamino" includes groups, having the structure —NHR, in which R is a heteroatom-substituted $C_n$-alkyl, as that term is defined above.

The term "heteroatom-unsubstituted $C_n$-alkenylamino" refers to a radical, having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted $C_2$-$C_{10}$-alkenylamino has 2 to 10 carbon atoms. The term "heteroatom-unsubstituted $C_n$-alkenylamino" includes groups, having the structure —NHR, in which R is a heteroatom-unsubstituted $C_n$-alkenyl, as that term is defined above. Examples of heteroatom-unsubstituted $C_n$-alkenylamino groups also include dialkenylamino and alkyl(alkenyl)amino groups.

The term "heteroatom-substituted $C_n$-alkenylamino" refers to a radical, having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkenylamino has 2 to 10 carbon atoms. The term "heteroatom-substituted $C_n$-alkenylamino" includes groups, having the structure —NHR, in which R is a heteroatom-substituted $C_n$-alkenyl, as that term is defined above.

The term "heteroatom-unsubstituted $C_n$-alkynylamino" refers to a radical, having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atoms, a total of one nitrogen atom, and no additional heteroatoms. For example, a heteroatom-unsubstituted $C_2$-$C_{10}$-alkynylamino has 2 to 10 carbon atoms. The term "heteroatom-unsubstituted $C_n$-alkynylamino" includes groups, having the structure —NHR, in which R is a heteroatom-unsubstituted $C_n$-alkynyl, as that term is defined above. An alkynylamino group includes dialkynylamino and alkyl(alkynyl)amino groups.

The term "heteroatom-substituted $C_n$-alkynylamino" refers to a radical, having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkynylamino has 2 to 10 carbon atoms. The term "heteroatom-substituted $C_n$-alkynylamino" includes groups, having the structure —NHR, in which R is a heteroatom-substituted $C_n$-alkynyl, as that term is defined above.

The term "heteroatom-unsubstituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted $C_6$-$C_{10}$-arylamino has 6 to 10 carbon atoms. The term "heteroatom-unsubstituted $C_n$-arylamino" includes groups, having the structure —NHR, in which R is a heteroatom-unsubstituted $C_n$-aryl, as that term is defined above. A heteroatom-unsubstituted arylamino group includes diarylamino and alkyl(aryl)amino groups.

The term "heteroatom-substituted $C_n$-arylamino" refers to a radical, having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted $C_6$-$C_{10}$-arylamino has 6 to 10 carbon atoms. The term "heteroatom-substituted $C_n$-arylamino" includes groups, having the structure —NHR, in which R is a heteroatom-substituted $C_n$-aryl, as that term is defined above. A heteroatom-substituted arylamino group includes heteroarylamino groups.

The term "heteroatom-unsubstituted $C_n$-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted $C_7$-$C_{10}$-aralkylamino has 7 to 10 carbon atoms. The term "heteroatom-unsubstituted $C_n$-aralkylamino" includes groups, having the structure —NHR, in which R is a heteroatom-unsubstituted $C_n$-aralkyl, as that term is defined above. An aralkylamino group includes diaralkylamino groups.

The term "heteroatom-substituted $C_n$-aralkylamino" refers to a radical, having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P, and S. For example, a heteroatom-substituted $C_7$-$C_{10}$-aralkylamino has 7 to 10 carbon atoms. The term "heteroatom-substituted $C_n$-aralkylamino" includes groups, having the structure —NHR, in which R is a heteroatom-substituted $C_n$-aralkyl, as that term is defined above. The term "heteroatom-substituted aralkylamino" includes the term "heteroaralkylamino."

The term "heteroatom-unsubstituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term "heteroatom-unsubstituted $C_n$-amido" includes groups, having the structure —NHR, in which R is a heteroatom-unsubstituted $C_n$-acyl, as that term is defined above. The term amido includes N-alkyl-amido, N-aryl-amido, N-aralkyl-amido, acylamino, alkylcarbonylamino, arylcarbonylamino, and ureido groups. The group, —NHCOCH$_3$, is an example of a heteroatom-unsubstituted amido group.

The term "heteroatom-substituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-amido has 1 to 10 carbon atoms. The term "heteroatom-substituted $C_n$-amido" includes groups, having the structure —NHR, in which R is a heteroatom-unsubstituted $C_n$-acyl, as that term is defined above. The group, —NHCO$_2$CH$_3$, is an example of a heteroatom-substituted amido group.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s).

Any undefined valency on an atom of a structure shown in this application implicitly represents a hydrogen atom bonded to the atom.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dehydrate) water molecules associated with each compound molecule, such as in solid forms of the compound.

As used herein, the term "IC$_{50}$" refers to an inhibitory dose which is 50% of the maximum response obtained.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dogs, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition or pharmaceutical preparation that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

As used herein, "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject of patient which may be at risk and/or predisposed to the disease but does not yet experience or display any or all of the pathology or symptomatology of the disease.

The term "saturated" when referring to a atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

As used herein, the term "water soluble" means that the compound dissolves in water at least to the extent of 0.010 mole/liter or is classified as soluble according to literature precedence.

II. Compounds of the Invention

The compounds provided by the present disclosure are shown, for example, above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

III. Process Scale-Up

The above methods can be further modified and optimized for preparative, pilot- or large-scale production, either batch of continuous, using the principles and techniques of process chemistry as applied by a person skilled in the art. Such principles and techniques are taught, for example, in *Practical Process Research & Development* (2012), which is incorporated by reference herein.

I. Pharmaceutical Compositions

Pharmaceutical compositions of the present invention comprise an effective amount of one or more compounds of the present invention or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one compound of the present invention or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The compound of the present invention may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The compound of the present invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include a compound of the present invention, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the compound of the present invention may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the compound of the present invention are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, a compound of the present invention may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound may be formulated for administration via various miscellaneous routes, for example, topical or transdermal administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Vitamin K Derivatives Yields Highly Potent Anti-Epileptic and Neuroprotective Agents Experimental Section Cell Culture The HT22 neuronal cell line is a subclone of HT4, derived from the mouse hippocampus (Morimoto and Koshland, 1990). They do not express active ionotropic glutamate receptors and are not subject to excitotoxicity (Maher and Davis, 1996). HT22 cells were used. The cells were grown in Dulbecco's Modified Eagle's medium (DMEM/high glucose) supplemented with 10% fetal bovine serum (Hyclone) and 5 mL Antibiotic-Antimycotic (Amphotericin B, Penicillin, and Streptomycin; Invitrogen) at 37° C. in 5% $CO_2$.

Cell Viability Assay

Cell viability was assessed by the ability of the viable cells to metabolize 3-(4,5-dimethylthiazol-2-yl)-5-(3-carboxymethoxyphenyl)-2(4-sulfophenyl)2-H-tetrazolium, inner salt (MTS), as described previously (Cory et al., 1991). The metabolism of tetrazolium salts is often used to measure cellular proliferation, but in the system used here, it has been previously shown to correlate well with cell viability as determined by trypan blue exclusion and colony-forming assays (Davis and Maher, 1994). Briefly, HT-22 cells were seeded onto 96-well plates at $5.0 \times 10^3$ cells per well in 75 µL of medium and maintained at 37° C. in 5% $CO_2$ overnight prior to the initiation of experimental treatments. For glutamate toxicity testing, cells were subsequently treated with 25 µL of medium containing glutamate (monosodium glutamate, Sigma, 1 M stock concentration in media, to achieve a final concentration of 10 mM) plus inhibitors (stock in DMSO) and maintained at 37° C. in 5% $CO_2$. For t-BuOOH toxicity testing, cells were subsequently treated with 25 µL of medium containing t-BuOOH (Sigma, 10 mM stock concentration, to achieve a final concentration of 50 µM) plus inhibitors (stock in DMSO) and maintained at 37° C. in 5% $CO_2$ for 3 hours, after which the media was removed, cells washed gently with HBSS, the media replaced with standard culture media, and the cells returned to incubation at 37° C. in 5% $CO_2$. For both glutamate and t-BuOOH treatments, 10 µl of MTS solution was added to each well 24 hrs after initial treatment, and the cells were maintained in growth medium for 2 h at 37° C. Absorbance at 490 nm was subsequently measured by a SpectraMax 190 plate reader (Molecular Devices). The growth medium without cells in the presence of MTS solution was used as solution background and untreated cells were considered the controls. Cell viability was calculated as a percentage compared with untreated controls. $EC_{50}$ determinations were based on 12-point titrations using GraphPad Prism, and each experiment was repeated at least four times. Morphology of HT22 cells following treatments was determined by phase-contrast microscopy. Digital images of cells grown on cell culture plates were captured at 10× magnification.

Glutathione Determination

The content of total glutathione (reduced and oxidized) in the supernatant of cell homogenate was measured using the glutathione assay kit (Cayman Chemical) in microtiter plate assay, which utilizes an enzymatic recycling method, using glutathione reductase, for the quantification of glutathione. The sulfhydryl group of glutathione reacted with 5,5'-dithiobis-2-nitrobenzoic acid (DTNB) and produced a yellow-colored 5-thio-2-nitrobenzoic acid (TNB), which was measured at 405 nm.

Antioxidant Activity Assay

Antioxidant activity of various reagents was assayed as previously described by monitoring the disappearance of the optical absorbance of the stable-free radical DPPH on reaction with test compounds (Blois, 1958). The rate of the reaction represents the antioxidant potency of test agents. The known free radical scavenger Trolox and ascorbic acid were used as positive controls. Briefly, 10 µL of test reagents at final concentrations of 20 µM were added to 200 µL of 100 µM DPPH in methanol. Optical absorbance of DPPH at 517 nm was immediately monitored for 10 min.

Intracellular ROS Measurement and Imaging

Intracellular generation of ROS was evaluated by spectrofluorometry using the membrane-permeable compound dihydrorhodamine 123 (Rho123; Invitrogen), and images were collected using 5-(and -6)-chloromethyl-2',7'-dichlorodihydrofluorescein diacetate, acetyl ester (CM-$H_2$DCFDA; Invitrogen). Briefly, HT-22 cells were seeded onto black walled 96-well plates at $5.0 \times 10^3$ cells per well in 75 µL of medium and maintained at 37° C. in 5% $CO_2$ overnight prior to the initiation of experimental treatments. Cells were subsequently treated with 25 µL of medium containing glutamate (monosodium glutamate, Sigma, 1 M stock concentration in media, to achieve a final concentration of 10 mM) plus inhibitors (stock in DMSO) and maintained at 37° C. in 5% $CO_2$. After 8 hrs, Rho123 (5 µM), CM-$H_2$DCFDA (1 µM), or MitoSox (5 µM) and Mitotracker DR (10 nM) was added to achieve the indicated final concentrations. Cells were allowed to incubate for 20 minutes and then washed twice with Hanks Balanced Salt Solution (HBSS; Hyclone; $CaCl_2$ 1.26 mM, $MgCl_2$-$6H_2O$ 0.493 mM, $MgSO_4$-$7H_2O$ 0.407 mM, KCl 5.33 mM, $KH_2PO_4$ 0.441 mM, $NaHCO_3$ 4.17 mM, NaCl 137.93 mM, $Na_2HPO_4$ 0.338 mM, D-Glucose 5.56 mM), with a final addition of 100 µL of HBSS in which the cells were visualized. Fluorescence of the oxidized Rho123 was measured using a Fluoroskan Ascent spectrofluorometer (Labsystems). Peak excitation and emission wavelengths were 500 and 536, respectively. For fluorescent imaging of the oxidation product of CM-$H_2$DCFDA, cells were immediately visualized using an InCell 2000 Analyzer (GE) with a 40× objective and a FITC excitation/emission filter set. Image processing was performed using ImageJ, and for all images, the microscope and image processing settings, such as levels, brightness, contrast, and exposure time were held constant across all treatment conditions.

Mitochondrial Morphology and Superoxide Generation

In order to evaluate the source of the ROS generation, fluorescence microscopy was used to image HT22 using the fluorogenic dyes Mitotracker Deep Red (DR) and MitoSOX Red (Invitrogen). Mitotracker DR is a cell permeant dye that accumulates in active, polarized mitochondria. MitoSOX Red is highly selective reagent for the detection of superoxide in the mitochondria of live cells. It is live-cell permeant and rapidly and selectively targeted to mitochondria, where it is readily oxidized by superoxide, but not other cellular free radicals, and exhibits red fluorescence. Briefly, HT22 cells were seeded onto black walled 96-well plates at $5.0 \times 10^3$ cells per well in 75 µL of medium and maintained at 37° C. in 5% $CO_2$ overnight prior to the initiation of experimental treatments. Cells were subsequently treated with 25 µL of medium containing glutamate (monosodium glutamate, Sigma-Aldrich, 1 M stock concentration in media, to achieve a final concentration of 10 mM) plus inhibitors (stock in DMSO) and maintained at 37° C. in 5% $CO_2$. After 8 hrs, MitoSOX Red (5 µM) and Mitotracker DR (10 nM) were added to achieve the indicated final concentrations. Cells were allowed to incubate for 20 minutes and then washed twice with Hanks Balanced Salt Solution (HBSS; Hyclone; $CaCl_2$ 1.26 mM, $MgCl_2$-$6H_2O$ 0.493 mM, $MgSO_4$-$7H_2O$ 0.407 mM, KCl 5.33 mM, $KH_2PO_4$ 0.441 mM, $NaHCO_3$ 4.17 mM, NaCl 137.93 mM, $Na_2HPO_4$ 0.338 mM, D-Glucose 5.56 mM), with a final addition of 100 µL of HBSS in which the cells were visualized. Cells were immediately visualized using an InCell 2000 Analyzer (GE) with a 40× objective and a Cy5/Cy5 excitation/emission filter set for Mitotracker DR and a YFP/Cy3 filter set for MitoSOX Red. Image processing was performed using ImageJ, and for all images, the microscope and image processing settings, such as levels, brightness, contrast, and exposure time were held constant across all treatment conditions.

Real-Time Polymerase Chain Reaction

HT22 cells were seeded onto cell culture treated 6-well plates at $3.0 \times 10^5$ cells per well in 2 mL of medium and maintained at 37° C. in 5% $CO_2$ overnight prior to the initiation of experimental treatments. Cells were subsequently treated with 1 mL of medium containing glutamate (monosodium glutamate, Sigma-Aldritch, 1 M stock concentration in media, to achieve a final concentration of 10 mM) plus inhibitors (stock in DMSO) and maintained at 37° C. in 5% $CO_2$. After 16 hrs, the media was collected and the cells harvested by trypsanization. After centrifugation, pelleted cells were washed with cold Hanks' Balanced Salt Solution (HBSS $Ca^{2+}$/$Mg^{2+}$ Free; Invitrogen; KCl 5.33 mM, $KH_2PO_4$ 0.441 mM, $NaHCO_3$ 4.17 mM, NaCl 137.93 mM, $Na_2HPO_4$ 0.338 mM, D-Glucose 5.56 mM), qRT-PCR was used to detect HO-1, NQO-1, and PGAM5 mRNAs in the HT22 cells. Consistent with reports utilizing serum starvation models, the mRNA levels of both Actin and GAPDH were found to be strongly affected by glutamate treatment, but $β_2$-microglobulin remained fairly stable. Therefore $β_2$-microglobulin was used as a reference gene (Barrionuevo and Burggren, 1999). HT22 cells were cultured as described for 16 hrs. Total RNAs were extracted using the RNEasy kit (Qiagen), and transcripts of interest were amplified by PCR using the 1-step Syber Green qRT-PCR kit (Quanta) and the following specific primers (Harvard PrimerBank; Integrated DNA Technologies): HO-1, 5'-GCCACCAAGGAGGTA-CACAT-3' (SEQ ID NO:1) and 5'-GCTTGTTGCGCTC-TATCTCC-3' (SEQ ID NO:2); PGAM5, 5'-TGACACCATT-AGGTCGGGAACT-3' (SEQ ID NO:3) and 5'-TACTGCACGGGTCATAGAGGA-3' (SEQ ID NO:4); NQO-1, 5'-AGGATGGGAGGTACTCGAATC-3' (SEQ ID NO:5) and 5'-AGGCGTCCTTCCTTATATGCTA-3' (SEQ ID NO:6); and $β_2$-microglobulin, 5'-ACCCGCCTCACAT-TGAAATCC-3' (SEQ ID NO:7) and 5'-GGCGTATG-TATCAGTCTCAGT-3' (SEQ ID NO:8). Linearity of the primers was verified before use, and fold changes were calculated as previously described using the Livak method (Barrionuevo and Burggren, 1999).

Western Blot and Densitometric Analysis

HT-22 cells were cultured and treated as described above for the qRT-PCR experiments. After 16 hrs, the media was collected and the cells harvested by trypsanization. After centrifugation, pelleted cells were washed with cold HBSS $Ca^{2+}$/$Mg^{2+}$ Free, followed by lysis with a low salt lysis buffer (50 mM Tris-HCl, pH 7.4, 150 mM NaCl, 10% glycerol, 0.5 Triton X-100, 1× protease and phosphatase inhibitor cocktail) for 30 min, followed by a 15-s sonication pulse at 30 W. For Western blot analysis, the cell lysates were denatured with LDS loading buffer (Invitrogen) and run on Nupage 4-12% Tris-glysine gradient gels (Invitrogen) after centrifugation. Phosphorylated Drp1 (Ser637) (Cell Signaling) and total Drp1 (C5) (Santa Cruz), PGAM5 (K16) (Santa Cruz Biotechnology), Actin (Sigma-Aldrich) and alpha-Tubulin (Santa Cruz Biotechnology) were assessed with primary antibody, followed by rabbit, mouse, or goat IgG-HRP secondary antibody. The blot was developed using Pierce Thermo Dura-ECL reagent (Thermo-Fisher) and visualized using an ImageQuant LAS 4000 (GE). Digital images of membranes were quantified by computer-assisted densitometry using Image J 1.42q (National Institutes of Health, MD).

Animals and Chronic Toxicity Evaluation.

Adult (12 weeks of age) mice (Balb/cByJ, 17-20 g, Jackson Laboratory), were housed in temperature-controlled conditions under a light/dark photocycle with food and water supplied ad libitum. Mice were divided randomly into three groups. The first group (n=3) was injected i.p. with compound 2q at 50 mg/kg dissolved in sterile 5% DMSO, 95% Neobee (Spectrum Chemical) (Allen et al., 2006). The second group (n=3) was injected i.p. with compound 2j at 50 mg/kg dissolved in sterile 5% DMSO, 95% Neobee. The third, vehicle control group (n=2) was injected i.p. with an equivalent volume of sterile 5% DMSO, 95% Neobee. All animals were injected between 11:00 a.m. and 12:00 p.m. Animals were sacrificed by $CO_2$ after three weeks of injections. Blood was collected by cardiac puncture and standard blood count and chemistry was evaluated by the MUSC/VA Veterinary Diagnostic Laboratory (Charleston, S.C.). All animal and treatment protocols were in compliance with the *Guide for the Care and Use of Laboratory Animals* as adopted and promulgated by the National Institutes of Health (Institute of Laboratory Animal Resources, 1996).

Zebrafish Experiments

Zebrafish (AB strain) were obtained from the Zebrafish International Resource Center, which is supported by grant P40 RR012546 from the NIH-NCRR. Brn3a-GFP zebrafish were purchased from RIKEN, Japan. Zebrafish were maintained and crossed according to standard methods (Westerfield, 2000). Fertilized eggs were collected and placed in E3 embryo medium and positioned in an incubator set at 28.5° C. with a 14/10 hr light/dark cycle. Embryos were staged using the criteria of Kimmel et al. (1995).

Chemicals Used in Zebrafish Experiments

PTZ (Sigma P6500), PPM-18, SAHA, R106, dPAHA, NSC, Tubastatin A, TDZD-8, Ebselen, VPA (Sigma P4543) and Vitamins K1, K2 and K3 were synthesized in the laboratory or obtained from commercially available sources (Inks et al., 2012).

Toxicity Studies

Using a 96-well plate, one zebrafish larva (7 dpf) was placed in each well in 100 µL of tank water (TW). 100 µL of each compound (0.5-15 µM) was then added to each well for 12 animals (one row) to give a final volume of 200 ΞL. A control row was tested for DMSO toxicity effects. The 96-well plate was then placed on a warmer plate at 32° C. and the fish were observed for phenotype, behavior and mortality initially after addition of compound, after 1 hr of treatment and after 5 hr of treatment. Each drug was assessed for the no observed effect concentration (NOEC), the highest non-lethal dose resulting in no apparent toxic effects.

These compounds were screened for potential teratogenic effects. For each row within a 96-well plate, one compound was tested at two concentrations; six fish in columns 1-6 were tested for lower concentrations and six fish in columns 7-12 for higher concentrations of the same compound. Overall, there were six fish per treatment per dose. A control row was tested for DMSO toxicity effects. Columns 1-6 were treated with 1:5 DMSO and columns 6-12 were treated with 1:50 DMSO. The embryos were incubated at 28.5° C. and raised in a 14 hour light/10 hour dark cycle. The embryos were observed daily for developmental and behavioral abnormalities, as well as mortality until they reached 7 dpf.

Induction and Monitoring of Seizures in Zebrafish

Seizures were induced in 6-7 dpf zebrafish larvae by addition of 15 mM PTZ as originally developed by Baraban et al. (2005) Larvae were dosed with the NOEC of each compound pre- and post-PTZ treatment. The DanioVision locomotion tracking instrument with Ethovision XT software (Noldus) was used to measure the severity of the seizures by quantifying the locomotor activity of each fish.

In a 48-well plate, one 6-7 dpf larva was added per well. Compounds were given at a sub-lethal dose and treated for 1 h. Three control rows were included—tank water (TW) only, PTZ only and PTZ+VPA (2-4 mM final concentration of VPA). PTZ was added to all wells except for the TW only wells to a final concentration of 15 mM. After 5 min, the plate was transferred to the Daniovision apparatus and the chamber light was turned on. After 2 min, Ethovision was used to determine the distance traveled (a marker of seizure activity) by each fish for 15 min (25 frames per second). Velocity, duration of movement, and frequency of movement were also determined from the same recording. After measurement, fish were monitored visually for survival. The distance moved over the recording period with Ethovision XT software (Noldus) was averaged over 8 wells per treatment unless the fish was not detected.

Results:

As shown below, the results of in vitro evaluations of various derivatives of VK are presented which provide data relating to the structural requirements for efficient neuroprotective activity, without the manifestation of in vitro cytotoxicity. As shown herein, the inventors provide the development and facile synthesis of compounds with favorable drug-like properties (e.g., low ClogP<5.0 and tPSA<60) that, based on their capacity to inhibit oxidative-stress mediated neuronal cell death, were found to be potent neuroprotective agents without obvious neurotoxicity in vitro, and with activity exceeding that of VK2 greater than 10 fold. Standard blood count and chemistry testing also revealed no blood or major organ toxicity in mice. The mechanisms that may underly the neuroprotective effects of VK2 and select promising compounds were also investigated.

Epilepsy is a devastating neurological disorder characterized by periodic and unpredictable occurrence of seizures. Epilepsy affects approximately 2% of the world's population and is also a common symptom of various mitochondrial diseases (Saneto et al., 2010). The causes of epilepsy are still unknown. The mitochondrion has several important functions including production of ATP, central involvement in apoptosis, formation of reactive oxygen species and calcium homeostasis (Folbergrova and Kunz, 2011; Canafoglia et al., 2001). Several theories involve the mitochondrion in the induction of seizures as well as the neuronal damage and death that occurs after seizures (Waldbaum and Patel, 2010). The brain has a lower anti-oxidant capacity than other tissues, making it a vulnerable organ to oxidative stress-induced damage, particularly after excitotoxicity (Waldbaum and Patel, 2010).

Figure 1A:
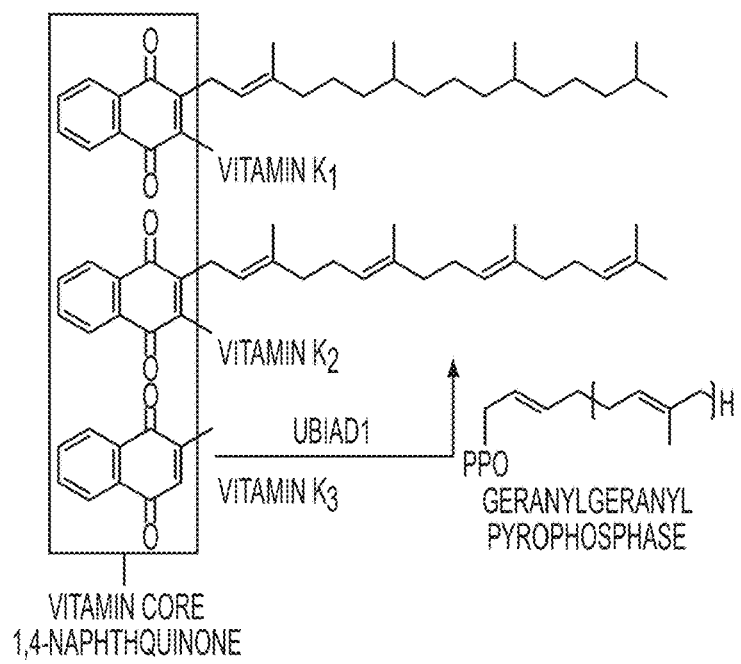
FIGS. 1A-1B—FIG. 1A. Structures of $VK_1$, $VK_2$, and $VK_3$. $VK_3$ is a pro-vitamin, and UBIAD1 converts vitamin $K_3$ or de-isoprened vitamin $K_1$ into $VK_2$ in situ through geranylgeranylation. Defects in UBIAD1 have been shown to be a dominant enhancer of Parkinson's related PINK1 mutations.

Despite current treatment options, 25% of patients with epilepsy are still inadequately treated (Duncan, 2002). Less than twenty drugs are FDA-approved in the United States. Valproic acid (2-n-propylpentanoic acid, VPA, FIG. 1A) is a commonly used anticonvulsant agent and is the only therapeutic agent approved by the FDA for the treatment of all types of epileptic seizures. VPA is also known for its mood stabilizing property for bipolar disorder and is also used as a prophylaxis for migraine headaches. VPA is generally well-tolerated, however VPA treatment is associated with several side effects, such as acute hepatic failure and pancreatitis (Lheureux and Hantson, 2009). VPA-associated toxicities are postulated to be due to its high therapeutic dose requirement. In addition, severe teratogencity is also associated VPA treatment, which limits its use in pregnant women.

VPA is contra-indicated for patients with mitochondrial disease (Finsterer and Segall, 2010), especially those with mutations in the mitochondrial DNA polymerase, POLG associated with Alpers syndrome (Saneto et al., 2010). In particular, those with the POLG Q1236H or E1143G polymorphisms were shown to have a greater likelihood of VPA toxicity (Stewart et al., 2010). Q1236H and E1143G are found in 8.6% and 4% of the world's population, respectively, and may not be neutral polymorphisms (Stewart et al., 2010; Chan et al., 2006). Furthermore, for those with mitochondrial diseases that include epileptic seizures, for example MERRF patients (patients with myoclonic epilepsy and ragged red fibers) or Alpers syndrome, VPA causes a rapid decline. This underscores the need for an anti-seizure therapy that does not adversely affect patients with underlying mitochondrial dysfunction. Better anti-seizure therapeutics are also needed for young children, as 1/500 on polytherapy are at risk for liver toxicity with VPA (Stewart et al., 2010). VPA is also contra-indicated for pregnant women, due to the teratogenic effect of VPA on the fetus (Alsdorf and Wyszynski, 2005).

Although the molecular mechanisms of its anti-epileptic and neuroprotective effects are still unclear, they are strongly correlated to its ability to inhibit histone deacetylases (HDAC). VPA is a branched chain carboxylic acid and is very similar to short-chain fatty acids, making VPA a substrate for the fatty acid/beta oxidation pathways (Lheureux and Hantson, 2009; Silva et al., 2008). VPA has been shown to inhibit mitochondrial beta-oxidation in rat hepatocytes (Turnbull et al., 1983), although this was not seen in a recent study using patient myoblasts (Stewart et al., 2010). VPA also promotes the transport of glutamine through the mitochondrial membrane, thereby enhancing glutaminase activity and the production of glutamate that can then enter the Kreb's cycle, products of which can then enter the electron transport chain and oxidative phosphorylation for ATP production (Lheureux and Hantson, 2009). VPA increases GABA synthesis and release, and GABAergic transmission is subsequently potentiated in specific brain regions (Perucca, 2002). VPA also reduces the release of the excitatory amino acid β-hydroxybutyric acid and can attenuate neuronal excitation mediated by activation of NMDA glutamate receptors. VPA can also exert direct actions on excitable membranes including blockage of voltage-dependent sodium channels and may modulate dopaminergic and serotoninergic transmission. As VPA has multiple and complex modes of action, this may explain the toxic side effects observed with usage of this agent (Perucca, 2002).

Zebrafish (*Danio rerio*) are small freshwater teleosts that are an important model organism for development and neurobiology. Zebrafish can produce hundreds of embryos that develop outside of the mother. Because these embryos are transparent, development can be monitored and any phenotypic changed can be scored. Furthermore, zebrafish embryos are amenable to high throughput drug screens, as well as genetic manipulation (Zon and Peterson, 2010). High-resolution video can be used to capture zebrafish behavior, which can later be used for the quantification of locomotor activity (Baraban et al., 2005). Pentylenetetrazole (PTZ) is a GABA antagonist (Chaix et al., 2007), and PTZ treatment induces seizures in zebrafish and rodents that mimic human epileptic seizures (Baraban, 2007). Several anti-seizure drugs, including VPA and diazepam, were found to reduce convulsions in PTZ-treated zebrafish in a dose-dependent manner (Zon and Peterson, 2005).

Since VPA inhibits several HDACs the inventors utilized a high throughput screen to identify several compounds that act as potent inhibitors of HDAC at the micro-molar level (Inks et al., 2012). The inventors hypothesized that these micro-molar HDAC inhibitors might be more effective than VPA for epilepsy. Several of the more potent HDAC inhibitors with limited toxicity in a human HT22 neuronal cell line on PTZ-treated zebrafish were tested and found to have reduced seizure activity compared to HDAC inhibitors in the screen. Several analogs were then developed that could reduce seizure activity at low concentrations without toxicity. Finally, experiments to evaluate the mode of action of these compounds were carried out.

Vitamin K Analog Synthesis 2-amino-1,4-naphthoquinone (1d) was synthesized as previously described (Fieser, 1935). The synthesis of this compound has been successfully scaled up. and the reported synthesis has been found to be amenable to both milligram and multi-gram scale reactions. The other 2-amino substituted 1,4-napthoquinones were synthesized following a basic procedure as previously described with only minor modifications made as needed (Table 2) (Valente et al., 2007; Tandon et al., 2004). Briefly, to a solution of 2-bromo-1,4-naphthoquinone in ethanol was added an excess of the corresponding amine, and the reaction was stirred at room temperature and monitored by TLC. This reaction was found to provide decent yields, be applicable to a variety of amine substrates, and spectroscopically pure product was frequently obtained by simple vacuum filtration. The inexpensive cost of reagents, simple and environmentally friendly reaction and purification conditions, coupled with the extremely high potency, neuroprotective efficacy, and lack of in vitro neurotoxicity, makes these compounds an attractive and promising option for the development of neuroprotective agents.

In synthesizing the 2-amido substituted derivatives, when starting from compound 1d, the inventors found the 2' amine to be highly deactivated and to not be amenable to several standard peptide coupling procedures. Activations with triethylamine and tert-butyllithium and subsequent additions of acyl chlorides also proved to be unsuccessful. Desired products were obtained in reasonable yields by dissolving compound 1d and 4.2 equivalents of sodium hydride in dry THF, followed by dropwise addition of the corresponding acyl chloride (Table 3). 2-ureyl substituted derivatives were synthesized as previously described (Table 4) (Nagai, 1979). Briefly, to a stirred solution of Compound 1d dissolved in dimethylformamide was added the corresponding isocyanate followed by a catalytic amount of triethylamine. The reaction was then heated to 80° C. and monitored using TLC. The non-redox chromone based analogs, 5c and 5d, were also synthesized by dissolving the appropriate carboxylic acid in dimethylformamide (Table 5). Then the solution was cooled to 0° C., and two equivalents of thionyl chloride were added and the mixture stirred for 30 minutes, followed by the addition aniline. The following day, the reaction was quenched with an excess of saturated sodium bicarbonate, and the resulting precipitate was filtered and crystallized with hot ethyl acetate.

Neuroprotection Structure-Activity Relationships

Figure 1B:
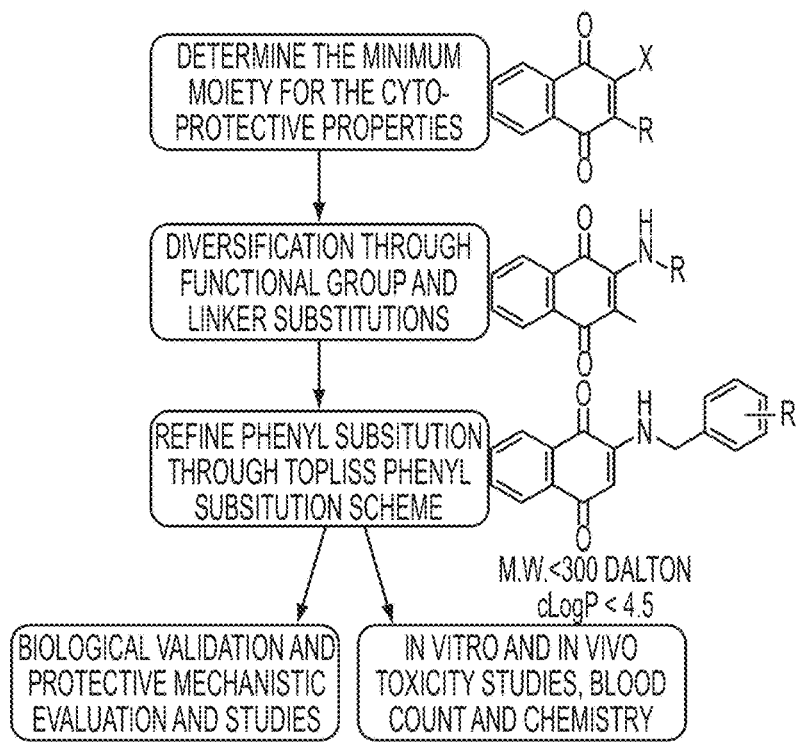

The neuroprotective properties of VK and its derivatives were estimated through their protective effects against cell death in mouse neuronal HT22 cells induced by exposure to high levels of glutamate, which recapitulates a hallmark of the extracellular environment found in several neurodegenerative diseases and CNS injuries and is a well established model of neuronal oxidative stress. This investigation began by comparing the relative abilities of the two predominant naturally occurring forms of VK, $VK_1$ and $VK_2$, to prevent oxidative cell death. Consistent with the reported literature utilizing primary cortical neurons (Li et al., 2003), $VK_2$ was found to be many times more potent than $VK_1$, but neither exhibited any signs of cellular toxicity (FIG. 15). Since both $VK_1$ and $VK_2$ rescued HT22 cells from oxidative cell death, the inventors hypothesized that it was the 1,4-naphthoquinone core, and not the isoprenoid side chain, that was responsible for the neuroprotective effects. Several 1,4-naphthoquinones with various substitutions at the 2' and 3' positions were tested to determine the minimum structural requirement of the system and what the optimum scaffold for future developmental efforts and biological validation would be (FIG. 1B and Table 1). Consistent with this hypothesis, un-substituted 1,4-naphthoquinone does exhibit neuroprotective activity at micromolar concentrations. Substitution by a single methyl group at the 2' position ($VK_3$) improves the compound's ability to protect against cell death. Various other simple substituents at the 2' and 3' positions give the naphthoquinone structure the ability to prevent oxidative cell death at nanomolar concentrations (Table 1 and FIG. 16). Of the tested structures, the presence of a single amine group at the 2' position was found to provided the greatest potency and the lowest non-specific cellular toxicity, so this structure was chosen as the scaffold for further modification.

The inventors then tested the effects of modifying the 2' amine group. Amino, amido, and ureyl derivatives were also synthesized and their effects tested. It was observed that for the most part, both the amido and ureyl derivatives demonstrated decreased potency relative to compound 1d, and many exhibited significant non-specific toxicity (Table 6 and Table 7). The same can be said for most of the amino derivatives with short alkyl or cycloalkyl substituents, although in the case of the methyl and dimethyl groups (2a & 2c; Table 2), cellular toxicity was abolished. However, the inventors found that the addition of a benzyl group to the 2' amine completely abolished all toxicity associated with the molecule, while maintaining a low nanomolar $PC_{50}$ (2j; Table 2).

TABLE 1

In Vitro Neuroprotective Activity of 1,4-naphthoquinones substituted at the 2' and 3' positions.

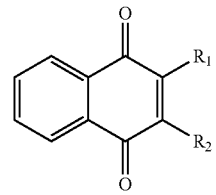

| Compound | $R_1$ | $R_2$ | Protection[a] $PC_{50}$ (nM) | Toxicity[b] $TC_{50}$ (nM) | Safety Index $TC_{50}/PC_{50}$ |
|---|---|---|---|---|---|
| $VK_2$ | — | — | 432 | >100,000 | 231 |
| 1a | —H | —H | 1541 | 19,000 | 12 |
| 1b | —Me | —H | 797 | 19,000 | 24 |
| 1c | —Me | —Me | 118 | 30,000 | 254 |
| 1d | —$NH_2$ | —H | 61 | 49,000 | 803 |
| 1e | —$NH_2$ | —Me | 1740 | 54,000 | 31 |
| 1f | —COOH | —H | 716 | >100,000 | 140 |
| 1g | —OH | —H | 1005 | >100,000 | 100 |

[a]In vitro neuroprotective activity and [b]neurotoxicity assessed by treating HT22 cells with various concentrations of compounds with or without 10 mM glutamate for 24 hrs. Cell viability was estimated by treating cells with MTS and measuring absorbance at 490 nM. $PC_{50}$, concentration producing 50% protection, values calculated using GraphPad Prism based on 12 point titrations, n ≥ 4; $TC_{50}$, concentration producing 50% toxicity, values calculated using GraphPad Prism based on 7 point titrations, n ≥ 3.

Based on these results, compound 2j was selected as the lead compound. The effects of varying the number of carbons in the linker region between the quinone and the phenyl ring were explored by synthesizing and testing compounds 2i and 2l. While compound 2i, with the linker region removed, did show increased potency, it also manifested toxicity. Compound 2l, with a single extra methylene group added to the linker region, demonstrated no toxicity, but suffered from a significant decrease in potency. Compound 2k, with the 2' tertiary amine, was then found to exhibit decreased potency, indicating a potential hydrogen bond interaction occurring at this position. The synthesis of the nitrogen heterocycles 2m-2o, also all exhibited toxicity. Next, several analogues were synthesized according to a Topliss scheme in order to maximize the potency of the molecule by determining the optimum substitution of the benzene ring (Topliss, 1972). None of these compounds manifested any in vitro toxicity, and each of them exhibited increased potency. Compound 2q, with the chlorine atom located in the meta position, was the most potent. Compound 2q displayed a $PC_{50}$ of 31 nM, which represents an almost 3 fold increase over compound 2j, and a more than 10 fold increase over $VK_2$.

TABLE 2

In Vitro Neuroprotective Activity of 2-amino-1,4-naphthoquinones.

| Compound | $R_1$ | $R_2$ | Protection[a] $PC_{50}$ (nM) | Toxicity[b] $TC_{50}$ (nM) | Safety Index $TC_{50}/PC_{50}$ |
|---|---|---|---|---|---|
| $VK_2$ | — | — | 432 | >100,000 | 231 |
| 2a | —H | —Me | 1346 | >100,000 | 74 |
| 2b | —H | —Et | 761 | 81,000 | 106 |
| 2c | —Me | —Me | 246 | >100,000 | 407 |
| 2d | —H | —CH(CH$_3$)$_2$ (isopropyl) | 1703 | 46,000 | 27 |
| 2e | —H | —CH$_2$CH$_2$CH$_2$CH$_3$ (n-butyl) | 328 | 30,000 | 91 |
| 2f | —H | —CH$_2$-cyclopentyl | 409 | 44,000 | 108 |
| 2g | —H | —CH$_2$-cyclohexyl | 54 | >100,000 | 1,852 |
| 2h | —H | —CH$_2$C≡CH (propargyl) | 120 | 53,000 | 442 |
| 2i | —H | —phenyl | 64 | 7,000 | 109 |
| 2j | —H | —CH$_2$-phenyl (benzyl) | 88 | >100,000 | 1,136 |
| 2k | —Me | —CH$_2$-phenyl (benzyl) | 128 | >100,000 | 781 |
| 2l | —H | —CH$_2$CH$_2$-phenyl (phenethyl) | 584 | >100,000 | 171 |

TABLE 2-continued
In Vitro Neuroprotective Activity of 2-amino-1,4-naphthoquinones.
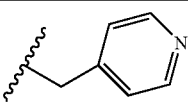
| Compound | R$_1$ | R$_2$ | Protection[a] PC$_{50}$ (nM) | Toxicity[b] TC$_{50}$ (nM) | Safety Index TC$_{50}$/PC$_{50}$ |
|---|---|---|---|---|---|
| 2m | —H | 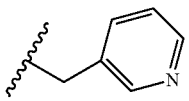 [SMILES: *Cc1cccnc1] | 72 | 80,000 | 1,111 |
| 2n | —H | 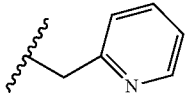 [SMILES: *Cc1ccccn1] | 215 | 37,000 | 172 |
| 2o | —H | 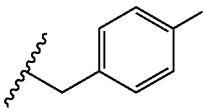 | 933 | 50,000 | 54 |
| 2p | —H | 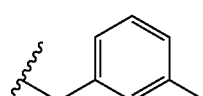 | 59 | >100,000 | 1,695 |
| 2q | —H | 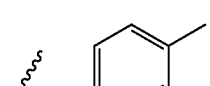 | 31 | >100,000 | 3,226 |
| 2r | —H |  | 66 | >100,000 | 1,515 |
| 2s | —H | 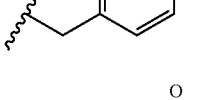 | 114 | >100,000 | 877 |
| 2t | —H | 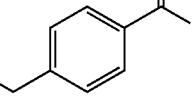 | 232 | >100,000 | 431 |
| 2u | —H | | 45 | >100,000 | 2,222 |

TABLE 2-continued

In Vitro Neuroprotective Activity of 2-amino-1,4-naphthoquinones.

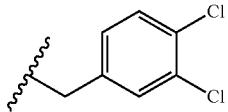 [SMILES: *Cc1ccc(Cl)c(Cl)c1]

| Compound | $R_1$ | $R_2$ | Protection[a] $PC_{50}$ (nM) | Toxicity[b] $TC_{50}$ (nM) | Safety Index $TC_{50}/PC_{50}$ |
|---|---|---|---|---|---|
| 2v | —H | (3,4-dichlorobenzyl) | 46 | >100,000 | 2,174 |

[a]In vitro neuroprotective activity and [b]neurotoxicity assessed by treating HT22 cells with various concentrations of compounds with or without 10 mM glutamate for 24 hrs. Cell viability was estimated by treating cells with MTS and measuring absorbance at 490 nM. $PC_{50}$, concentration producing 50% protection, values calculated using GraphPad Prism based on 12 point titrations, n ≥ 4; $TC_{50}$, concentration producing 50% toxicity, values calculated using GraphPad Prism based on 7 point titrations, n ≥ 3.

TABLE 3

In Vitro Neuroprotective Activity of 2-amido-1,4-naphthoquinones

| Compound | R | Protection[a] $PC_{50}$ (nM) | Toxicity[b] $TC_{50}$ (nM) | Safety Index $TC_{50}/PC_{50}$ |
|---|---|---|---|---|
| 3a | —Me | 616 | >100,000 | 162 |
| 3b | —Et | 760 | 80,000 | 105 |
| 3c | (methoxymethyl) | 69 | 5,000 | 72 |
| 3d | (isopropyl) | >1000 | 8,000 | 0 |
| 3e | (cyclopentyl) | >1000 | 6,000 | 0 |
| 3f | (cyclohexyl) | 275 | 14,000 | 51 |

TABLE 3-continued

In Vitro Neuroprotective Activity of 2-amido-1,4-naphthoquinones

| Compound | R | Protection[a]<br>PC$_{50}$ (nM) | Toxicity[b]<br>TC$_{50}$ (nM) | Safety<br>Index<br>TC$_{50}$/PC$_{50}$ |
|---|---|---|---|---|
| 3g | phenyl | 500 | 17,000 | 34 |
| 3h | 4-methylphenyl | 382 | 24,000 | 63 |
| 3i | 4-chlorophenyl | 405 | 27,000 | 67 |
| 3j | 3-chlorophenyl | 492 | >100,000 | 203 |
| 3k | 4-methoxyphenyl | 658 | 32,000 | 49 |
| 3l | benzyl | 890 | 42,000 | 47 |
| 3m | 4-phenylbenzyl | 161 | >100,000 | 621 |

[a]In vitro neuroprotective activity and [b]neurotoxicity assessed by treating HT22 cells with various concentrations of compounds with or without 10 mM glutamate for 24 hrs. Cell viability was estimated by treating cells with MTS and measuring absorbance at 490 nM. PC$_{50}$, concentration producing 50% protection, values calculated using GraphPad Prism based on 12 point titrations, n ≥ 4; TC$_{50}$, concentration producing 50% toxicity, values calculated using GraphPad Prism based on 7 point titrations, n ≥ 3.

TABLE 4

In Vitro Neuroprotective Activity of 2-ureyl-1,4-naphthoquinones.

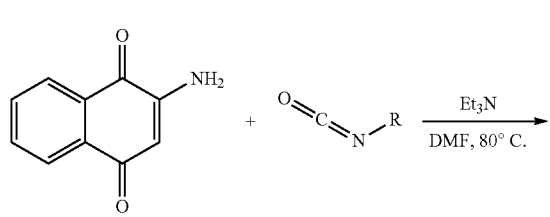

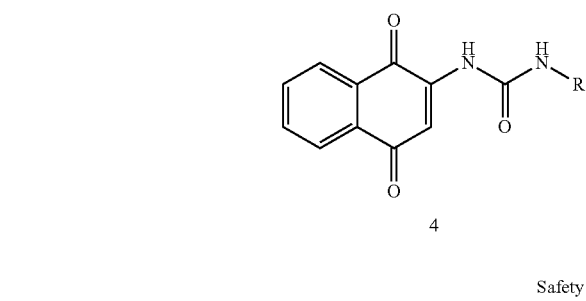

| Compound | R | Protection[a] PC$_{50}$ (nM) | Toxicity[b] TC$_{50}$ (nM) | Safety Index TC$_{50}$/PC$_{50}$ |
|---|---|---|---|---|
| 4a | —Et | 177 | 5,000 | 28 |
| 4b | (isopropyl) | 64 | 8,000 | 125 |
| 4c | (phenyl) | 890 | >100,000 | 112 |
| 4d | (benzyl) | 740 | >100,000 | 135 |

[a]In vitro neuroprotective activity and [b]neurotoxicity assessed by treating HT22 cells with various concentrations of compounds with or without 10 mM glutamate for 24 hrs. Cell viability was estimated by treating cells with MTS and measuring absorbance at 490 nM. PC$_{50}$, concentration producing 50% protection, values calculated using GraphPad Prism based on 12 point titrations, n ≥ 4; TC$_{50}$, concentration producing 50% toxicity, values calculated using GraphPad Prism based on 7 point titrations, n ≥ 3.

TABLE 5

In Vitro Neuroprotective Activity of chromone derivatives.

[reaction scheme: chromone with R$_1$, R$_2$ → 1. 0° C., SOCl$_2$; 2. rt., aniline, DMF → chromone amide]

a) R$_1$: H; R$_2$: COOH
b) R$_1$: COOH; R$_2$: H a) R$_1$: H; R$_2$: CONHAr
b) R$_1$: CONHAr; R$_2$: H

| Compound | Protection[a] PC$_{50}$ (nM) | Toxicity[b] TC$_{50}$ (nM) |
|---|---|---|
| (chromone-2-COOH) | >1000 | >100,000 |
| (chromone-3-COOH) | >1000 | >100,000 |
| (chromone-2-CONHPh) | >1000 | >100,000 |
| (chromone-3-CONHPh) | >1000 | >100,000 |

[a]In vitro neuroprotective activity and [b]neurotoxicity assessed by treating HT22 cells with various concentrations of compounds with or without 10 mM glutamate for 24 hrs. Cell viability was estimated by treating cells with MTS and measuring absorbance at 490 nM. PC$_{50}$, concentration producing 50% protection, values calculated using GraphPad Prism based on 12 point titrations, n ≥ 4; TC$_{50}$, concentration producing 50% toxicity, values calculated using GraphPad Prism based on 7 point titrations, n ≥ 3.

Cellular Biological Evaluation

Figure 2A:
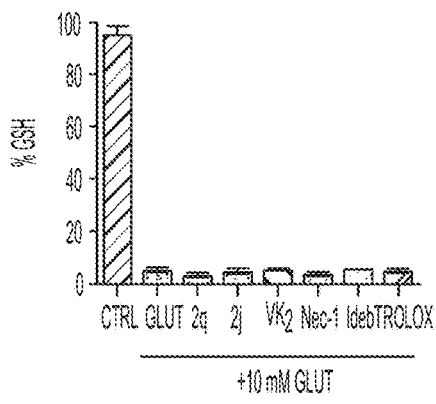
FIGS. 2A-2C—HT22 cells treated for 8 hrs with 10 mM glutamate.
Figure 2B:
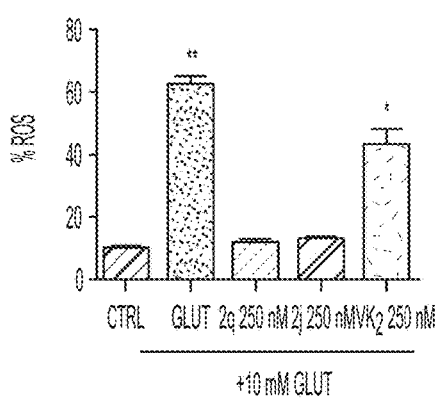
Figure 2C:
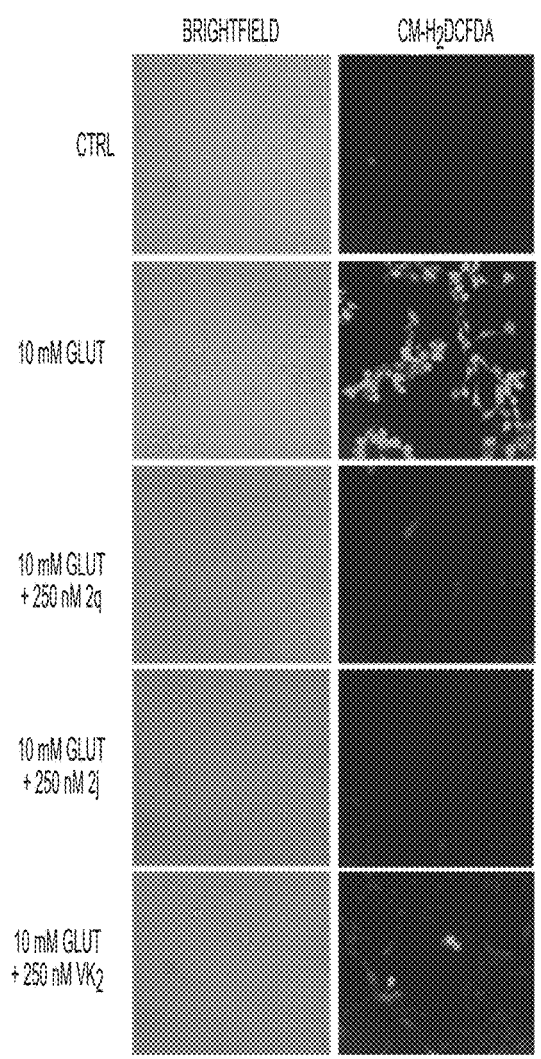

Although it has been shown that other naphthoquinones are capable of selectively inhibiting histone deacetylases (HDACs), the compounds used in this study do not possess that capacity (Inks et al., 2012). Since the first intracellular step in the initiation of the oxidative glutamate induced cell death is the depletion of GSH via the blockade of cystine import through the cystine/glutamate antiporter (Albrecht, 2010), the compounds were first tested to determine if they had any effect on the depletion of GSH. VK$_2$, compounds 2q and 2j, Necrostatin-1 (Nec-1, inhibitor of necroapoptosis via inhibition of RIP1 kinase; only inhibits extrinsic death signaling), Idebenone (Ideb, synthetic coenzyme Q10 antioxidant), and Trolox (chemical antioxidant), did not prevent the depletion of GSH, even when treated at levels much higher than required for cellular protection (FIG. 2A and FIG. 15). GSH depletion due to exposure of high concentration of glutamate results in the accumulation and production of reactive oxygen species (ROS). According to reports, and consistent with other experimental data, this occurs in a time dependent manner. There is an initial linear increase in ROS that parallels GSH depletion over approximately the first four hours of glutamate treatment followed by a sharp, exponential increase in ROS that occurs between six and eight hours (Tan et al., 2001; Murphy et al., 1989). Thus the compounds were tested to determine if they were able to prevent ROS accumulation after eight hours of glutamate treatment. At concentrations consistent with their protective capacity, $VK_2$ and compounds 2q and 2j completely prevented the accumulation of intracellular ROS, with 2q and 2j being more effective at lower concentrations (FIGS. 2B and 2C).

The possibility of a direct antioxidant interaction between the compounds and ROS was examined. To evaluate the antioxidant potential of the compounds, the ability of the compounds to quench the stable free radical 2,2-diphenyl-1-picrylhydrazyl (DPPH), a widely applied free radical scavenging assay, was tested (Blois, 1958; Molyneux, 2003). In the presence of VK2 or compounds 2q or 2j, at concentrations far exceeding those needed for cellular protection, the optical absorbance of a solution of DPPH remained constant, while the known antioxidants Trolox and ascorbic acid rapidly scavenged DPPH, as evidenced by the loss of DPPH absorbance (FIG. 3A).

The data presented thus far indicates that the protective activity of $VK_2$ and the derivatives occurs intracellularly and downstream of the cystine/glutamate antiporter and the depletion of GSH, is mediated by the inhibition of the accumulation of intracellular ROS, and does not occur via a direct free radical scavenging interaction. This indicates that the protection is likely a result of the activation of an endogenous intracellular antioxidant response, the interference with a critical component of a cell death signaling pathway, or the inhibition of the production of ROS.

A major mechanism by which cells defend themselves against oxidative stress is through the increased expression of genes whose protein products are involved in the removal of ROS (Nguyen et al., 2009). Potential activation of the antioxidant response by $VK_2$ and compounds 2q and 2j was evaluated using qRT-PCR to measure the mRNA levels of two of the antioxidant response genes, heme oxygenase 1 (HO-1) and NAD(P)H:quinone oxidoreductase (NQO-1) (Reichard et al., 2007). While treatment with glutamate significantly increased the expression of HO-1 and NQO-1, co-treatment with $VK_2$ and compounds 2q and 2j decreases HO-1, but not NQO-1, expression relative to the glutamate only treatment. However, even with this decrease, HO-1 levels in the drug and glutamate co-treatment conditions were still significantly higher than controls. (FIG. 3B). Since $VK_2$ and its analogs contain a naphthoquinone moiety, it is interesting to note that NQO-1 is not up-regulated by treatment with $VK_2$, 2q, or 2j, indicating theses naphthoquinones are not likely to be substrates of NQO-1 and do not elicit phase 2 detoxification enzyme up-regulation. This data suggests that while the cellular antioxidant response is intact in HT22 cells; it is insufficient to prevent glutamate induced cell death, and the decreased activation in the co-treated cells reflects a lessening of overall cellular oxidative stress.

In order to investigate the hypothesis that protection is mediated by the inhibition of the production of ROS, attempts were made to identify the source of the glutamate-induced ROS. Mitochondria are a major source of cellular ROS, primarily through the generation of mitochondrial superoxide, which is produced as a normal byproduct of oxidative phosphorylation. Mitochondrial dysfunction and subsequent increases in mitochondrial superoxide production have been implicated as important preceding events that ultimately result not only in the glutamate-induced cell death in HT22 cells (Fukui et al., 2009), but also in several disease states, including neurodegenerative diseases such as Parkinson's, Alzheimer's, and amyotrophic lateral sclerosis (ALS) (Lin and Beal, 2006), and brain injuries such as stroke and traumatic brain injury that are associated with cerebral hypoxia and ischemia (Ten and Starkov, 2012; Sims and Muyderman, 2010; Lifshitz et al., 2003). Mitochondrial dysfunction in cell death is characterized by a decline in mitochondrial membrane potential, respiratory defects, an increase in ROS production, changes in ATP levels, and the release of apoptogenic factors, including cytochrome c and apoptosis-inducing factor (Kroemer and Reed, 2000). Increased mitochondrial superoxide generation and mitochondrial fragmentation occurs in HT22 cells exposed to high levels of extracellular glutamate, and co-treatment with $VK_2$, 2q, or 2j, prevented these events (FIG. 4). This result is consistent with the recent discovery of the ability of eukaryotic cells to use $VK_2$ as an alternative electron carrier that is capable of alleviating mitochondrial complex defects due to gene mutations, thereby reducing ROS generation from the electron transport chain (ETC) (Vos et al., 2012).

In light of the findings that the protection against glutamate induced cell death provided by $VK_2$, 2q, and 2j, are at least partially mediated by the attenuation of the increased production of endogenous ROS, the inventors also examined the effects of these compounds on tert-butylhydroperoxide (t-BuOOH) induced cell death. t-BuOOH is a short chain analog of the lipid hydroperoxides formed from peroxidation reactions during oxidative stress that is cytotoxic to cells (Lemasters and Nieminen, 1997). $VK_2$, 2q, and 2j are capable of protecting HT22 cells from t-BuOOH, while the antioxidants Trolox and co-enzyme Q10 are less effective (FIG. 17). This result indicates that a specific molecular pathway is also involved in this protection. Emerging evidence indicates that mitochondrial fission and fragmentation, a process in which the thread-like, tubular mitochondrial networks are split into small, isolated organelles, plays an active role in cell death. It is well documented that cells undergo rapid and extensive fragmentation in the early stages of cell death (Bossy-Wetzel et al., 2003; Frank et al., 2001; Breckenridge et al., 2008; Jagasia et al., 2005; Lee et al., 2004). Recent studies have shown that mitochondrial fragmentation is regulated by the translocation of dynamin-related protein 1 (Drp1) from the cytosol to the mitochondria, where it assembles to form spirals at division sites (Smirnova et al., 2001). Although the exact molecular mechanism is still not well studied, the activity of Drp1 is regulated by the phosphorylation and dephosphorylation of specific serine residues by protein kinases and phosphatases such as calcineurin and the PGAM5 (Wang et al., 2012; Chang et al., 2007). PGAM5 was recently identified as a key signaling protein at the convergent point of multiple cell death pathways, and silencing of PGAM5 prevents cell death caused by stimulation of both extrinsic (Tumor necrosis factor-α and Fas ligand) and intrinsic pathways (t-BuOOH and calcium ionophore) (Wang et al., 2012). It has also been indicated that inhibition of this pathway is capable of preventing cell death in vitro and providing neuroprotection in vivo with a potentially extended therapeutic window (Grohm et al., 2012; Degterev et al., 2005). Since $VK_2$, 2q, and 2j were able to protect HT22 cells from both glutathione depletion and t-BuOOH induced cell deaths, the inventors chose to investigate whether $VK_2$ and the synthesized derivatives were able to affect this specific mitochondrial death pathway and maintain mitochondrial homeostasis. When exposed to high levels of glutamate for 16 hours, phosphorylation of Drp1 at serine residue 637 decreased considerably. Co-treatment with $VK_2$ at 500 nM completely prevented this de-phosphorylation. Co-treatment with the derivatives, at much lower concentrations (125 nM), was also able to maintain Drp1 phosphorylation (FIG. 5A). The effects of the compounds on cellular PGAM5 and its levels are interesting. In response to glutamate treatment, a dramatic increase in the lower band of PGAM5 occurred. This response is similar to the tumor necrosis factor-alpha induced necroapoptotic response, and the lower band is thought to be a cleavage product of the PGAM5-L isoform (Wang et al., 2012). Furthermore, this increase is completely attenuated by VK2 at 500 nM and compounds 2q and 2j at 125 nM.

Chronic Toxicity Evaluation

Preliminary in vivo toxicity was assessed for compounds 2q and 2j in mice. Although the compounds exhibit nanomolar efficacy in vitro, because of their complete lack of in vitro toxicity, the inventors chose to use very high, chronic doses (50 mg/kg) for preliminary in vivo toxicity evaluation. Adult mice were injected intraperitoneally (i.p.) daily. During the course of their treatments, animals exhibited no weight loss or outward signs of pain or distress. After three weeks of chronic, high dose injections, animals were sacrificed and standard blood count and chemistry analyses performed. All measured parameters of the treatment groups were consistent with those of the vehicle control group (Tables 6 and 7), indicating that there is not likely to be any blood or major organ toxicity associated with chronic, high does i.p. administration of these compounds.

TABLE 6

Mouse Blood Chemistry Results.

| Parameter | Units | Vehicle Control | | Compound 2q (50 mg/kg; 3 wks i.p.) | | |
|---|---|---|---|---|---|---|
| | | 1 | 2 | 1 | 2 | 3 |
| ALP | U/L | 90 | 79 | 72 | 80 | 60 |
| ALT | U/L | 35 | 32 | 34 | 28 | 33 |
| AST | U/L | 60 | 50 | 89 | 71 | 78 |
| Total Bilirubin | mg/dL | 0.20 | 0.20 | 0.20 | 0.20 | 0.20 |
| Total Protein | g/dL | 4.9 | 5.0 | 5.2 | 5.3 | 4.9 |
| Albumin | mg/dL | 2.9 | 2.8 | 3.0 | 3.2 | 2.8 |
| Creatinine | mg/dL | 0.23 | 0.15 | 0.16 | 0.23 | 0.18 |
| BUN | mg/dL | 18 | 17 | 19 | 19 | 20 |
| Glucose | mg/dL | 199 | 219 | 195 | 205 | 195 |

TABLE 7

Mouse Complete Blood Count Results.

| Parameter | Units | Vehicle Control | | Compound 2q (50 mg/kg; 3 wks i.p.) | | |
|---|---|---|---|---|---|---|
| | | 1 | 2 | 1 | 2 | 3 |
| Leukocytes | | | | | | |
| WBC | K/uL | 7.00 | 10.58 | 9.28 | 8.82 | 6.62 |
| NE | K/uL | 1.56 | 4.38 | 5.55 | 3.03 | 3.78 |
| LY | K/uL | 4.78 | 4.50 | 3.30 | 5.14 | 2.45 |
| MO | K/uL | 0.64 | 1.51 | 0.32 | 0.43 | 0.35 |
| EO | K/uL | 0.02 | 0.13 | 0.10 | 0.17 | 0.01 |
| BA | K/uL | 0.01 | 0.07 | 0.01 | 0.05 | 0.02 |
| Erythrocytes | | | | | | |
| RBC | M/uL | 9.70 | 4.44 | 9.39 | 9.46 | 9.37 |
| Hb | g/dL | 14.8 | 16.0 | 13.9 | 14.5 | 13.9 |
| HCT | % | 54.6 | 24.6 | 51.1 | 53.2 | 51.3 |
| MCV | fl | 56.3 | 55.4 | 54.4 | 56.2 | 54.8 |
| MCH | pg | 15.3 | 36.0 | 14.8 | 15.3 | 14.8 |
| MCHC | g/dL | 27.1 | 65.0 | 27.2 | 27.3 | 27.1 |
| RDW | % | 17.6 | 24.2 | 17.8 | 17.7 | 17.4 |
| Thrombocytes | | | | | | |
| PLT | K/uL | 988 | 690 | 1139 | 946 | 1050 |
| MPV | fl | 4.6 | 4.8 | 4.5 | 4.6 | 4.4 |

Using the Zebrafish PTZ-Induced Epilepsy Model to Screen HDAC Inhibitors and VK Analogs for Effectiveness Against Seizures A panel of HDAC inhibitors with different HDAC isozyme inhibition profiles were examined including VPA as a positive control. The NOEC of each inhibitor was established in six days post fertilization (dpf) zebrafish larvae (Table 8). The panel of HDAC inhibitors were then screened at their NOEC for potential anti-convulsant activity in PTZ-treated zebrafish. Groups of eight larvae were pretreated with each HDAC inhibitor 1 hr prior to induction of seizures by PTZ. Seizure activities were measured based on 4 criteria—distance moved, duration of mobility and movement, frequency of mobility and movement, and velocity. Video was recorded for 15 minutes using the Daniovision instrument and analyzed with Ethovision software. PTZ-treated larvae traveled approximately three times the distance traveled by tank water (TW) only zebrafish larvae (FIG. 6B). Interestingly, NQN-1 was the only one HDAC inhibitor other than VPA that exhibited anti-seizure effects (Table 8 and FIG. 6). VPA and NQN-1 significantly suppressed seizures in terms of distance traveled and degree of seizure activity (FIG. 6B). NQN-1 effectively suppressed PTZ-induced seizures to levels comparable to VPA induced suppression and TW only levels. However, the concentration of NQN-1 required for effective reduction of seizures (3 μM) is more than 1000-fold less than the required concentration of VPA (4 mM). Interestingly, none of the other HDAC inhibitors tested exhibited anti-seizure effects (Table 8), which suggests that either HDAC inhibition is not the molecular target for VPA and NQN-1, or the molecular mechanism(s) are far more complicated and involve multiple pathways that are consistent with previous hypotheses reported. Furthermore, the inventors did not observe an inhibition of PTZ-induced seizures with pre-treatment of the hydroxamic version of VPA, VPHA, which was shown previously to reduce seizures in rodents (Table 8) (Gravemann et al., 2008).

TABLE 8

HDAC inhibitors tested on the zebrafish seizure model.

| HDAC Inhibitors | HDAC Class of Inhibition | NOEC for antiseizure activity (mM) | Seizure suppression |
|---|---|---|---|
| Valproic Acid (VPA) | 1, 2, 3, 8 | 4000 | Yes |
| Suberoylanilide hydroxamic acid (SAHA) | 1, 2, 3, 6, 8 | 15 | No |
| Diphenyl acetic hydroxamic acid (dPAHA) | 4, 5, 7, 8, 9 | 7.5 | No |
| 2-Benzoylamino-1,4-naphthoquinone (NQN-1) | 6 | 3 | Yes |
| Tubastatin A (Tub A) | 6, 8 | 12 | No |
| 2-propylpentane hydroxamic acid (VPHA) | 4, 5, 7, 8 | 50 | No |

VK3 Pretreatment Reduces PTZ-Induced Seizures in 6 dpf Zebrafish

As NQN-1 could effectively be used to reduce seizure activity to levels comparable to VPA treatment, the NQN-1 chemical structure was examined more closely. NQN-1 contains a central naphthoquinone moiety, which is the central core motif of many natural products. Most notably it is the central structure for Vitamin K. Thus, Vitamins $K_1$, $K_2$ and $K_3$ as well as several readily available analogues containing a central naphthoquinone were tested. Vitamins $K_1$ and $K_2$ did not appear to have a toxic dose when up to 100 mM was used in the toxicity assay, but neither were found to reduce seizures even at these high concentrations. However, $VK_3$ displayed a dose dependent decrease in seizure activity and was effective at reducing seizure activity to levels comparable to VPA treatment, at much lower concentrations than VPA (1.5-6 µM $VK_3$ with highest NOEC at 10 µM compared to 4 mM VPA). A dose response to $VK_3$ inhibition of PTZ-induced seizures was observed (FIG. 7).

Pretreatment with VK3 Analogues Reduced Seizures Slightly Below the Maximum Tolerated Dose A set of $VK_3$ analogues were synthesized and showed in a parallel study that these $VK_3$ analogues were highly neuroprotective with effective concentrations in the low nano-molar range. Since seizures commonly result in neuronal injury and permanent disability, their anti-seizure potential in the zebrafish model of epilepsy were examined. These new compounds were observed to be as effective as VPA at reducing seizure activity in terms of distant traveled (FIG. 8). Furthermore, these new compounds had significantly higher no observed effect concentration (NOEC) and were not toxic to zebrafish embryos and larvae. Interestingly, only those analogues with an allylic amine and an open Michael acceptor were observed to reduce seizure activity in PTZ-treated zebrafish larvae.

VK Analog, 2q, Penetrates Blood-Brain Barriers and is Present in Mice Brains $VK_2$ is synthesized in situ where it is needed. One hypothesis of $VK_2$ did not halt the seizure activity is due to its lack of bioavailability under treatment via tank water. Utilizing small synthetic VK analog that can perform similarly to $VK_2$ is of novelty for epileptic treatment. Mice were under I.P. daily injection of 2q for three weeks and their brains were harvested 2 hours after the final injection. The mouse brains were extracted with organic solvent. The presence and the level of 2q were determined using LC-MS techniques (FIG. 9). The presence of 2q was detected via mass spectrometry in the mice brain 2 hours after i.p. injections.

Conclusions

In summary, the inventors started with the natural product $VK_2$, which has an emerging role in brain function and health, and systematically generated a number of derivatives which exhibited neuroprotective activity at low nanomolar concentrations and that demonstrated no in vitro neurotoxicity. The naphthoquinone core was confirmed to be the structural motif responsible for the neuroprotective activity and an amine substitution at the 2' carbon greatly enhanced the protective activity. The further addition of a benzyl group to the 2' amine improved the safety index of the compound by completely abolishing any in vitro neurotoxicity, and chloro-substitution at the meta position of the aromatic ring further improved the protective potency of the compound.

The efforts to investigate the mechanism by which $VK_2$ and its derivatives provide their protection against oxidative stress led to the discovery that both $VK_2$ and the disclosed derivatives prevent the dysregulation of mitochondrial function under injurious conditions, potentially via their ability to influence the critical PGAM5-Drp1 mitochondrial death signaling pathway. Without wishing to be bound by any theory, based on the shared naphthoquinone motif and evidence that eukaryotic cells are able to use $VK_2$ for this purpose (Vos et al., 2012), it is possible that the disclosed compounds are preventing stress induced mitochondrial dysfunction and subsequent ROS generation by acting as enhanced or alternative electron carriers, although why this parallel mechanism of electron transfer chain exists and why it seems to function more efficiently under injurious conditions requires further investigation.

A study by Sekine et al. identified the key protease, Presenilins-associated rhomboid-like protease (PARL), which is responsible for the activation and cleavage of PGAM5. Without wishing to be bound by any theory, these results support the idea that $VK_2$, 2q, and 2j, are likely to act on a PARL regulatory mechanism. The study claims that PARL is activated by mitochondrial membrane depolarization, which would be consistent with the inventors' mitochondrial dysfunction hypothesis, although the exact mechanism of PARL activation in this situation is still unclear.

Several VK analogs for potential therapeutic agents against epilepsy have been characterized that do not appear to be teratogenic and have no apparent toxicity at therapeutic doses in both mice and zebrafish. The mode of action of $VK_3$ and analogues in controlling seizures in epilepsy is novel—these compounds decrease seizure activity in PTZ-treated fish in a way that does not appear inhibit HDACs like VPA. VK3 and VK3-analogues were found to be just as effective as VPA in controlling seizures in zebrafish larvae treated with PTZ, at greater than 1000-fold less than is needed for VPA. Data from HT-22 cells provide evidence for a neuroprotective effect for some of these agents. These new compounds may be used to treat other neurological disorders and may be tested in other animal models. Besides providing a potentially therapeutic treatment for epilepsy, these compounds can be used as tools to provide new insights into epilepsy and the basic mechanisms underlying epileptogenesis.

Example 2

Zebrafish and Mouse Studies of Novel Compounds for Epilepsy

Methods

Chemicals

PTZ (Sigma P6500), 2-benzoylamino-1,4-naphthoquinone (NQN-1), suberoylanilide hydroxamic acid (SAHA), diphenyl acetic hydroxamic acid (dPAHA), Tubastatin A, VPA (Sigma P4543), 2-propylpentane hydroxamic acid (VPHA), and Vitamin $K_3$ (VK3) were synthesized in the laboratory or obtained from commercially available sources (Inks et al., 2012). Vitamin K analogs were synthesized according to Josey et al. (Josey et al., 2013).

Zebrafish Studies

Zebrafish (AB strain) were obtained from the Zebrafish International Resource Center (supported by P40 RR012546 from NIH-NCRR). Zebrafish were maintained and crossed according to standard methods (Westerfield, 2000). Fertilized eggs were collected and placed in E3 embryo medium and positioned in an incubator set at 28.5° C. with a 14/10 h light/dark cycle (Kimmel et al., 1995). To determine the lethal dose of each compound, 96-well plates containing one zebrafish (7 days post-fertilization, dpf) per well in 100 µL of tank water were used. 100 µL of each compound (0.5 to 15 µM) was added to each well for 12 animals (one row) for a final volume of 200 µL. One row of larvae was used as DMSO only controls. The 96-well plate was placed on a warmer at 32° C. and fish were observed for changes in phenotype, behavior and mortality initially after addition of compound, after 1 h treatment and after 5 h treatment. All zebrafish studies were approved by the Medical University of South Carolina Institutional Animal Care and Use Committee (AR #2850) and performed in accordance with the guidelines.

TABLE 9

Compounds tested in the larval zebrafish swim assay

| Compounds tested | Lethal dose (mM) | Highest concentration tested for anti-seizure activity (mM) |
|---|---|---|
| Valproic Acid (VPA) | N.D. | 4 |
| Suberoylanilide hydroxamic acid (SAHA) | >0.015 | 0.015 |
| Diphenyl acetic hydroxamic acid (dPAHA) | 0.01 | 0.0075 |
| 2-Benzoylamino-1,4-naphthoquinone (NQN-1) | 0.005 | 0.003 |
| Tubastatin A | >0.012 | 0.012 |
| 2-propylpentane hydroxamic acid (VPHA) | >0.05 | 0.05 |
| VK3 | 0.007 | 0.006 |
| 2j | 0.012 | 0.010 |
| 2h | >0.02 | 0.02 |
| 2q | >0.02 | 0.02 |
| 3n | 0.012 | 0.008 |

Induction and Monitoring of Seizures in Zebrafish

Seizures were induced in 7 dpf zebrafish larvae by addition of 15 mM PTZ as originally developed by Baraban et al. (Baraban et al., 2005). In a 48-well plate, one 7 dpf zebrafish was added per well. Larvae were dosed with each compound at a sub-lethal dose 1 h prior to PTZ treatment. Three control rows were included with each experiment—tank water only control, PTZ only and PTZ+VPA (4 mM final concentration of VPA). Seizures were induced by adding PTZ to wells to yield a final concentration of 15 mM. After 5 min, the plate was transferred to the Daniovision instrument (Noldus Information Technology) and the chamber light was turned on. After 2 min, MediaRecorder (Noldus) was used to record video for 15 min. A small number of videos were acquired 25 frames per second, but the majority of the data was acquired at the frame rate of 60 frames per second. After recording, fish were monitored visually for survival. Ethovision XT software (Noldus) was used to track the fish movement from the video images in order to calculate the total distance traveled over 15 min. These methods were similar to those used in Baraban et al. (2005), which established that the distance traveled by fish after induction of seizures by PTZ reliably reflects seizure activity. All experimental comparisons were made between animals from the same clutch.

Toxicity Studies

Using a 96-well plate, one zebrafish larva (7 dpf) was placed in each well in 100 µL of tank water. 100 µL of each compound was then added to each well for 12 animals (one row) for a final volume of 200 µL. One row of zebrafish larvae was used as DMSO only controls. The 96-well plate was then placed on a warmer plate at 32° C. and the fish were observed for changes in phenotype, behavior and mortality initially after addition of compound, after 1 h of treatment and after 5 h of treatment. Toxicity was also measured in the mouse model by the NIH Anticonvulsant Screening Program at the National Institute of Neurological Disorders and Stroke (Stables and Kupferberg, 1997), according to the established NIH experimental procedures. Compounds were delivered into mice by intraperitoneal (i.p.) injection at a dose of 100 mg/kg in sterile 5% DMSO, 95% Neobee (Josey et al., 2013). Acute toxicity was assessed by monitoring the animals for impaired neuromuscular function by placing treated mice on a rod rotating at 6 rpm. Compounds were considered toxic if the mouse fell off the rod three times in 1 min.

c-fos Gene Expression

Ten 7 dpf larvae were placed in 500 µL tank water in wells of a 48-well cell-culture plate and appropriate concentrations of drugs were added as in the behavior study (Table 9). After a 1 h pre-incubation period, PTZ was added to a final concentration of 15 mM in appropriate wells and larvae were incubated for a further 45 min. Fish were quickly euthanized by incubating the plate in an ice-water bath for 15 min. Fish were removed from each well and all liquid removed before freezing at −80° C. RNA was extracted using Trizol (Invitrogen) followed by the RNeasy Mini kit (Qiagen). Frozen embryos were homogenized in 800 µL Trizol using in-tube pestles and a motorized homogenizer. Following a 5-min incubation at room temperature, 200 µL chloroform was added and the samples were centrifuged at 12,000 g for 10 min. The aqueous phase was transferred to a new tube and 250 µL 100% ethanol was added and the samples mixed. This mixture was then transferred to the Qiagen minicolumn assembly and the protocol followed as described with the kit. Samples were eluted in 30 µL RNase free water and concentration was determined using the Nanodrop instrument (Thermo Fisher). cDNA was prepared using the RETROscript kit (Ambion) with 500 ng total RNA. cDNA was then diluted 1:1 with sterile $dH_2O$ and 2.5 µL of this cDNA was used in the QPCR reaction with SsoAdvanced SYBR Green Supermix (BioRad) and c-fos primers designed to span an intron-exon junction (c-fos F: CACTGCAAGCTGAAACTGACC, SEQ ID NO:9; c-fos R: GCGGCGAGGATGAACTCTAA, SEQ ID NO:10) (300 mM each) in the BioRad CFX96 RealTime instrument. L13a and EF1a gene expression were used for normalization (Rahn et al., 2013). The following cycle conditions were used: 95° C./3 min, 40 cycles of 95° C./15 s, 62° C./30 s, followed by 95° C. 30 s and a dissociation curve. Samples were run in duplicate. The $2^{-\Delta\Delta C_t}$ method was used to quantify gene expression, whereby all gene $C_t$ values were first normalized to $C_t$ values of the geometric mean of the $C_t$ of L13a and EF1a (Livak and Schmittgen, 2001). Treated samples were then normalized to the tank water control and converted to fold change.

Mouse Studies

Mouse studies were performed by NIH Anticonvulsant Screening Program at the National Institute of Neurological Disorders and Stroke (Stables and Kupferberg, 1997) according to the established NIH experimental procedures outlined below. Compounds were delivered into mice by i.p. injection at a dose of 100 mg/kg in sterile 5% DMSO, 95% Neobee (Josey et al., 2013). One of four methods for seizure induction was subsequently administered to mice at 0.25, 0.5, 1, 2 and 4 h after treatment with compound. (1) Subcutaneous PTZ seizure threshold test. PTZ was administered at a concentration of 85 mg/kg, into the loose fold of skin in the midline of the neck. Mice were observed for 30 min for presence or absence of seizure (White et al., 1995). Mice were considered protected if they did not have clonic spasms (lasting approximately 3-5 s). (2) Maximal electroshock test. 60 Hz of 50 mA alternating current was delivered for 0.2 s by corneal electrodes. Mice were considered protected from seizures when the hindlimb tonic extensor was absent (White et al., 1995). (3) Minimal clonic seizure (6 Hz) test. 6 Hz of 32 mA or 44 mA alternating current was delivered for 3 s by corneal electrodes to elicit a psychomotor seizure. Mice were considered protected from seizures when the automatistic behaviors were absent (Barton et al., 2001). (4) Corneal kindled mouse model. Mice were kindled electrically with a 3 s stimulation, 8 mA, 60 Hz, and corneal electrodes to a criterion of 10 consecutive Stage 5 seizures (facial clonus and head nodding progressing to forelimb clonus, and finally rearing and falling accompanied by a generalized clonic seizure as described by Racine, 1972). Animals generally reach Stage 5 after twice daily stimulation for 8 days. With continued stimulation once a day, animals usually progressed to a reproducible Stage 5 after 10-14 additional days. At least 72 hours after the mice were kindled, the test substance was administered i.p. and each animal was given the electrical stimulus indicated above. Following stimulation, the animals were observed for the presence or absence of the rearing and falling criteria of a Stage 5 seizure. Treated animals not displaying a Stage 4 or 5 seizure were considered protected.

Cell Culture

HT-22 neurons were grown in Dulbecco's Modified Eagle's Medium (DMEM/high glucose) supplemented with 10% fetal bovine serum and 1% of antibiotic-antimycotic (Invitrogen) at 37° C. in 5% $CO_2$. The HT-22 neuronal cell line is a subclone of the HT4 cell line, derived from mouse hippocampus (Morimoto and Koshland, 1990).

Respirometry

Oxygen consumption rates (OCR) and extracellular acidification rates (ECAR) of HT-22 neuronal cells were performed on the XF-96 Extracellular Flux Analyzer (Seahorse Bioscience) using standard methods (Beeson et al., 2010). In brief, cells were cultured in 96 well Seahorse plates in DMEM high glucose media (Invitrogen) supplemented with 10% FBS, 10 mM HEPES, and 1% antibiotic-antimycotic (Invitrogen). The media was replaced with DMEM media supplemented with 25 mM glucose, 10 mM sodium pyruvate, 31 mM NaCl, and 2 mM glutamine at pH 7.4. Each of the four drug ports on the Seahorse sensor cartridge were filled with test compound (media only, 5 µM NQN-1, 10 µM VK3 or 12.5 µM MB), 10 µM oligomycin, 1 µM FCCP, and 5 µM rotenone, which were injected into each well at 20, 80, 110, and 135 min, respectively. The pmol/min OCR rate for each well (9-52 wells/group) was measured. Wells were excluded from the analysis if their OCR values surpassed the Tukey Outlier Rule. In order to standardize the OCR rates across wells, the average OCR value at 17 min (last time point prior to injection of the test compounds) for each experimental group was calculated, and set to 100. All OCR values are given as a percentage of this pre-treatment value. All OCR values are reported as a percentage of each group's standard value.

Fluorometric ATP Assay

Cellular ATP levels were determined using a fluorometric ATP assay (BioVision). HT-22 cells were pretreated for 8 h with media only, 5 or 10 µM NQN-1, 5 or 10 µM VK3, or 12.5 µM MB. Cells were lysed with 100 µL ATP assay buffer, sonicated for 20 s and centrifuged at 15,000 g for 2 min at 4° C. Protein concentrations of the supernatant were determined using the Bicinchoninic acid assay. 2-4 µg of total protein lysate was used for ATP determination. A standard curve was generated with known ATP concentrations. ATP concentrations for each sample were determined and adjusted for total protein per mg lysate. Data were normalized to control samples from the respective plates.

Statistical Analyses

Statistical analyses were performed with JMP 10.0.2 software (SAS Institute). Multiple comparisons were made using a one-way ANOVA with a Kruskal-Wallis Test, followed by Dunn's Method to determine significant differences between all pairs or between control and experimental groups using the Dunn Method for Joint Ranking. Differences were considered statistically significant when $p<0.05$. Data are represented as means±standard error of the mean (SEM).

Results and Discussion

NQN-1 Reduced Distance Traveled in PTZ-Treated Zebrafish Larvae

Because VPA had been shown to inhibit HDAC activity (Phiel et al., 2001), other HDAC inhibitors as a potential new class of anti-epileptic drugs were explored. A panel of HDAC inhibitors (SAHA, dPAHA, NQN-1, Tubastatin A and VPHA) with different HDAC isozyme inhibition profiles (Tessier et al., 2009, Bradner et al., 2010, Butler et al., 2010, Fass et al., 2010) were selected for study in the zebrafish model. The toxicity of these compounds on 7 dpf zebrafish larvae was tested and determined the highest sub-lethal dose for each (Table 9). A pre-treatment experimental protocol was established in order to more accurately model the effectiveness of these drugs in preventing the initiation of seizures. Zebrafish larvae (7 dpf) were treated with the selected compounds at the determined sub-lethal concentrations for 1 h prior to inducing seizures with PTZ. Similar to previous larval zebrafish epilepsy studies, total distance traveled after seizures by each fish was measured and used as a proxy for seizure activity. FIG. 10B shows representative traces of swimming behavior of individual zebrafish beginning 5 min after administration of PTZ to each well, and the total distance traveled (shown normalized to the control) for 15 min are given in FIG. 10C. The swim behavior traces clearly show that compared to the control animal, PTZ induces a robust increase in total distance traveled by the fish (FIG. 10B, FIG. 10C). Compared to the average control distance, treatment with PTZ induced a significant 4-fold increase in total distance traveled (p<0.0001; FIG. 10B, FIG. 10C). VPA was included as a positive control and as previously shown by Baraban et al. (2005), VPA significantly reduced distance traveled compared to PTZ alone (p=0.0007) and to a level indistinguishable from control (p=1.0). Of the five HDAC inhibitors tested in this initial screen, only NQN-1 significantly suppressed PTZ-induced swim activity in zebrafish, reducing the seizure-associated swimming to a level not significantly different from the untreated control levels (p=0.2113; FIG. 10B, FIG. 10C). The concentration of NQN-1 required to reduce swim levels in PTZ-treated fish was 1300 times less than the required concentration of VPA (Table 9). Neither VPA nor NQN-1 alone significantly altered the swimming behavior (distance traveled) of the fish compared to controls (p=1.0 and p=1.0, respectively; FIG. 10B, FIG. 10C). None of the other HDAC inhibitors tested reduced swim activity.

The larval fish treated with the compounds were more closely evaluated to correlate the measure of seizures with a molecular marker for neuronal activity. C-fos expression has been shown to increase with seizure activity and was used previously to validate this zebrafish model of epilepsy (Baraban et al., 2005). A new quantitative real-time PCR assay was developed to measure c-fos gene expression in pools of zebrafish rather than in single fish as has been previously reported. PTZ treatment shows increased c-fos expression 80-fold over control and that pre-treatment with VPA or NQN-1 was able to blunt this increase in expression. Treatment with VPA or NQN-1 alone did not increase c-fos expression to this extent (FIG. 10D).

VK3 Reduced PTZ-Induced Swim Activity in 7 dpf Zebrafish.

Because NQN-1 reduced swim activity to levels comparable to VPA treatment, the inventors looked more closely at its chemical structure. NQN-1 contains a central naphthoquinone moiety, which is the core motif of many natural products, but most notably it is the central structure for VK3 (FIG. 11A). After first determining the highest non-lethal dose (Table 9), VK3 was tested in the zebrafish assay and demonstrated a robust inhibition of the PTZ-induced seizure swim behavior at the highest tolerated dose (6 µM) as seen in the traces of the total distance traveled for representative fish (FIG. 11B) and the normalized distance traveled (FIG. 11C). 6 µM VK3 reduced distance traveled after PTZ treatment more than 4-fold to a level not significantly different from the untreated control swim levels (p=1.0). C-fos gene expression was also reduced by approximately 10-fold compared to PTZ alone after pre-treatment with VK3 (FIG. 11D). Declining activity of VK3 was found with reduction in dose (FIG. 11B, 11C). At 3 µM VK3, the PTZ-induced swim behavior was reduced 2-fold, which was not significantly different from control levels (p=0.5038) or the PTZ levels (p=0.0996). Treating the fish with 1.5 µM VK3 only reduced distance traveled 0.5 fold from PTZ levels and was not significant from PTZ alone (p=1.0). These data indicate that while both 3 µM and 6 µM VK3 were effective at blocking PTZ-induced seizure behavior in zebrafish, only the higher dose reduced the seizure behavior to control levels. VK3 was tested without PTZ and no significant changes in swim activity were seen compared to control. Additionally, c-fos expression was not increased to the levels observed with PTZ treatment confirming that VK3 alone neither acts as a sedative nor increases swim activity.

Vitamin K Analogs Reduced PTZ-Induced Swim Activity in Zebrafish Larvae.

VK3 and NQN-1 were effective in reducing PTZ-induced swimming in zebrafish, but testing revealed toxicity at higher concentrations (Table 9). In order to find new compounds that might be equally active but without this observed toxicity, several new Vitamin K analogs (FIG. 12A) (Josey et al., 2013) were developed. The highest non-lethal dose in zebrafish for these compounds was determined for each of the compounds (Table 9). Compounds 2h and 2q did not display any toxicity at the concentrations tested, however compounds 2j and 3n did display some toxicity although at higher doses than for VK3 and NQN-1.

These analogs were tested for activity in PTZ-treated zebrafish. Traces of the total distance traveled of an untreated control animal, animals exposed to Vitamin K analogs alone, to PTZ alone, and to the Vitamin K analogs in combination with PTZ are shown in FIG. 3B. Quantification of PTZ-evoked swim behavior is shown in FIG. 12C. No differences in the total distance traveled were detected when the fish were treated with any of the Vitamin K analogs alone (FIG. 12C). Two compounds did however significantly reduce PTZ-induced swim activity 2.5-3 fold (2 h n=8; p=0.0018 and 2j n=16; p=0.0221). Of these two analogs, only 2 h reduced the induced swimming to a level indistinguishable from untreated controls (p=1.0); the distance traveled of fish treated with the 2j analog was significantly greater than control levels (p=0.001). Compounds 2q and 3n, although reducing the distance traveled after PTZ treatment more than two fold, did not reach statistical significance compared to PTZ levels (2q n=8; p=0.3 and 3n n=16; p=0.06). However, compound 2q did reach levels similar to control (p=0.08) where 3n remained different from control (p=0.0004). Together these data indicate that compound 2h was most effective at suppressing PTZ-induced seizure behavior, reducing distance traveled by more than half compared to PTZ alone, to a level comparable to control levels. c-fos gene expression were also examined and show that 2h, 2j, 2q, and 3n all reduced c-fos gene expression by about half, compared to PTZ alone. Use of these compounds in the absence of PTZ did not elicit a large change in c-fos expression (FIG. 12D).

VK3 and NQN-1 Increased Overall Respiration and Mitochondrial ATP Turnover.

Previous work has shown that Vitamin K increases electron transport and oxidative phosphorylation by acting as an alternative mitochondrial electron carrier in the electron transport chain (Vos et al., 2012). This suggests that Vitamin K could increase ATP production, and by extension potentially explain its anti-seizure activity. Using Seahorse extracellular flux technology, the inventors analyzed the effects of 2j, NQN-1 and VK3, on the mitochondrial function of mouse hippocampal HT-22 cells. Additionally MB was examined; another antiepileptic drug (AED) shown to act as an alternate electron acceptor (Wen et al., 2011, Pelgrims et al., 2000, Furian et al., 2007). The Seahorse technology allows measurement of oxygen consumption rates (OCR) in real time and with application of specific chemical inhibitors of enzyme complexes of the electron transport chain (ETC), detailed analysis of aspects of cellular respiration can be quantified. The basal cellular respiration is the OCR after treatment with 2j, VK3, NQN-1 or MB for 1 h and is shown as the difference in OCR from control (FIG. 13A). Compared to the respiration levels of untreated control cells, addition of VK3 (21.57±0.97; p<0.0001, n=38), NQN-1 (24.35±1.03; p<0.0001, n=19), and MB (53.21±5.92; p<0.0001, n=18) each significantly increased total cellular respiration. The addition of 2j (−4.14±2.9; p=1.0, n=25) did not significantly alter total cellular respiration of the cells compared to untreated control levels (FIG. 13, A).

Calculating the difference between basal respiration values and those after exposure to oligomycin, an inhibitor of the ATP synthase (complex V of the ETC), reveals OCR linked to ATP levels. FIG. 13, panel B, shows significantly higher levels of ATP-linked respiration from the cells exposed to VK3 (12.2±3.12; p=0.0034), NQN-1 (16.83±1.83; p=0.0001), and MB (19.76±6.59; p=0.0002) compared to untreated cells. ATP-linked respiration for cells treated with compound 2j was elevated but not significantly different to controls (6.58±3.28; p=0.068) (FIG. 13B).

Rotenone, a complex I inhibitor of the ETC, was used to show the level of OCR that is linked to non-mitochondrial respiration, thus allowing the to calculate the OCR specifically resulting from mitochondrial respiration (basal respiration minus non-mitochondrial respiration). FIG. 13C shows significantly higher levels of basal mitochondrial respiration in cells exposed to 2j (9.09±3.13; p=0.035), NQN-1 (15.26±2.29; p=0.0008), and MB (19.22±6.54; p=0.0017). VK3 mitochondrial respiration was elevated but failed to reach statistical significance (p=0.0684).

Using the extracellular flux analyzer it is also possible to measure extracellular acidification rates (ECAR, a measure of glycolysis). ECAR levels from cells treated with VK3 (1.89±0.93; p=0.25), NQN-1 (1.75±1.12; p=0.5) or MB (−0.86±1.26; p=1.00) were not different from untreated control cells, however cells treated with 2j (5.03±1.11; p=0.0002) showed significantly increased basal acidification rates (FIG. 13D).

These data reveal that the compounds VK3, NQN1 and MB increase overall cellular respiration, and ATP-linked mitochondrial respiration. This suggests that these compounds may be increasing mitochondrial complex activity, as observed with MB (Wen et al., 2011) and Vitamin K (Vos et al., 2012), in turn potentiating mitochondrial energy production in these cells. The data also suggest that while not changing overall cellular respiration rates, compound 2j may drive cells toward glycolysis as shown by the ECAR rates.

VK3, NQN-1 and MB Alter Total Cellular ATP.

The compounds found to be active at reducing swim activity were hypothesized to act on total ATP levels. To follow up on the respiration experiments, total cellular ATP levels in the HT-22 cells were measured using a fluorometric method. Addition of VK3, NQN-1 or MB significantly increased total cellular ATP levels 22-28% above control levels (n=7-13) (FIG. 14).

Novel Vitamin K Analogs Reduced Seizures in Mouse Models of Epilepsy.

Compounds 2j, 2h and 2q were sent to the Anticonvulsant Screening Program at the National Institute of Neurological Disorders and Stroke (NIH), to test for anti-epileptic activities in four different mouse models of epilepsy. Pretreatment with 2j, 2h or 2q (100 mg/kg) had no effect on PTZ-induced seizures in mice. However, all three compounds showed anti-epileptic activity with the 6 Hz model at 32 mA (Table 11) with the most promising compound being 2h, with 100% protection against 6 Hz seizures at 32 mA at 0.25 h. The 2j and 2q analogs also had some antiseizure activity. Additional testing of 2h with the 6 Hz model at 44 mA did not result in any protection. There was some limited anti-epileptic activity for 2j and 2h with the maximal electroshock test (Table 13). Further testing was performed using 2h with the kindled mouse model and this compound showed activity protecting 2/4 mice from seizures (Table 12). No or low acute toxicity was observed in mice treated with 100 mg/kg of each compound, as assessed by rotorod assay (Table 10). Previously, mice had been treated with compounds 2j and 2q at 50 mg/kg i.p. daily for 3 weeks and did not observe any blood or major organ toxicity (Josey et al., 2013).

There is a great need for new therapeutics for epilepsy as many patients still suffer symptoms and the current pharmaceuticals do not work for all patients. In general, potential AEDs are tested on adult rodents, however since 70% of epilepsy occurs in childhood, there is a precedent for screening potential AEDs in younger animals, in addition to adults (Loscher and Schmidt, 2011). Use of the well-established zebrafish model of epilepsy allows both needs to be addressed by utilizing a high-throughput assay on larval fish.

This study initially began by following up on the observation that VPA can act as a histone deacetylase (HDAC) inhibitor and the inventors initially hypothesized that activity against HDACs might be a mode of action for VPA and other AEDs. While several known HDAC inhibitors were tested, only one HDAC inhibitor, NQN-1, was effective at reducing swimming distance traveled (a measurement of seizure activity) to VPA-levels, at a concentration 1300 times lower than VPA. In addition to reducing the swim activity, NQN-1 (as well as VPA) reduced c-fos gene expression further validating the use of swim activity as a measure of seizures in this model. None of the other HDAC inhibitors tested reduced PTZ-induced swim activity, including VPHA, which is the hydroxamic version of VPA that was previously shown to reduce seizures in rodents (Gravemann et al., 2008). Additionally, the success of the disclosed VK3 analog compounds did not correlate with HDAC inhibitory activity as each analog inhibited different classes of HDACs or did not inhibit HDACs at all. This suggests that HDAC inhibition is not the molecular target for anti-seizure activity of these compounds.

The core structure of NQN-1 is a naphthoquinone similar to Vitamin K. The inventors hypothesized that VK3 may exhibit similar activity to what was observed with NQN-1. VK3 was tested using the described zebrafish model and showed that VK3 at 6 μM reduced PTZ-induced swim activity to control levels and the level of swim activity inhibition was dose dependent (FIG. 11). VK3 also reduced c-fos gene expression from PTZ treatment alone. VK3 has been noted to exhibit toxicity, and indeed toxicity was noticed in the larval zebrafish. Because of this toxicity several Vitamin K analogs were developed and tested. Several of these analogs could reduce seizure activity in zebrafish to levels comparable to VPA and reduced c-fos gene expression; in addition they were effective without the toxicity observed with higher concentrations of VK3.

Although not clearly understood, one important contributing factor to the occurrence of seizures may be the high energy demands of the nervous system. Because neurons have a low capacity to store ATP, any reduction in ATP levels can increase neuronal excitability, which may contribute to seizures (Bindoff and Engelsen, 2011). Neurons are thus heavily reliant on mitochondria, the major source of ATP in the cell (Bindoff and Engelsen, 2011). Additionally, defects in Complex I of the mitochondrial electron transport chain (ETC) are often observed in patients with epilepsy (Waldbaum and Patel, 2010) further implicating the mitochondria and ATP production in the pathology of epilepsy. The widely used AED VPA can act as a substrate for beta-oxidation thereby increasing mitochondrial ATP production (Lheureux and Hantson, 2009). MB, another AED, can improve mitochondrial ATP production by acting as an alternative electron acceptor (Pelgrims et al., 2000; Furian et al., 2007). The mechanism of action for VK3, NQN-1, and the other analogs, was hypothesized to involve altering or enhancing mitochondrial energy production. A Seahorse Extracellular Flux Analyzer was utilized to gauge mitochondrial function by measuring oxygen consumption rates (OCR) in HT-22 hippocampal neurons treated with 2j, VK3, NQN-1 or MB. VK3 and NQN-1 showed similar respirometric changes as MB; an increase in total OCR, an increase in ATP turnover, and an increase in mitochondrial respiration in NQN1 and 2j (FIG. 13A-C) was observed. Evidence has been provided that VK3 is a potent mitochondrial electron carrier that can restore electron flow and mitochondrial ATP production in cardiomyocytes after hypoxia or mitochondrial respiratory chain inhibition (Shneyvays et al., 2005). Without wishing to be bound by any theory, this data supports the idea that VK3 may have similar actions in neurons as MB, by acting as an alternative mitochondrial electron carrier which may increase mitochondrial complex activity resulting in greater ATP production as the inventors observed (FIG. 13). VK3, MB and NQN-1 did not increase ECAR (FIG. 13D), supporting the idea that the elevated ATP levels measured are due to increased mitochondrial oxidative phosphorylation, and not glycolysis. Interestingly, 2j did increase glycolysis (FIG. 13D) and mitochondrial respiration, but did not significantly increase ATP-linked respiration or basal cellular respiration. Researchers had previously identified in a nutrient sensitized screen that VK3 could also shift cellular energy metabolism to glycolysis (Gohil et al., 2010). Although this metabolic switch with VK3 in HT-22 cells was not observed, an increase in glycolysis with compound 2j was observed, which could be a potential mechanism for the analogs.

Recent data showed that the Vitamin K analogs that reduced seizure activity in PTZ-treated zebrafish were also highly neuroprotective in glutamate-treated HT-22 neurons, with effective concentrations in the low nanomolar range (Josey et al., 2013). Glutamate toxicity is a hallmark of seizures, and these data suggest that a related potential mechanism of the disclosed compounds is in protecting neurons against mitochondrial free radical generation, maintaining mitochondrial structure and reducing cell death (Josey et al., 2013).

The currently disclosed Vitamin K analogs were tested for anticonvulsant activity in mouse seizure models. All compounds (2j, 2h, 2q) showed good anticonvulsant activity in the minimal clonic (6 Hz) test at 32 mA (Table 11), whereas compounds 2j and 2h showed limited anticonvulsant activity in the maximal electroshock test (Table 13). Compound 2h did not protect against seizures in the minimal clonic (6 Hz) test at 44 mA. Compound 2h was further tested in a corneal kindled mouse model and showed protection in 2 of 4 mice (Table 12). Each compound at 100 mg/kg showed no toxicity in mice (Table 10), and previous studies showed that 50 mg/kg injected i.p. daily in mice for three weeks was not toxic (Josey et al., 2013). Compound 2h displays significant promising potential and may be used as an AED. This compound and other compounds disclosed herein may be further tested, e.g., in chronic seizure models and testing in hippocampal slices.

Table 10 shows evaluation of mouse neurotoxicity after i.p. injection of 100 mg/kg compound. The compound is considered toxic if the animal falls off the rotorod three times during a 1 min period. The data for each treatment is represented as the number of animals displaying toxic effects/number of animals tested.

TABLE 10

Evaluation of Mouse Neurotoxicity

| Time (hr) | 0.25 | 0.5 | 1.0 | 2.0 | 4.0 |
|---|---|---|---|---|---|
| 2j | 0/12 | 0/12 | 0/12 | 0/12 | 0/12 |
| 2h | 0/12 | 1/12 | 0/12 | 0/12 | 0/12 |
| 2q | 0/12 | 0/12 | 0/12 | 0/12 | 0/12 |

Table 11 shows results from the minimal clonic seizure (6 Hz) test obtained using the following protocol. 6 Hz of 32 mA or 44 mA alternating current was delivered for 3 s by corneal electrodes to elicit a psychomotor seizure. Mice were considered protected from seizures when the automatistic behaviors were absent (Barton et al., 2001). Pre-administration of test compounds (100 mg/kg) to mice via i.p. injection protects against minimal clonic seizures (6 Hz). The data for each treatment is represented as the number of animals protected/number of animals tested.

TABLE 11

Minimal clonic seizure (6 Hz) test

| Time (h) | 0.25 | 0.5 | 1.0 | 2.0 | 4.0 |
|---|---|---|---|---|---|
| 2j | 0/4 | 0/4 | 1/4 | 1/4 | 1/4 |
| 2h | 4/4 | 2/4 | 1/4 | 1/4 | 0/4 |
| 2q | 1/4 | 0/4 | 1/4 | 0/4 | 0/4 |

The minimal clonic seizure (6 Hz) test is generally used to assess a agent's efficacy against electrically-induced seizures but uses a lower frequency (6 Hz) and longer duration of stimulation (3s) shock. Test compounds are pre-administered to mice via i.p. injection. Individual mice are challenged with sufficient current delivered through corneal electrodes to elicit a psychomotor seizure in 97% of animals (32 mA for 3s). Untreated mice will display seizures characterized by a minimal clonic phase followed by stereotyped, automatistic behaviors described originally as being similar to the aura of human patients with partial seizures. Animals not displaying this behavior are considered protected. Animals may also be evaluated using stimulation of 22 or 44 mA.

Table 12 shows results from the corneal kindled mouse model obtained using the following protocol. Mice were kindled electrically with a 3 s stimulation, 8 mA, 60 Hz, and corneal electrodes to a criterion of 10 consecutive Stage 5 seizures (facial clonus and head nodding progressing to forelimb clonus, and finally rearing and falling accompanied by a generalized clonic seizure as described by Racine, 1972). Animals generally reach Stage 5 after twice daily stimulation for 8 days. With continued stimulation once a day, animals usually progressed to a reproducible Stage 5 after 10-14 additional days. At least 72 hours after the mice were kindled, the test substance was administered i.p. and each animal was given the electrical stimulus indicated above. Following stimulation, the animals were observed for the presence or absence of the rearing and falling criteria of a Stage 5 seizure. Treated animals not displaying a Stage 4 or 5 seizure were considered protected. Pre-administration of test compound (100 mg/kg) to mice via i.p. injection shows protection against seizures in a corneal kindled mouse model. The data for each treatment is represented as the number of animals protected (N)/number of animals tested (F).

TABLE 12

| Cpd | Time (hrs) | N/F | Individual Seizure Scores | Avg seizure score |
|---|---|---|---|---|
| 2h | 0.25 | 2/4 | 3, 3, 4, 5 | 3.75 |

Table 13 shows maximal electroshock-induced seizures obtained using the following protocol. Pre-administration of test compounds (100 mg/kg) to mice via i.p. injection shows protection against maximal electroshock-induced seizures. The data for each treatment is represented as the number of animals protected/number of animals tested.

The maximal electroshock-induced seizures (MES) test is a model for generalized tonic-clonic seizures and provides an indication of a compound's ability to prevent seizure spread when all neuronal circuits in the brain are maximally active. These seizures are highly reproducible and are electrophysiologically consistent with human seizures. An animal is considered "protected" from MES-induced seizures based on abolition of the hindlimb tonic extensor component of the seizure.

TABLE 13

| Maximal Electroshock-induced Seizures: | | | | | |
|---|---|---|---|---|---|
| Time (hr) | 0.25 | 0.5 | 1.0 | 2.0 | 4.0 |
| 2j | 0/4 | 0/4 | 0/4 | 2/4 | 0/4 |
| 2h | 0/4 | 0/4 | 0/4 | 1/4 | 1/4 |
| 2q | 0/4 | 0/4 | 0/4 | 0/4 | 0/4 |

Example 3

Synthesis of Compounds

Synthesis of 2-Amino Derivatives: Standard Procedure

To a solution of 2-bromo-1,4-naphthoquinone (283 mg, 1.2 mmol, 1.0 equiv) in abs EtOH (50 mL) was added an excess of the corresponding amine (2.4 mmol, 2 equiv, unless otherwise stated), and the reaction was stirred at room temperature and monitored by TLC. Most reactions were complete within 10 minutes. While some reactions precipitated pure product which was collected by vacuum filtration, others required chromatographic purification.

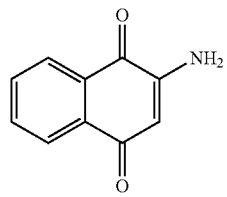 [SMILES: NC1=CC(=O)c2ccccc2C1=O]

2-amino-1,4-naphthoquinone (1d)

6.25 g $NaN_3$ was dissolved in 15 mL $H_2O$ and acidified with 5 mL glacial acetic acid. The $NaN_3$ solution was added to a solution of 1,4-naphthoquinone (5 g, 29 mmol) dissolved in 100 mL of $THF/H_2O$ (4:1) and stirred at room temperature. After 6 hrs, the reaction was concentrated in vacuo and redissolved in ethyl acetate. The resulting solution was washed with 1 M NaOH and saturated NaCl. Multiple extractions were required. The extracts were combined, dried with $MgSO_4$, and concentrated in vacuo. The reddish brown residue was purified by column chromatography (silica gel, 50% v/v ethyl acetate/hexane) to yield 4.8 g fluffy bright orange crystals 1d (96% yield). MS m/z calcd (M+) 173.05, found 173.04. 1H NMR (400 MHz, DMSO-d6) Shift 7.94 (dd, J=7.15, 19.70 Hz, 2H), 7.82 (dt, J=1.00, 7.53 Hz, 1H), 7.69-7.76 (m, 1H), 5.82 (s, 1H).

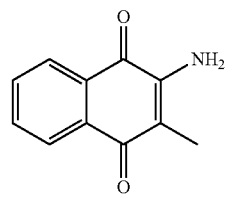

2-amino-3-methyl-1,4-naphthoquinone (1e)

Dissolved 2-methyl-1,4-naphthoquinone (560 mg, 3.3 mmol) in methanol (30 mL) and placed under inert atmosphere. Dissolved 1.37 g $NaN_3$ in 10 mL water and acidified to pH 4 (83 drops of 12 M HCl). Added sodium azide solution to reaction flask and slowly heated reaction to 50° C. and then stirred for 5 hrs. Reaction was quenched with water and extracted with ethyl acetate (2×) The organic layers were combined and washed with saturated NaCl solution, dried with $Mg_2SO_4$, and concentrated in vacuo. The reaction was purified on silica gel eluting with ethyl acetate and hexane (3:7) to yield 423 mg orange powder 1e (69% yield). MS m/z calcd (M+) 188.07, found 188.04. 1H NMR (400 MHz, DMSO-d6) Shift 7.96-8.03 (m, 2H), 7.83 (dt, J=1.25, 7.53 Hz, 1H), 7.71-7.78 (m, 1H), 6.86 (s, 2H), 1.97 (s, 3H). C13-HSQC (400 MHz, DMSO-d6) Shift 0.53, 28.28, 9.45, 39.58, 132.22, 125.73, 134.80, 125.94, 125.93, 134.81.

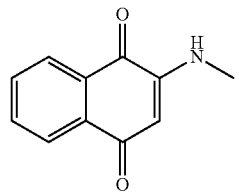

2-(methylamino)naphthalene-1,4-dione (2a)

To a solution of 2-bromo-1,4-naphthoquinone (283 mg, 1.2 mmol) in abs EtOH (40 mL) was added and excess of aqueous methylamine solution (40%, 207 uL, 2.3 mmol). The reaction was stirred for 10 min at rt, then concentrated in vacuo and purified on silica gel eluting with ethyl acetate and hexane to yield 116 mg reddish orange powder (52% yield). MS m/z calcd (M+) 188.2, found 188.2. 1H NMR (400 MHz, DMSO-d6) Shift 7.97 (dd, J=7.40, 13.93 Hz, 2H), 7.84 (dt, J=1.13, 7.47 Hz, 1H), 7.64-7.78 (m, 2H), 5.61 (s, 1H), 2.80 (d, J=5.02 Hz, 3H). C13-HSQC (400 MHz, DMSO-d6) Shift 38.88, 27.43, 99.25, 131.78, 134.75, 125.53.

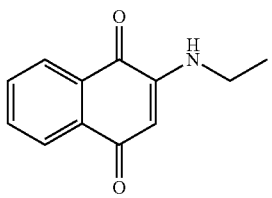

2-(ethylamino)naphthalene-1,4-dione (2b)

Ethylamine HCl (196 mg, 2.4 mmol, 2 equiv) and K$_2$CO$_3$ (331 mg, 2.4 mmol, 2 equiv) were dissolved in water (3 mL) and added to a solution of 2-bromo-1,4-naphthoquinone (283 mg, 1.2 mmol, 1 equiv) dissolved in abs EtOH (40 mL). Reaction stirred at rt for 10 min, then concentrated in vacuo and purified on silica gel eluting with ethyl acetate and hexane to yield 142 mg brown powder (59% yield). MS m/z calcd (M+) 202.02, found 202.1. 1H NMR (400 MHz, DMSO-d6) Shift 7.96-8.07 (m, 2H), 7.88 (dt, J=1.13, 7.47 Hz, 2H), 7.74-7.82 (m, 1H), 7.61 (br. s., 1H), 5.73 (s, 1H), 3.27 (quin, J=6.90 Hz, 2H), 1.23 (t, J=7.28 Hz, 3H). C13-HSQC (400 MHz, DMSO-d6) Shift 12.33, 39.17, 36.12, 98.94, 132.18, 134.92, 125.17.

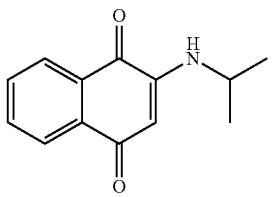 [SMILES: CC(C)NC1=CC(=O)c2ccccc2C1=O]

2-(isopropylamino)naphthalene-1,4-dione (2d)

To a solution of 2-bromo-1,4-napthoquinone (283 mg, 1.2 mmol) in abs EtOH (40 mL) was added an excess of isopropylamine (206 uL, 2.4 mmol). The reaction was stirred for 10 min at rt, then concentrated in vacuo and purified on silica gel eluting with ethyl acetate, followed by reverse phase purification on C18 silica to yield 240 mg bright orange powder (47% yield). 1H NMR (400 MHz, DMSO-d6) d 7.92-8.04 (m, 2H), 7.80-7.90 (m, 1H), 7.70-7.76 (m, 1H), 7.18 (d, J=8.28 Hz, 1H), 5.71 (s, 1H), 1.22 (d, J=6.40 Hz, 6H). C13-HSQC (400 MHz, DMSO-d6) (ppm) 21.52, 39.70, 43.86, 99.93, 132.64, 135.19, 125.63, 126.32.

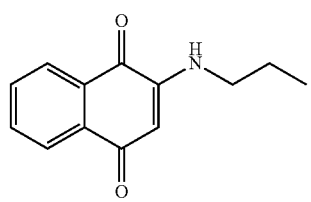 [SMILES: CCCNC1=CC(=O)c2ccccc2C1=O]

2-(propylamino)naphthalene-1,4-dione (2e)

To a solution of 2-bromo-1,4-napthoquinone (283 mg, 1.2 mmol) in abs EtOH (40 mL) was added an excess of propylamine (197 uL, 2.4 mmol). The reaction was stirred at rt for 10 min, then concentrated in vacuo and purified on silica gel eluting with ethyl acetate and hexane to yield 178 mg bright orange powder (69% yield). 1H NMR (400 MHz, DMSO-d6) Shift 7.92-8.03 (m, 2H), 7.84 (dt, J=1.00, 7.53 Hz, 1H), 7.70-7.77 (m, 1H), 7.60 (br. s., 1H), 5.69 (s, 1H), 3.15 (q, J=6.53 Hz, 2H), 2.51 (s, 7H), 1.60 (sxt, J=7.28 Hz, 2H), 0.91 (t, J=7.40 Hz, 3H). C13-HSQC (400 MHz, DMSO-d6) Shift (ppm) 11.13, 11.12, 20.15, 39.58, 43.39, 98.90, 131.88, 134.94, 131.87, 134.93, 131.87, 125.26.

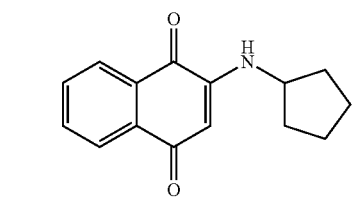 [SMILES: O=C1C=C(NC2CCCC2)C(=O)c2ccccc21]

2-(cyclopentylamino)naphthalene-1,4-dione (2f)

To a solution of 2-bromo-1,4-napthoquinone (283 mg, 1.2 mmol) in abs EtOH (40 mL) was added an excess of cyclopentylamine (237 uL, 2.4 mmol). The reaction was stirred at rt for 10 min, then concentrated in vacuo and purified on silica gel eluting with ethyl acetate and hexane to yield 225 mg red powder (39% yield). MS m/z calcd (M+) 242.29, found 242.1. 1H NMR (400 MHz, DMSO-d6) Shift 7.97 (dd, J=7.40, 15.43 Hz, 2H), 7.84 (t, J=7.03 Hz, 1H), 7.69-7.78 (m, 1H), 7.26 (d, J=7.03 Hz, 1H), 5.70 (s, 1H), 3.71-3.94 (m, 1H), 1.86-2.08 (m, 2H), 1.61-1.78 (m, 4H), 1.49-1.61 (m, 2H). C13-HSQC (400 MHz, DMSO-d6) Shift (ppm) 10.97, 20.36, 39.48, 43.30, 98.96, 131.81, 125.61, 134.87, 131.89, 125.03, 125.03, 134.86, 125.86, 131.80.

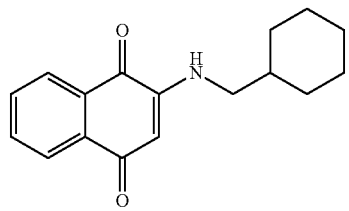 [SMILES: O=C1C=C(NCC2CCCCC2)C(=O)c2ccccc21]

2-((cyclohexylmethyl)amino)naphthalene-1,4-dione (2g)

To a solution of 2-bromo-1,4-napthoquinone (283 mg, 1.2 mmol) in abs EtOH (40 mL) was added an excess of cyclohexanemethylamine (312 uL, 2.4 mmol). Progress of the reaction was monitored with TLC. Compound was purified using chromatography on silica gel to yield 124 mg orange powder (38% yield).). MS m/z calcd (M+) 270.34, found 270.1. 1H NMR (400 MHz, DMSO-d6) Shift 7.97 (dd, J=7.03, 17.57 Hz, 2H), 7.83 (dt, J=1.00, 7.53 Hz, 1H), 7.70-7.77 (m, 1H), 7.64 (t, J=6.15 Hz, 1H), 5.68 (s, 1H), 3.04 (t, J=6.53 Hz, 2H), 1.50-1.81 (m, 6H), 1.05-1.32 (m, 3H), 0.81-1.03 (m, 2H). C13-HSQC (400 MHz, DMSO-d6) Shift (ppm) 30.82, 25.66, 26.58, 25.66, 30.82, 6.40, 40.14, 48.34, 99.47, 132.52, 135.19, 125.62, 126.34.

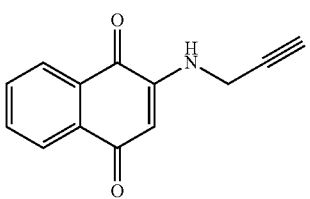 [SMILES: C#CCNC1=CC(=O)c2ccccc2C1=O]

2-(prop-2-yn-1-ylamino)naphthalene-1,4-dione (2h)

To a solution of 2-bromo-1,4-napthoquinone (283 mg, 1.2 mmol) in abs EtOH (40 mL) was added an excess of propargylamine (154 uL, 2.4 mmol). Compound was purified using chromatography on silica gel eluting with ethyl acetate and hexane to yield 103 mg fuzzy golden brown crystals (20% yield). MS m/z calcd (M+) 212.22, found 212.1. 1H NMR (400 MHz, DMSO-d6) Shift 7.94-8.03 (m, 2H), 7.81-7.88 (m, 2H), 7.73-7.79 (m, 1H), 5.79 (s, 1H), 4.05 (dd, J=2.51, 6.02 Hz, 2H), 3.29 (t, J=2.45 Hz, 1H). C13-HSQC (400 MHz, DMSO-d6) Shift F1 (ppm) 31.03, 39.73, 75.10, 79.28, 101.64, 125.76, 125.91, 126.12, 126.13, 132.79, 135.37, 135.37, 148.45, 153.90.

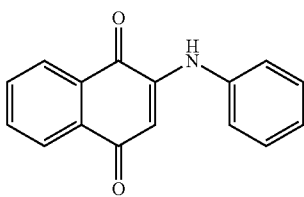 [SMILES: O=C1C=C(Nc2ccccc2)C(=O)c2ccccc21]

2-(phenylamino)naphthalene-1,4-dione (2i)

To a solution of 2-bromo-1,4-napthoquinone (283 mg, 1.2 mmol) in abs EtOH (40 mL) was added an excess of propargylamine (154 uL, 2.4 mmol). Compound was purified using chromatography on silica gel to yield 103 mg fuzzy golden brown crystals (20% yield).). MS m/z calcd (M+) 212.22, found 212.1. 1H NMR (400 MHz, DMSO-d6) Shift 7.94-8.03 (m, 2H), 7.81-7.88 (m, 2H), 7.73-7.79 (m, 1H), 5.79 (s, 1H), 4.05 (dd, J=2.51, 6.02 Hz, 2H), 3.29 (t, J=2.45 Hz, 1H). C13-HSQC (400 MHz, DMSO-d6) Shift (ppm) 21.52, 39.70, 43.86, 99.93, 132.64, 135.19, 125.63, 126.32.

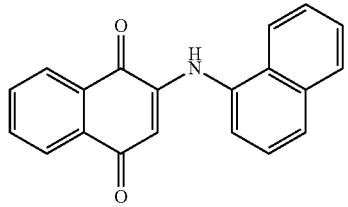 [SMILES: O=C1C=C(Nc2cccc3ccccc23)C(=O)c2ccccc21]

2-(naphthalen-1-ylamino)naphthalene-1,4-dione (2j)

To a solution of 2-bromo-1,4-napthoquinone (283 mg, 1.2 mmol) in abs EtOH (40 mL) was added an excess of 1-naphthylamine (343 mg, 2.4 mmol). Compound was purified using chromatography on silica gel eluting with ethyl acetate and hexane, followed by reverse phase purification on C18 silica to yield 6.5 mg greyish purple powder (1% yield). MS m/z calcd (M+) 300.32, found 300.2. 1H NMR (400 MHz, DMSO-d6) Shift 7.96-8.18 (m, 4H), 7.31-7.55 (m, 6H), 7.26 (d, J=7.53 Hz, 1H), 7.03-7.15 (m, 1H), 6.57 (s, 1H). C13-HSQC (400 MHz, DMSO-d6) Shift F1 (ppm) 39.58, 111.14, 107.15, 136.19, 112.78, 129.34, 128.11, 126.58, 124.96, 126.58, 126.58, 133.99, 126.58, 125.32, 121.82.

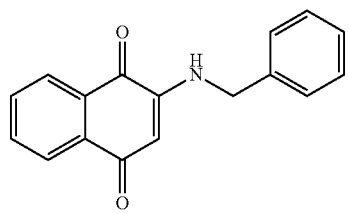 [SMILES: O=C1C=C(NCc2ccccc2)C(=O)c2ccccc21]

2-(benzylamino)naphthalene-1,4-dione (2k)

To a solution of 2-bromo-1,4-naphthoquinone (5 g, 21.1 mmol) in minimum amount of abs EtOH was added an excess benzylamine (4.6 mL, 42.2 mmol, 2 equiv). The reaction was stirred for 10 min at rt, then briefly concentrated in vacuo until copious amounts of orange precipitate were visible. the solution was then cooled to 4° C. and vacuum filtered to yield 3.5 g fluffy bright orange crystals (59% yield). MS m/z calcd (M+) 264.1, found 264.1. 1H NMR (400 MHz, DMSO-d6) Shift 8.22 (t, J=6.40 Hz, 1H), 8.01 (d, J=7.03 Hz, 1H), 7.87-7.94 (m, 1H), 7.82 (dt, J=1.13, 7.47 Hz, 1H), 7.70-7.77 (m, 1H), 7.31-7.40 (m, 4H), 7.22-7.30 (m, 1H), 5.57 (s, 1H), 4.46 (d, J=6.53 Hz, 2H). C13-HSQC (400 MHz, DMSO-d6) Shift (ppm) 39.62, 45.48, 100.68, 127.64, 129.05, 127.63, 132.36, 135.20, 125.67, 126.37.

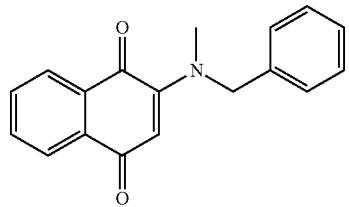 [SMILES: CN(Cc1ccccc1)C1=CC(=O)c2ccccc2C1=O]

2-(benzyl(methyl)amino)naphthalene-1,4-dione (2l)

To a solution of 2-bromo-1,4-napthoquinone (283 mg, 1.2 mmol) in abs EtOH (40 mL) was added an excess of N-benzylmethylamine (310 uL, 2.4 mmol). Compound was taken up onto Celite and purified using chromatography on silica gel eluting with ethyl acetate and hexane to yield 230 mg bright orange powder (69% yield). MS m/z calcd (M+) 278.11, found 278.1. 1H NMR (400 MHz, DMSO-d6) Shift 7.87-7.97 (m, 2H), 7.81 (dt, J=1.28, 7.43 Hz, 1H), 7.70-7.78 (m, 1H), 7.33-7.41 (m, 2H), 7.30 (d, J=6.97 Hz, 3H), 5.85 (s, 1H), 4.85 (s, 2H), 3.08 (s, 3H). C13-HSQC (400 MHz, DMSO-d6) Shift (ppm) 39.73, 40.38, 56.81, 106.52, 127.31, 128.99, 129.08, 127.31, 133.02, 134.48, 124.91, 126.76, 134.48.

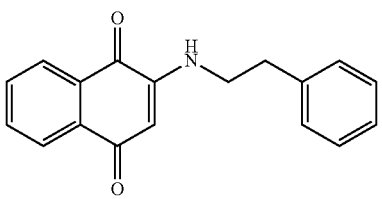 [SMILES: O=C1C=C(NCCc2ccccc2)C(=O)c2ccccc21]

2-((3-phenethylpropyl)amino)naphthalene-1,4-dione
(2m)

To a solution of 2-bromo-1,4-napthoquinone (283 mg, 1.2 mmol) in abs EtOH (40 mL) was added an excess of phenethylamine (302 uL, 2.4 mmol). The reaction was stirred for 30 min at rt and the precipitate filtered to yield 90 mg bright orange powder (27% yield). MS m/z calcd (M+) 278.32, found 278.4. 1H NMR (400 MHz, DMSO-d6) Shift 7.96 (dd, J=7.78, 14.31 Hz, 1H), 7.69-7.88 (m, 2H), 7.56 (t, J=5.77 Hz, 1H), 7.15-7.41 (m, 5H), 5.75 (s, 1H), 3.26-3.54 (m, 2H), 2.99-3.14 (m, 1H), 2.81-2.98 (m, 2H). C13-HSQC (400 MHz, DMSO-d6) Shift (ppm) 33.55, 33.55, 39.77, 43.57, 43.57, 100.01, 125.71, 126.27, 126.77, 129.01, 132.64, 135.24.

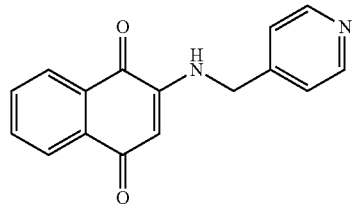 [SMILES: O=C1C=C(NCc2ccncc2)C(=O)c2ccccc21]

2-((pyridin-4-ylmethyl)amino)naphthalene-1,4-dione
(2n)

To a solution of 2-bromo-1,4-napthoquinone (283 mg, 1.2 mmol) in abs EtOH (40 mL) was added an excess of 4-picolylamine (243 uL, 2.4 mmol). Compound was purified using chromatography on silica gel, followed by C18 silica gel, to yield 87.8 mg yellow powder (28% yield). MS m/z calcd (M+) 264.1, found 264.1. 1H NMR (400 MHz, DMSO-d6) Shift 8.74 (d, J=5.27 Hz, 2H), 8.27 (t, J=6.53 Hz, 1H), 8.04 (d, J=6.78 Hz, 1H), 7.89-7.95 (m, 1H), 7.84 (dt, J=1.13, 7.47 Hz, 1H), 7.73-7.80 (m, 3H), 5.56 (s, 1H), 4.69 (d, J=6.53 Hz, 2H). C13-HSQC (400 MHz, DMSO-d6) Shift (ppm) 39.83, 43.80, 101.07, 123.72, 123.72, 125.35, 125.93, 132.32, 134.90, 145.16.

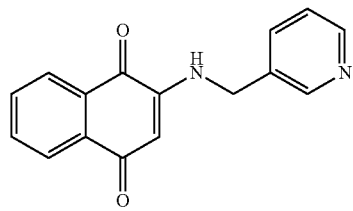 [SMILES: O=C1C=C(NCc2cccnc2)C(=O)c2ccccc21]

2-((pyridin-3-ylmethyl)amino)naphthalene-1,4-dione
(2o)

To a solution of 2-bromo-1,4-napthoquinone (283 mg, 1.2 mmol) in abs EtOH (40 mL) was added an excess of 3-(aminomethyl)pyridine (244 uL, 2.4 mmol). Compound was purified using chromatography on silica gel to yield 50 mg orange powder (15% yield). 1H NMR (400 MHz, DMSO-d6) Shift 8.61 (d, J=1.76 Hz, 1H), 8.47 (dd, J=1.51, 4.77 Hz, 1H), 8.23 (t, J=6.40 Hz, 1H), 8.01 (d, J=7.03 Hz, 1H), 7.88-7.95 (m, 1H), 7.69-7.86 (m, 3H), 7.37 (dd, J=4.77, 7.78 Hz, 1H), 5.65 (s, 1H), 4.50 (d, J=6.53 Hz, 2H). C13-HSQC (400 MHz, DMSO-d6) Shift (ppm) 39.23, 42.70, 100.63, 123.21, 132.10, 134.85, 134.84, 125.22, 125.87, 148.52, 148.52.

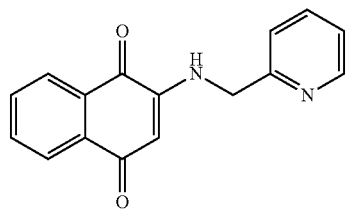 [SMILES: O=C1C=C(NCc2ccccn2)C(=O)c2ccccc21]

2-((pyridin-2-ylmethyl)amino)naphthalene-1,4-dione
(2p)

To a solution of 2-bromo-1,4-napthoquinone (283 mg, 1.2 mmol) in abs EtOH (40 mL) was added an excess of 2-picolylamine (247 uL, 2.4 mmol). The reaction was stirred for 10 minutes and then concentrated in vacuo. Compound was purified using chromatography on silica gel eluting with ethyl acetate and hexane, followed by reverse phase purification on C18 silica to yield 90 mg yellowish powder (29% yield). MS m/z calcd (M+) 265.09, found 265.1. 1H NMR (400 MHz, DMSO-d6) Shift 8.59 (br. s., 1H), 8.10 (t, J=6.05 Hz, 1H), 8.02 (d, J=7.70 Hz, 1H), 7.92 (d, J=7.70 Hz, 1H), 7.80-7.87 (m, 2H), 7.71-7.78 (m, 1H), 7.31-7.52 (m, 2H), 5.61 (s, 1H), 4.56 (br. s., 2H). C13-HSQC (400 MHz, DMSO-d6) Shift (ppm) 39.72, 46.52, 101.13, 122.49, 123.49, 125.86, 125.86, 132.62, 135.29, 138.79, 148.41.

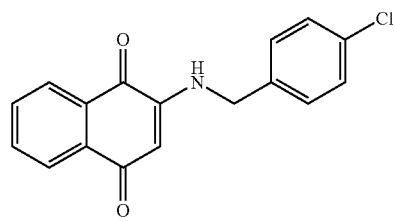 [SMILES: O=C1C=C(NCc2ccc(Cl)cc2)C(=O)c2ccccc21]

2-((4-chlorobenzyl)amino)naphthalene-1,4-dione
(2q)

To a solution of 2-bromo-1,4-napthoquinone (283 mg, 1.2 mmol) in abs EtOH (40 mL) was added an excess of 4-chlorobenzylamine (292 uL, 2.4 mmol). Progress of the reaction was monitored with TLC. Precipitate was vacuum filtered after 20 min to give 267 mg sparkly orange powder (74% yield). MS m/z calcd (M+) 298.74, found 298.8. 1H NMR (400 MHz, DMSO-d6) Shift 8.15 (t, J=6.40 Hz, 1H), 7.93 (d, J=7.03 Hz, 1H), 7.83 (d, J=6.78 Hz, 1H), 7.72-7.78 (m, 1H), 7.63-7.70 (m, 1H), 7.20-7.42 (m, 4H), 5.49 (s, 1H), 4.37 (d, J=6.53 Hz, 2H). C13-HSQC (400 MHz, DMSO-d6) Shift (ppm) 39.48, 44.11, 46.15, 100.42, 128.86, 132.53, 134.84, 125.11, 125.98.

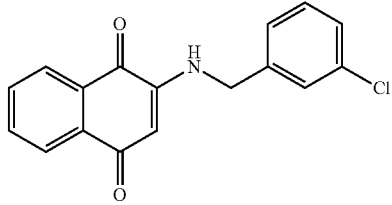 [SMILES: O=C1C=C(NCc2cccc(Cl)c2)C(=O)c2ccccc21]

2-((3-chlorobenzyl)amino)naphthalene-1,4-dione (2r)

To a solution of 2-bromo-1,4-napthoquinone (283 mg, 1.2 mmol) in abs EtOH (40 mL) was added an excess of 3-chlorobenzylamine (293 uL, 2.4 mmol). Reaction was stirred for 30 min after which the precipitated solid was filtered to yield 199 mg bright orange powder (56% yield). MS m/z calcd (M+) 298.06, found 298.1. 1H NMR (400 MHz, DMSO-d6) Shift 8.23 (t, J=6.53 Hz, 1H), 7.95-8.05 (m, 1H), 7.87-7.94 (m, 1H), 7.79-7.87 (m, 1H), 7.70-7.79 (m, 1H), 7.45 (s, 1H), 7.25-7.42 (m, 3H), 5.60 (s, 1H), 4.47 (d, J=6.53 Hz, 2H). C13-HSQC (400 MHz, DMSO-d6) Shift (ppm) 40.08, 44.86, 100.96, 125.82, 126.28, 126.48, 127.51, 127.51, 130.72, 132.58, 135.31.

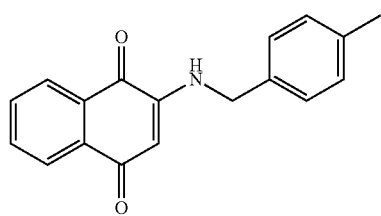 [SMILES: Cc1ccc(CNC2=CC(=O)c3ccccc3C2=O)cc1]

2-((4-methylbenzyl)amino)naphthalene-1,4-dione (2s)

To a solution of 2-bromo-1,4-napthoquinone (283 mg, 1.2 mmol) in abs EtOH (40 mL) was added an excess of 4-methylbenzylamine (306 uL, 2.4 mmol). Reaction was stirred for 40 min after which the precipitated solid was filtered to yield 187 mg (56% yield) reddish orange powder. MS m/z calcd (M+) 278.11, found 278.1. 1H NMR (400 MHz, DMSO-d6) Shift 8.25 (t, J=6.40 Hz, 1H), 8.00-8.12 (m, 1H), 7.93-8.00 (m, 1H), 7.89 (dt, J=1.00, 7.53 Hz, 1H), 7.75-7.85 (m, 1H), 7.27-7.36 (m, 2H), 7.17-7.27 (m, 2H), 5.62 (s, 1H), 4.47 (d, J=6.27 Hz, 2H), 2.34 (s, 3H). C13-HSQC (400 MHz, DMSO-d6) Shift (ppm) 20.78, 40.11, 45.39, 100.80, 129.73, 127.84, 132.56, 135.44, 125.74, 126.52.

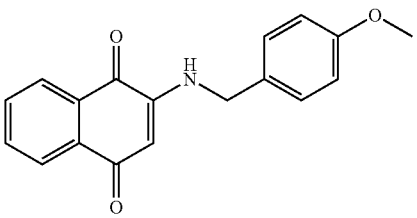 [SMILES: COc1ccc(CNC2=CC(=O)c3ccccc3C2=O)cc1]

2-((4-methoxybenzyl)amino)naphthalene-1,4-dione (2t)

To a solution of 2-bromo-1,4-napthoquinone (283 mg, 1.2 mmol) in abs EtOH (40 mL) was added an excess of 4-methoxybenzylamine (314 uL, 2.4 mmol). Reaction was stirred for 10 min after which the precipitated solid was filtered to yield 192 mg (55% yield) slightly orangish yellow powder. MS m/z calcd (M+) 294.11, found 294.0. 1H NMR (400 MHz, DMSO-d6) Shift 8.17 (t, J=6.40 Hz, 1H), 7.95-8.05 (m, 1H), 7.87-7.94 (m, 1H), 7.82 (dt, J=1.13, 7.47 Hz, 1H), 7.68-7.77 (m, 1H), 7.29 (d, J=8.53 Hz, 2H), 6.91 (d, J=8.53 Hz, 2H), 5.59 (s, 1H), 4.37 (d, J=6.53 Hz, 2H), 3.73 (s, 3H). C13-HSQC (400 MHz, DMSO-d6) Shift (ppm) 39.99, 45.03, 55.57, 100.90, 114.25, 125.77, 126.47, 129.05, 132.58, 135.43, 146.84, 152.29.

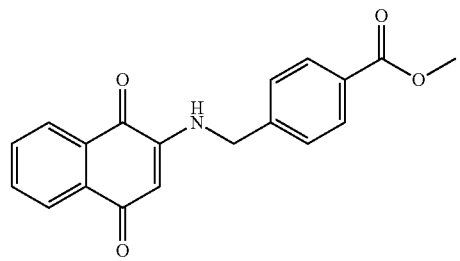 [SMILES: COC(=O)c1ccc(CNC2=CC(=O)c3ccccc3C2=O)cc1]

methyl 4-(((1,4-dioxo-1,4-dihydronaphthalen-2-yl)amino)methyl)benzoate (2u)

To a solution of 2-bromo-1,4-napthoquinone (283 mg, 1.2 mmol) in abs EtOH (40 mL) was added an excess of Methyl 4-(aminomethyl)benzoate hydrochloride (569 mg, 2.4 mmol) and K$_2$CO$_3$ dissolved in water. Reaction was stirred for 10 min after which the precipitated solid was filtered to yield 189 mg (49% yield) yellow powder. MS m/z calcd (M+) 322.1, found 322.1. 1H NMR (400 MHz, DMSO-d6) Shift 8.27 (t, J=6.40 Hz, 1H), 8.01 (d, J=7.53 Hz, 1H), 7.87-7.98 (m, 3H), 7.82 (dt, J=1.00, 7.53 Hz, 1H), 7.70-7.78 (m, 1H), 7.49 (d, J=8.03 Hz, 2H), 5.53 (s, 1H), 4.54 (d, J=6.53 Hz, 2H), 3.84 (s, 3H). C13-HSQC (400 MHz, DMSO-d6) Shift (ppm) 40.03, 45.25, 52.64, 100.97, 125.56, 126.49, 127.84, 129.87, 132.61, 135.33, 146.82, 152.19.

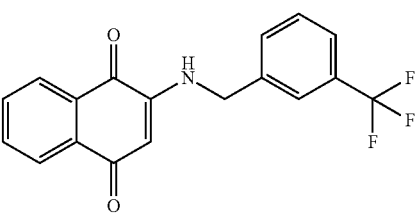 [SMILES: O=C1C=C(NCc2cccc(C(F)(F)F)c2)C(=O)c2ccccc21]

2-((3-(trifluoromethyl)benzyl)amino)naphthalene-1,4-dione (2v)

To a solution of 2-bromo-1,4-napthoquinone (283 mg, 1.2 mmol) in abs EtOH (40 mL) was added an excess of 3-(trifluoromethyl)benzylamine (420 mg, 2.4 mmol). The reaction was stirred for 10 minutes and then concentrated in vacuo. Compound was purified using chromatography on silica gel eluting with ethyl acetate and hexane to yield 397 mg yellowish powder (48% yield). MS m/z calcd (M+) 332.09, found 332.1. 1H NMR (400 MHz, DMSO-d6) Shift 8.28 (t, J=6.53 Hz, 1H), 8.01 (d, J=6.78 Hz, 1H), 7.87-7.94 (m, 1H), 7.83 (dt, J=1.13, 7.47 Hz, 1H), 7.72-7.79 (m, 2H), 7.69 (d, J=7.53 Hz, 1H), 7.54-7.67 (m, 2H), 5.64 (s, 1H), 4.56 (d, J=6.53 Hz, 2H). C13-HSQC (400 MHz, DMSO-d6) Shift (ppm) 40.22, 45.02, 100.83, 124.20, 124.21, 126.33, 126.33, 130.13, 131.76, 135.16.

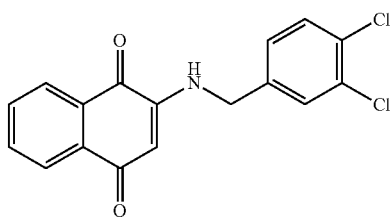 [SMILES: O=C1C=C(NCc2ccc(Cl)c(Cl)c2)C(=O)c2ccccc21]

2-((3,4-dichlorobenzyl)amino)naphthalene-1,4-dione (2w)

To a solution of 2-bromo-1,4-napthoquinone (283 mg, 1.2 mmol) in abs EtOH (40 mL) was added an excess of 3,4-dichlorobenzylamine (422 mg, 2.4 mmol). MS m/z calcd (M+) 331.02, found 331.1. 1H NMR (400 MHz, DMSO-d6) Shift 8.22 (t, J=6.53 Hz, 1H), 7.96-8.05 (m, 1H), 7.88-7.94 (m, 1H), 7.83 (dt, J=1.00, 7.53 Hz, 1H), 7.71-7.78 (m, 1H), 7.67 (d, J=1.76 Hz, 1H), 7.58-7.64 (m, 1H), 7.38 (dd, J=1.76, 8.28 Hz, 1H), 5.61 (s, 1H), 4.46 (d, J=6.53 Hz, 2H). C13-HSQC (400 MHz, DMSO-d6) Shift (ppm) 40.10, 44.37, 101.12, 125.77, 126.44, 128.13, 129.75, 130.97, 132.60, 135.26.

Synthesis of 2-amido derivatives: Standard Procedure

Reactions were carried out under argon. To a solution of Compound 1 (0.3 g, 1.7 mmol, 1 equiv) and NaH (0.2 g, 5 mmol, 60% dispersion) dissolved in tetrahydofuran (THF, 20 mL) was slowly added an excess of the corresponding acyl chloride (2.5 mmol, 1.5 equiv). Products were purified using chromatography followed by crystallization.

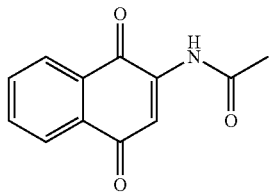 [SMILES: CC(=O)NC1=CC(=O)c2ccccc2C1=O]

N-(1,4-dioxo-1,4-dihydronaphthalen-2-yl)acetamide (3a)

0.15 g (0.88 mmol) was dissolved in 2 mL acetic anhydride along with 0.2 mL glacial acetic acid, and the reaction was refluxed overnight. The reaction was allowed to cool to room temperature and the precipitated product was filtered and crystallized from ethyl acetate and hexane to yield 156 mg of fine yellow crystals (82% yield). MS m/z calcd (M+) 216.06, found 216.1. 1H NMR (400 MHz, DMSO-d6) Shift 9.95 (s, 1H), 8.02-8.11 (m, 1H), 7.94-8.01 (m, 1H), 7.80-7.93 (m, 2H), 7.70 (s, 1H), 2.25 (s, 3H). C13-HSQC (400 MHz, DMSO-d6) Shift 25.27, 39.91, 115.96, 134.11, 125.83, 134.10, 125.82.

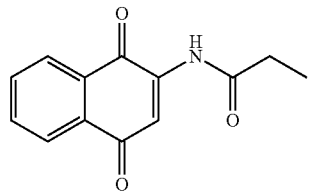 [SMILES: CCC(=O)NC1=CC(=O)c2ccccc2C1=O]

N-(1,4-dioxo-1,4-dihydronaphthalen-2-yl)propionamide (3b)

To a solution of Compound 1d (0.3 g, 1.7 mmol, 1 equiv) and NaH (0.2 g, 5 mmol, 60% dispersion) dissolved in tetrahydofuran (THF, 20 mL) was slowly added an excess of propionyl chloride chloride (267 uL, 2.5 mmol, 1.5 equiv). The reaction was stirred at room temperature for 10 minutes. The reaction was quenched with water and extracted with dichloromethane (2x), washed with 1 M NaOH, 1 M HCl, and saturated NaCl. The organic layer was dried over Mg$_2$SO$_4$ and concentrated in vacuo. Compound was purified using chromatography on silica gel eluting with ethyl acetate and hexane to yield 54 mg mg yellow powder (% yield). MS m/z calcd (M+) 229.07, found 229.9. 1H NMR (400 MHz, DMSO-d6) d ppm 1.07 (t, J=7.58 Hz, 3H) 2.61 (q, J=7.34 Hz, 2H) 7.72 (s, 1H) 7.83-7.94 (m, 2H) 7.95-8.01 (m, 1H) 8.04-8.10 (m, 1H) 9.84 (s, 1H). C13-HSQC (400 MHz, DMSO-d6) Shift (ppm) 9.23, 40.18, 30.21, 116.32, 133.92, 135.23, 125.66, 126.74.

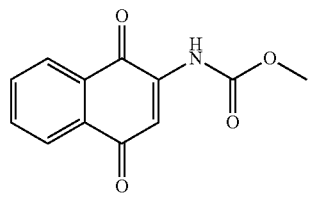 [SMILES: COC(=O)NC1=CC(=O)c2ccccc2C1=O]

methyl(1,4-dioxo-1,4-dihydronaphthalen-2-yl)carbamate (3c)

To a solution of Compound 1d (0.3 g, 1.7 mmol, 1 equiv) and NaH (0.2 g, 5 mmol, 60% dispersion) dissolved in dry DMF and placed under argon. Methylchloroformate (197 uL, 2.5 mmol, 1.5 equiv) was added slowly. Reaction stirred at rt until starting material consumed as determined by TLC. Quenched reaction with excess water and extracted with DCM (3x). Combined organic layers, dried with Mg$_2$SO$_4$, and concentrated in vacuo. An excess of water was added to the remaining dark solution from which a brown solid precipitated. This brown solid was filtered and purified using silica gel (50/50 ethyl acetate/hexane with 0.1% Et$_3$N). Crystallized with hot ethyl acetate/hexane to yield 133 mg crumbly greenish brown crystals (34% yield). 1H NMR (400 MHz, DMSO-d6) Shift 9.41 (s, 1H), 8.05 (dd, J=1.25, 7.28 Hz, 1H), 7.95-8.01 (m, 1H), 7.81-7.93 (m, 2H), 7.34 (s, 1H), 3.76 (s, 3H). C13-HSQC (400 MHz, DMSO-d6) Shift (ppm) 31.13, 40.57, 53.82, 114.98, 126.21, 127.02, 134.40.

eluting with ethyl acetate and hexane and crystallized with hot ethyl acetate and hexane to yield 83 mg mg yellow crystals (18% yield). MS m/z calcd (M+) 270.3, found 270.3. 1H NMR (400 MHz, DMSO-d6) Shift 9.75 (s, 1H), 8.06 (d, J=7.34 Hz, 1H), 7.93-8.00 (m, 1H), 7.81-7.92 (m, 2H), 7.70 (s, 1H), 3.24 (quin, J=7.61 Hz, 1H), 1.79-1.93 (m, 2H), 1.61-1.76 (m, 4H), 1.48-1.61 (m, 2H). C13-HSQC (400 MHz, DMSO-d6) Shift (ppm) 26.16, 26.17, 30.30, 30.30, 40.31, 45.48, 116.47, 125.86, 126.66, 133.66, 135.27.

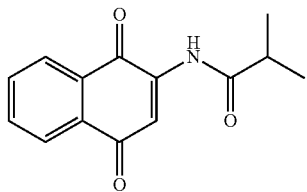 [SMILES: CC(C)C(=O)NC1=CC(=O)c2ccccc2C1=O]

N-(1,4-dioxo-1,4-dihydronaphthalen-2-yl)isobutyramide (3d)

To a solution of Compound 1d (0.3 g, 1.7 mmol, 1 equiv) and NaH (0.2 g, 5 mmol, 60% dispersion) dissolved in tetrahydofuran (THF, 20 mL) was slowly added an excess of the corresponding isobutyryl chloride (267 uL, 2.5 mmol, 1.5 equiv). The reaction was stirred at room temperature for 10 minutes. The reaction was quenched with water and extracted with dichloromethane (2×), washed with 1 M NaOH, 1 M HCl, and saturated NaCl. The organic layer was dried over Mg$_2$SO$_4$ and concentrated in vacuo. Compound was purified using chromatography on silica gel eluting with ethyl acetate and hexane and crystallized with hot ethyl acetate and hexane to yield 54 mg mg yellow crystals (13% yield). MS m/z calcd (M+) 244.26, found 244.0. 1H NMR (400 MHz, DMSO-d6) Shift 9.77 (s, 1H), 8.03-8.09 (m, 1H), 7.94-7.99 (m, 1H), 7.82-7.92 (m, 2H), 7.71 (s, 1H), 1.09 (d, J=6.97 Hz, 7H). C13-HSQC (400 MHz, DMSO-d6) Shift (ppm)

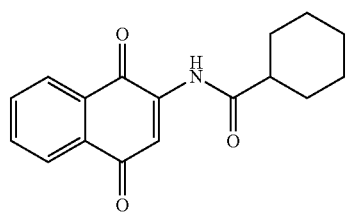

N-(1,4-dioxo-1,4-dihydronaphthalen-2-yl)cyclohexanecarboxamide (3f)

To a solution of Compound 1d (0.3 g, 1.7 mmol, 1 equiv) and NaH (0.2 g, 5 mmol, 60% dispersion) dissolved in tetrahydofuran (THF, 20 mL) was slowly added an excess of the corresponding cyclohexanecarbonyl chloride (337 uL, 2.5 mmol, 1.5 equiv). Products were purified using chromatography followed by crystallization. The reaction was stirred at room temperature for 5 minutes. The reaction was quenched with water and extracted with dichloromethane (2×), washed with 1 M NaOH, 1 M HCl, and saturated NaCl. The organic layer was dried over Mg$_2$SO$_4$ and concentrated in vacuo. Compound was purified using chromatography on silica gel eluting with ethyl acetate and hexane to yield 140 mg mg yellowish powder (29% yield). MS m/z calcd (M+) 284.3, found 384.3. 1H NMR (400 MHz, DMSO-d6) Shift 9.69 (s, 1H), 7.99 (dd, J=1.13, 7.40 Hz, 1H), 7.87-7.92 (m, 1H), 7.73-7.85 (m, 2H), 7.63 (s, 1H), 1.51-1.81 (m, 5H), 1.00-1.38 (m, 6H). C13-HSQC (400 MHz, DMSO-d6) Shift (ppm) 25.33, 25.34, 29.44, 29.44, 40.28, 44.81, 116.33, 125.82, 126.87, 134.03, 135.40.

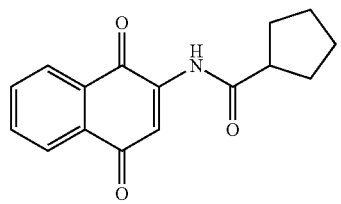 [SMILES: O=C1C=C(NC(=O)C2CCCC2)C(=O)c2ccccc21]

N-(1,4-dioxo-1,4-dihydronaphthalen-2-yl)cyclopentanecarboxamide (3e)

To a solution of Compound 1d (0.3 g, 1.7 mmol, 1 equiv) and NaH (0.2 g, 5 mmol, 60% dispersion) dissolved in tetrahydofuran (THF, 20 mL) was slowly added an excess of the corresponding cyclopentanecarbonyl chloride (300 uL, 2.5 mmol, 1.5 equiv). The reaction was stirred at room temperature for 5 minutes. The reaction was quenched with water and extracted with dichloromethane (2×), washed with 1 M NaOH, 1 M HCl, and saturated NaCl. The organic layer was dried over Mg$_2$SO$_4$ and concentrated in vacuo. Compound was purified using chromatography on silica gel

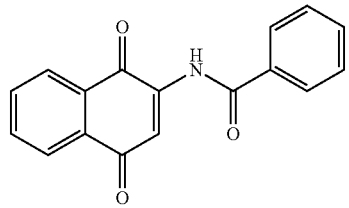 [SMILES: O=C(NC1=CC(=O)c2ccccc2C1=O)c1ccccc1]

N-(1,4-dioxo-1,4-dihydronaphthalen-2-yl)benzamide (3g)

0.3 g (1.73 mmol) 1 and 3 equiv NaH (60% dispersion, 0.2 g) were dissolved in 20 mL dry THF. To this was added 1.5 equiv. benzoyl chloride (301 μL). The reaction was quenched with water and extracted twice with DCM. The organic extracts were combined and washed sequentially with 1 M NaOH, 1 M HCl, and a saturated solution of NaCl. The extract was then dried over Mg$_2$SO$_4$ and concentrated in vacuo. The resulting powder was further purified by column chromatography (silica gel, 30/70% v/v ethyl acetate/hexane with 1% Et3N) and crystallized from ethyl acetate/hexane to yield 183 mg small, fine, bright yellow crystals (39% yield). MS m/z calcd (M+) 277.07, found 277.1. 1H NMR (400 MHz, DMSO-d6) Shift 9.74 (s, 1H), 8.10-8.15 (m, 1H), 7.87-8.07 (m, 5H), 7.79 (s, 1H), 7.67-7.74 (m, 1H), 7.57-7.65 (m, 2H).). C13-HSQC (400 MHz, DMSO-d6) Shift 126.1, 129.5, 117.0, 128.4, 40.1, 126.9, 126.1, 129.5, 117.1, 128.4, 40.1, 133.3, 129.4, 134.3, 135.3.

pound was purified using chromatography on silica gel eluting with ethyl acetate and hexane and crystallized with hot dichloromethane to yield 67 mg fluggy greenish yellow crystals (13% yield). MS m/z calcd (M+) 312.72, found 312.7. 1H NMR (400 MHz, DMSO-d6) Shift 9.80 (s, 1H), 8.00-8.09 (m, 1H), 7.89-7.98 (m, 3H), 7.79-7.89 (m, 2H), 7.70 (s, 1H), 7.60 (d, J=8.53 Hz, 2H). C13-HSQC (400 MHz, DMSO-d6) Shift (ppm) 40.15, 117.25, 126.08, 126.88, 129.22, 130.29, 134.25, 135.42.

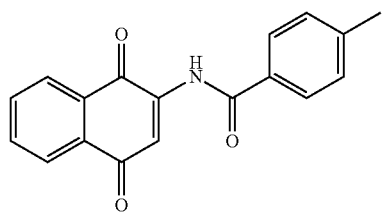 [SMILES: Cc1ccc(C(=O)NC2=CC(=O)c3ccccc3C2=O)cc1]

N-(1,4-dioxo-1,4-dihydronaphthalen-2-yl)-4-methyl-benzamide (3h)

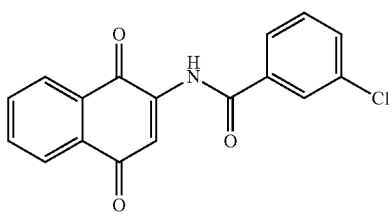

3-chloro-N-(1,4-dioxo-1,4-dihydronaphthalen-2-yl)benzamide (3j)

To a solution of Compound 1d (0.3 g, 1.7 mmol, 1 equiv) and NaH (0.2 g, 5 mmol, 60% dispersion) dissolved in tetrahydofuran (THF, 20 mL) was slowly added an excess of the corresponding isobutyryl chloride (267 uL, 2.5 mmol, 1.5 equiv). The reaction was stirred at room temperature for 10 minutes. The reaction was quenched with water and extracted with dichloromethane (2×), washed with 1 M NaOH, 1 M HCl, and saturated NaCl. The organic layer was dried over $Mg_2SO_4$ and concentrated in vacuo. Compound was purified using chromatography on silica gel eluting with ethyl acetate and hexane and crystallized with hot ethyl acetate and hexane to yield 103 mg mg yellow crystals (21% yield). MS m/z calcd (M+) 292.3, found 291.9. 1H NMR (400 MHz, DMSO-d6) Shift 9.65 (s, 1H), 8.08-8.16 (m, 1H), 7.99-8.07 (m, 1H), 7.85-7.99 (m, 4H), 7.77 (s, 1H), 7.42 (d, J=8.03 Hz, 2H), 2.42 (s, 3H). C13-HSQC (400 MHz, DMSO-d6) Shift (ppm) 21.56, 40.40, 129.90, 116.76, 128.16, 134.25, 135.51, 126.08, 126.73.

To a solution of Compound 1d (0.3 g, 1.7 mmol, 1 equiv) and NaH (0.2 g, 5 mmol, 60% dispersion) dissolved in tetrahydofuran (THF, 20 mL) was slowly added an excess of the corresponding 3-chlorobenzoyl chloride (326 uL, 2.5 mmol, 1.5 equiv). The reaction was stirred at room temperature for 5 minutes. The reaction was quenched with water and extracted with dichloromethane (2×), washed with 1 M NaOH, 1 M HCl, and saturated NaCl. The organic layer was dried over $Mg_2SO_4$ and concentrated in vacuo. Compound was purified using chromatography on silica gel eluting with ethyl acetate and hexane, followed by C18 silica gel, to yield 380 mg greenish yellow powder (72% yield). MS m/z calcd (M+) 312.72, found 312.7. 1H NMR (400 MHz, CHLOROFORM-d) Shift 9.18 (br. s., 1H), 8.18 (t, J=6.78 Hz, 1H), 8.04 (s, 1H), 7.96 (s, 1H), 7.75-7.89 (m, 2H), 7.63 (d, J=8.53 Hz, 1H), 7.46-7.56 (m, 1H), 7.29 (s, 3H). C13-HSQC (400 MHz, DMSO-d6) Shift (ppm) 40.08, 117.38, 126.02, 127.13, 127.13, 128.27, 131.08, 132.89, 134.31, 135.41.

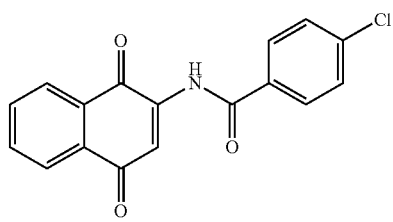 [SMILES: O=C(NC1=CC(=O)c2ccccc2C1=O)c1ccc(Cl)cc1]

4-chloro-N-(1,4-dioxo-1,4-dihydronaphthalen-2-yl)benzamide (3i)

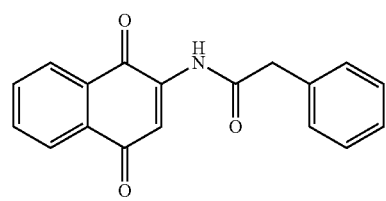 [SMILES: O=C(Cc1ccccc1)NC1=CC(=O)c2ccccc2C1=O]

N-(1,4-dioxo-1,4-dihydronaphthalen-2-yl)-2-phenylacetamide (3k)

To a solution of Compound 1d (0.3 g, 1.7 mmol, 1 equiv) and NaH (0.2 g, 5 mmol, 60% dispersion) dissolved in tetrahydofuran (THF, 20 mL) was slowly added an excess of the corresponding 4-chlorobenzoyl chloride (327 uL, 2.5 mmol, 1.5 equiv). The reaction was stirred at room temperature for 5 minutes. The reaction was quenched with water and extracted with dichloromethane (2×), washed with 1 M NaOH, 1 M HCl, and saturated NaCl. The organic layer was dried over $Mg_2SO_4$ and concentrated in vacuo. Com- To a solution of Compound 1d (0.5 g, 2.89 mmol, 1 equiv) and NaH (0.2 g, 5 mmol, 60% dispersion) dissolved in tetrahydofuran (THF, 20 mL) was slowly added an excess of the corresponding 2-phenacetyl chloride (573 uL, 4.34 mmol, 1.5 equiv). The reaction was stirred at room temperature for 1 hr. The reaction was quenched with water and extracted with dichloromethane (2×), washed with 1 M NaOH, 1 M HCl, and saturated NaCl. The organic layer was dried over $Mg_2SO_4$ and concentrated in vacuo. Compound was purified using chromatography on silica gel eluting with ethyl acetate and hexane to yield 33 m yellow powder (4% yield). MS m/z calcd (M+) 292.3, found 293.1. 1H NMR (400 MHz, CHLOROFORM-d) Shift 8.43 (br. s., 1H), 8.01-8.15 (m, 2H), 7.88 (s, 1H), 7.79 (dt, J=1.25, 7.53 Hz, 1H), 7.67-7.74 (m, 1H), 7.34-7.52 (m, 5H), 3.85 (s, 2H). C13-HSQC (400 MHz, DMSO-d6) Shift (ppm) 44.98, 76.87, 129.43, 128.10, 129.42, 133.16, 135.00, 117.16, 126.62, 126.62.

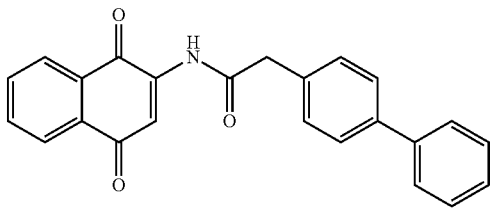 [SMILES: O=C(Cc1ccc(-c2ccccc2)cc1)NC1=CC(=O)c2ccccc2C1=O]

2-([1,1'-biphenyl]-4-yl)-N-(1,4-dioxo-1,4-dihydronaphthalen-2-yl)acetamide (3l)

To a solution of Compound 1d (0.3 g, 1.7 mmol, 1 equiv) and NaH (0.2 g, 5 mmol, 60% dispersion) dissolved in tetrahydofuran (THF, 20 mL) was slowly added an excess of the corresponding 3-chlorobenzoyl chloride (326 uL, 2.5 mmol, 1.5 equiv). Products were purified using chromatography followed by crystallization. The reaction was stirred at room temperature for 5 minutes. The reaction was quenched with water and extracted with dichloromethane (2×), washed with 1 M NaOH, 1 M HCl, and saturated NaCl. The organic layer was dried over Mg$_2$SO$_4$ and concentrated in vacuo. Compound was purified using chromatography on silica gel eluting with ethyl acetate and hexane, followed by C18 silica gel, to yield 380 mg greenish yellow powder (72% yield). MS m/z calcd (M+) 354.11, found 354.0. 1H NMR (400 MHz, DMSO-d6) d 9.79 (s, 1H), 8.24 (d, J=8.07 Hz, 2H), 8.00-8.15 (m, 2H), 7.87-7.99 (m, 3H), 7.70-7.84 (m, 3H), 7.41-7.61 (m, 4H). C13-HSQC (400 MHz, DMSO-d6) Shift (ppm) 39.59, 129.68, 117.02, 127.49, 134.24, 127.49, 135.47, 126.20, 128.82, 126.90, 131.36.

Synthesis of 2-ureyl Derivatives: Standard Procedure

Reactions were carried out under argon. To a stirred solution of Compound 1 (0.1 g, 0.577 mmol, 1 equiv) dissolved in dimethylformamide (DMF, 10 mL) was added the corresponding isocyanate (0.577 mmol, 1 equiv) followed by 3 drops of triethylamine. The reaction was then slowly heated to 80° C. and monitored using TLC. Upon completion, the reaction was allowed to cool to room temperature and quenched with water. Unless otherwise stated, the precipitated product was filtered and crystallized using hot ethyl acetate.

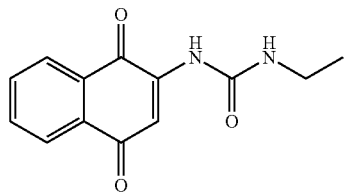 [SMILES: CCNC(=O)NC1=CC(=O)c2ccccc2C1=O]

1-(1,4-dioxo-1,4-dihydronaphthalen-2-yl)-3-ethylurea (4a)

To a stirred solution of Compound 1 (0.1 g, 0.577 mmol, 1 equiv) dissolved in dimethylformamide (DMF, 10 mL) was added ethyl isocyanate (100 μL, 0.577 mmol, 1 equiv) followed by 3 drops of triethylamine isocyanate. The reaction was heated to 80° C. and stirred for 3 hrs. After allowing the flask to cool to rt, the reaction was quenched with water and the filtered precipitate was crystallized with hot ethyl acetate to yield 92 mg fine dark yellow crystals (65% yield). MS m/z calcd (M+) 245.08, found 245.5. 1H NMR (400 MHz, DMSO-d6) Shift 8.90 (s, 1H), 8.04 (dd, J=0.88, 7.65 Hz, 1H), 7.96 (dd, J=0.88, 7.40 Hz, 1H), 7.76-7.91 (m, 2H), 7.50 (t, J=5.27 Hz, 1H), 7.47 (s, 1H), 3.07-3.22 (m, 2H), 1.07 (t, J=7.15 Hz, 3H). C13-HSQC (400 MHz, DMSO-d6) Shift (ppm) 15.42, 40.05, 34.51, 152.38, 146.65, 112.42, 133.77, 135.40, 125.57, 135.40, 133.62, 126.97.

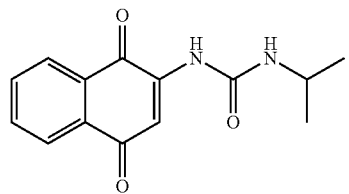 [SMILES: CC(C)NC(=O)NC1=CC(=O)c2ccccc2C1=O]

1-(1,4-dioxo-1,4-dihydronaphthalen-2-yl)-3-isopropylurea (4b)

To a stirred solution of Compound 1 (0.1 g, 0.577 mmol, 1 equiv) dissolved in dimethylformamide (DMF, 10 mL) was added isopropyl isocyanate (57 μL, 0.577 mmol, 1 equiv) followed by 3 drops of triethylamine isocyanate. The reaction was heated to 80° C. and stirred for 3 hrs. After allowing the flask to cool to rt, the reaction was quenched with water and the filtered precipitate was crystallized with hot ethyl acetate to give 40 mg crumbly tan crystals (27% yield). MS m/z calcd (M+) 259.1, found 259.0. 1H NMR (400 MHz, DMSO-d6) Shift 8.83 (s, 1H), 8.01-8.07 (m, 1H), 7.96 (dd, J=0.75, 7.53 Hz, 1H), 7.77-7.92 (m, 2H), 7.42-7.53 (m, 2H), 3.76 (qd, J=6.55, 13.24 Hz, 1H), 1.12 (d, J=6.53 Hz, 6H). C13-HSQC (400 MHz, DMSO-d6) Shift (ppm) 23.13, 40.08, 147.26, 152.18, 41.71, 112.04, 133.48, 135.31, 125.92, 126.92.

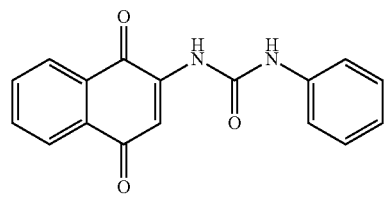 [SMILES: O=C(NC1=CC(=O)c2ccccc2C1=O)Nc1ccccc1]

1-(1,4-dioxo-1,4-dihydronaphthalen-2-yl)-3-phenylurea (4c)

To a stirred solution of Compound 1 (0.1 g, 0.577 mmol, 1 equiv) dissolved in dimethylformamide (DMF, 10 mL) was added phenyl isocyanate (63 uL, 0.577 mmol, 1 equiv) followed by 3 drops of triethylamine. The reaction was heated to 100° C. and stirred for 3 hrs. After allowing the flask to cool to rt, the reaction was quenched with water and extracted with DCM. The organic extract was concentrated in vacuo, and purified with HPLC. An M+ of 293 came off very slowly at 100% MeCN. The appropriate tubes were combined, and the product was crystallized from ethyl acetate to yield 27 mg powdery neon orange crystals (16% yield). MS m/z calcd (M+) 293.09, found 292.8. 1H NMR (400 MHz, DMSO-d6) Shift 9.88 (s, 1H), 9.19 (s, 1H), 8.09 (d, J=7.28 Hz, 1H), 7.99 (d, J=7.53 Hz, 1H), 7.81-7.95 (m, 2H), 7.52 (s, 1H), 7.49 (d, J=7.78 Hz, 2H), 7.34 (t, J=7.78 Hz, 2H), 7.02-7.11 (m, 1H). C13-HSQC (400 MHz, DMSO-d6) Shift 129.5, 135.3, 133.9, 123.4, 126.9, 126.0, 1289.5, 113.2, 119.0, 40.1.

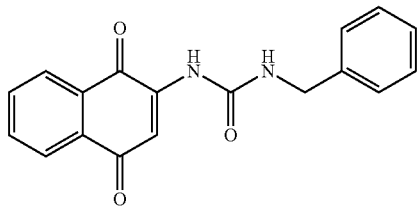 [SMILES: O=C(NCc1ccccc1)NC1=CC(=O)c2ccccc2C1=O]

1-benzyl-3-(1,4-dioxo-1,4-dihydronaphthalen-2-yl) urea (4d)

To a stirred solution of Compound 1 (0.1 g, 0.577 mmol, 1 equiv) dissolved in dimethylformamide (DMF, 10 mL) was added benzyl isocyanate (106 uL, 0.577 mmol, 1 equiv) followed by 3 drops of triethylamine. The reaction was then slowly heated to 80° C. and monitored using TLC. After 4 hrs, the reaction was allowed to cool to room temperature and quenched with water. The precipitated product was filtered and crystallized using hot ethyl acetate to yield 139 mg bright yellow crystals (78% yield). MS m/z calcd (M+) 307.1, found 307.0. 1H NMR (400 MHz, DMSO-d6) Shift 9.05 (s, 1H), 8.05 (dd, J=1.00, 7.53 Hz, 1H), 7.94-8.00 (m, 1H), 7.79-7.91 (m, 1H), 7.49 (s, 1H), 7.16-7.43 (m, 6H), 6.44 (t, J=5.90 Hz, 1H), 4.35 (d, J=5.77 Hz, 1H), 4.24 (d, J=6.02 Hz, 1H). C13-HSQC (400 MHz, DMSO-d6) Shift (ppm) 39.98, 43.07, 126.81, 128.99, 112.23, 133.55, 135.17, 125.72, 126.81.

Synthesis of Chromone Derivatives

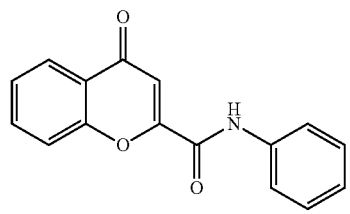 [SMILES: O=C(Nc1ccccc1)c1cc(=O)c2ccccc2o1]

4-oxo-N-phenyl-4H-chromene-2-carboxamide (5c)

4-oxo-4H-1-benzopyran-2-carboxylic acid (0.5 g, 2.63 mmol) was dissolved in 20 mL DMF and placed under argon. The solution was cooled to 0° C. and thionyl chloride was added slowly and the mixture stirred for 30 min on ice. After, aniline was added and the reaction was stirred at rt. overnight. The reaction was quenched with sodium bicarbonate solution, and the precipitate was filtered to yield 84 mg yellow powder (12% yield). MS m/z calcd (M+) 266.02, found 266.1. 1H NMR (400 MHz, DMSO-d6) Shift 10.77 (br. s., 1H), 8.09 (dd, J=1.38, 7.91 Hz, 1H), 7.90-7.99 (m, 1H), 7.83-7.88 (m, 1H), 7.78 (d, J=8.28 Hz, 2H), 7.57 (t, J=7.15 Hz, 1H), 7.41 (t, J=7.91 Hz, 2H), 7.17 (t, J=7.40 Hz, 1H), 6.99 (s, 1H). C13-HSQC (400 MHz, DMSO-d6) (ppm) 40.30, 111.46, 124.75, 129.20, 126.40, 121.85, 119.21, 135.51, 125.28.

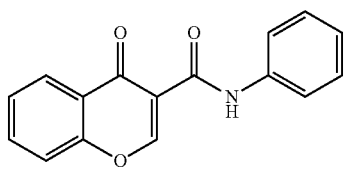 [SMILES: O=C(Nc1ccccc1)c1coc2ccccc2c1=O]

4-oxo-N-phenyl-4H-chromene-3-carboxamide (5d)

Chromone-3-carboxylic acid (0.5 g, 2.63 mmol) was dissolved in DCM and placed under argon. The solution was cooled to 0° C. and thionyl chloride was added slowly and the mixture stirred for 30 min on ice. After, aniline was added and the reaction was stirred at rt. overnight. Reaction quenched with 1 M NaHCO₃ and filtered the white precipitate. Washed with 1 M NaOH (×2), 1 M HCl, and saturated NaCl. The organic layer was dried with Mg₂SO₄, filtered, and concentrated in vacuo. The resulting powder was crystallized with ethyl acetate to yield 38 mg of fine, very pale yellow crystals (5% yield). MS m/z calcd (M+) 265.07, found 266.2. 1H NMR (400 MHz, DMSO-d6) Shift 11.34 (s, 1H), 9.21 (s, 1H), 8.27 (dd, J=1.51, 8.03 Hz, 1H), 7.91-8.01 (m, 1H), 7.85 (d, J=8.28 Hz, 1H), 7.74 (d, J=7.78 Hz, 2H), 7.61-7.70 (m, 1H), 7.41 (t, J=7.91 Hz, 2H), 7.12-7.20 (m, 1H). C13-HSQC (400 MHz, DMSO-d6) Shift 39.91, 125.82, 129.97, 127.10, 118.84, 118.83, 136.01, 125.83, 127.1.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

References

U.S. Pat. No. 5,399,363
U.S. Pat. No. 5,466,468

U.S. Pat. No. 5,543,158
U.S. Pat. No. 5,580,579
U.S. Pat. No. 5,629,001
U.S. Pat. No. 5,641,515
U.S. Pat. No. 5,725,871
U.S. Pat. No. 5,756,353
U.S. Pat. No. 5,780,045
U.S. Pat. No. 5,792,451
U.S. Pat. No. 5,804,212
U.S. Pat. No. 6,613,308
U.S. Pat. No. 6,7537,514

Afrikanova T, Serruys A S, Buenafe O E, Clinckers R, Smolders I, de Witte P A, Crawford A D, Esguerra C V (2013) Validation of the zebrafish pentylenetetrazol seizure model: locomotor versus electrographic responses to antiepileptic drugs. PLoS ONE 8:e54166.

Albrecht, P.; Lewerenz, J.; Dittmer, S.; Noack, R.; Maher, P.; Methner, A. Mechanisms of oxidative glutamate toxicity: the glutamate/cystine antiporter system xc- as a neuroprotective drug target. CNS Neurol Disord Drug Targets 2010, 9, 373-82.

Allen, J. A.; Shankara, T.; Janus, P.; Buck, S.; Diemer, T.; Hales, K. H.; Hales, D. B. Energized, polarized, and actively respiring mitochondria are required for acute Leydig cell steroidogenesis. Endocrinology 2006, 147, 3924-35.

Allison, A. C. The possible role of vitamin K deficiency in the pathogenesis of Alzheimer's disease and in augmenting brain damage associated with cardiovascular disease. Med Hypotheses 2001, 57, 151-5.

Alsdorf, R.; Wyszynski, D. F. Teratogenicity of sodium valproate. Expert Opin Drug Saf 2005, 4, 345-53.

Anderson, N. G., Practical Process Research & Development—A Guide For Organic Chemists, 2nd ed., Academic Press, New York, 2012.

Baraban S C, Dinday M T, Castro P A, Chege S, Guyenet S, Taylor M R (2007) A large-scale mutagenesis screen to identify seizure-resistant zebrafish. Epilepsia 48:1151-1157.

Baraban, S. C. Emerging epilepsy models: insights from mice, flies, worms and fish. Curr Opin Neurol 2007, 20, 164-8.

Baraban, S. C.; Taylor, M. R.; Castro, P. A.; Baier, H. Pentylenetetrazole induced changes in zebrafish behavior, neural activity and c-fos expression. Neuroscience 2005, 131, 759-68.

Barrionuevo, W. R.; Burggren, W. W. O2 consumption and heart rate in developing zebrafish (Danio rerio): influence of temperature and ambient O2. Am J Physiol 1999, 276, R505-13.

Barton M E, Klein B D, Wolf H H, White H S (2001) Pharmacological characterization of the 6 Hz psychomotor seizure model of partial epilepsy. Epilepsy Res 47:217-227.

Baxendale S, Holdsworth C J, Meza Santoscoy P L, Harrison M R, Fox J, Parkin C A, Ingham P W, Cunliffe V T (2012) Identification of compounds with anti-convulsant properties in a zebrafish model of eplieptic seizures. Dis Model Mech 5:773-784.

Beckman, K. B.; Ames, B. N. The free radical theory of aging matures. Physiol Rev 1998, 78, 547-81.

Beeson C C, Beeson G C, Schnellmann R G (2010) A high-throughput respirometric assay for mitochondrial biogenesis and toxicity. Anal Biochem 404:75-81.

Berghmans S, Hunt J, Roach A, Goldsmith P (2007) Zebrafish offer the potential for a primary screen to identify a wide variety of potential anticonvulsants. Epilepsy Res 75:18-28.

Bialer M, White H S (2010) Key factors in the discovery and development of new antiepileptic drugs. Nat Rev Drug Discov 9:68-82.

Bindoff L A, Engelsen B A (2011) Mitochondrial cytopathies. In: The Causes of Epilepsy (Shorvon, S. D. et al., eds), pp 147-157: Cambridge University Press.

Blois, M. S. Antioxidant Determinations by the Use of a Stable Free Radical. Nature 1958, 181, 1199-1200.

Bossy-Wetzel, E.; Barsoum, M. J.; Godzik, A.; Schwarzenbacher, R.; Lipton, S. A. Mitochondrial fission in apoptosis, neurodegeneration and aging. Curr Opin Cell Biol 2003, 15, 706-16.

Bradner J E, West N, Grachan M L, Greenberg E F, Haggarty S J, Warnow T, Mazitschek R (2010) Chemical phylogenetics of histone deacetylases. Nat Chem Biol 6:238-243.

Breckenridge, D. G.; Kang, B. H.; Kokel, D.; Mitani, S.; Staehelin, L. A.; Xue, D. Caenorhabditis elegans drp-1 and fis-2 regulate distinct cell-death execution pathways downstream of ced-3 and independent of ced-9. Mol Cell 2008, 31, 586-97.

Butler K V, Kalin J, Brochier C, Vistoli G, Langley B, Kozikowski A P (2010) Rational design and simple chemistry yield a superior, neuroprotective HDAC6 inhibitor, tubastatin A. Journal of the American Chemical Society 132:10842-10846.

Canafoglia, L.; Franceschetti, S.; Antozzi, C.; Carrara, F.; Farina, L.; Granata, T.; Lamantea, E.; Savoiardo, M.; Uziel, G.; Villani, F.; Zeviani, M.; Avanzini, G. Epileptic phenotypes associated with mitochondrial disorders. Neurology 2001, 56, 1340-6.

Chaix, Y.; Ferraro, T. N.; Lapouble, E.; Martin, B. Chemoconvulsant-induced seizure susceptibility: toward a common genetic basis? Epilepsia 2007, 48 Suppl 5, 48-52.

Chan, S. S. L.; Longley, M. J.; Copeland, W. C. Modulation of the W748S mutation in DNA polymerase {gamma} by the E1143G polymorphism in mitochondrial disorders. Hum Mol Genet 2006, 15, 3473-3483.

Chang, C. R.; Blackstone, C. Cyclic AMP-dependent protein kinase phosphorylation of Drp1 regulates its GTPase activity and mitochondrial morphology. J Biol Chem 2007, 282, 21583-7.

Cory, A. H.; Owen, T. C.; Barltrop, J. A.; Cory, J. G. Use of an aqueous soluble tetrazolium/formazan assay for cell growth assays in culture. Cancer Commun 1991, 3, 207-12.

Davis, J. B.; Maher, P. Protein kinase C activation inhibits glutamate-induced cytotoxicity in a neuronal cell line. Brain Res 1994, 652, 169-73.

Degterev, A.; Huang, Z.; Boyce, M.; Li, Y.; Jagtap, P.; Mizushima, N.; Cuny, G. D.; Mitchison, T. J.; Moskowitz, M. A.; Yuan, J. Chemical inhibitor of nonapoptotic cell death with therapeutic potential for ischemic brain injury. Nat Chem Biol 2005, 1, 112-9.

Duncan, J. S. The promise of new antiepileptic drugs. Br J Clin Pharmacol 2002, 53, 123-31.

Fass D M, Shah R, Ghosh B, Hennig K, Norton S, Zhao W N, Reis S A, Klein P S, Mazitschek R, Maglathlin R L, Lewis T A, Haggarty S J (2010) Effect of Inhibiting Histone Deacetylase with Short-Chain Carboxylic Acids and Their Hydroxamic Acid Analogs on Vertebrate Development and Neuronal Chromatin. ACS medicinal chemistry letters 2:39-42.

Fieser, L. F. a. H., J. L. Reaction of hydrazoic acid with naphthoquinones. *Journal of the American Chemical Society* 1935, 57, 1482-1484.

Finsterer, J.; Segall, L. Drugs interfering with mitochondrial disorders. *Drug Chem Toxicol* 2010, 33, 138-51.

Folbergrova, J.; Kunz, W. S. Mitochondrial dysfunction in epilepsy. *Mitochondrion* 2011.

Frank, S.; Gaume, B.; Bergmann-Leitner, E. S.; Leitner, W. W.; Robert, E. G.; Catez, F.; Smith, C. L.; Youle, R. J. The role of dynamin-related protein 1, a mediator of mitochondrial fission, in apoptosis. *Dev Cell* 2001, 1, 515-25.

Fukui, M.; Song, J. H.; Choi, J.; Choi, H. J.; Zhu, B. T. Mechanism of glutamate-induced neurotoxicity in HT22 mouse hippocampal cells. *Eur J Pharmacol* 2009, 617, 1-11.

Furian A F, Fighera M R, Oliveira M S, Ferreira A P, Fiorenza N G, de Carvalho Myskiw J, Petry J C, Coelho R C, Mello C F, Royes L F (2007) Methylene blue prevents methylmalonate-induced seizures and oxidative damage in rat striatum. Neurochemistry international 50:164-171.

Gohil V M, Nilsson R, Belcher-Timme C A, Luo B, Root D E, Mootha V K (2010) Nutrient-sensitized screening for drugs that shift energy metabolism from mitochondrial respiration to glycolysis. Nature Biotechnology 28:249-255.

Gravemann, U.; Volland, J.; Nau, H. Hydroxamic acid and fluorinated derivatives of valproic acid: anticonvulsant activity, neurotoxicity and teratogenicity. *Neurotoxicol Teratol* 2008, 30, 390-4.

Grohm, J.; Kim, S. W.; Mamrak, U.; Tobaben, S.; Cassidy-Stone, A.; Nunnari, J.; Plesnila, N.; Culmsee, C. Inhibition of Drp1 provides neuroprotection in vitro and in vivo. *Cell Death Differ* 2012.

Halliwell, B. Role of free radicals in the neurodegenerative diseases: therapeutic implications for antioxidant treatment. *Drugs Aging* 2001, 18, 685-716.

*Handbook of Pharmaceutical Salts: Properties, and Use*, Stahl and Wermuth Eds.), Verlag Helvetica Chimica Acta, 2002.

Hansen S L, Sperling B B, Sanchez C (2004) Anticonvulsant and antiepileptogenic effects of GABAA receptor ligands in pentylenetetrazole-kindled mice. Progress in neuro-psychopharmacology & biological psychiatry 28:105-113.

Hoffmann K, Czapp M, Loscher W (2008) Increase in antiepileptic efficacy during prolonged treatment with valproic acid: role of inhibition of histone deacetylases? Epilepsy Res 81:107-113.

Hortopan G A, Dinday M T, Baraban S C (2010) Spontaneous seizures and altered gene expression in GABA signaling pathways in a mind bomb mutant zebrafish. J Neurosci 30:13718-13728.

Hortopan G A, Dinday M T, Baraban S C (2010) Zebrafish as a model for studying genetic aspects of epilepsy. Dis Model Mech 3:144-148.

Hwang et al., *Crit. Rev. Ther. Drug Carrier Syst.*, 15(3): 243-284, 1998.

Inks, E. S.; Josey, B. J.; Jesinkey, S. R.; Chou, C. J. A novel class of small molecule inhibitors of HDAC6. *ACS Chem Biol* 2012, 7, 331-9.

Jagasia, R.; Grote, P.; Westermann, B.; Conradt, B. DRP-1-mediated mitochondrial fragmentation during EGL-1-induced cell death in C. elegans. *Nature* 2005, 433, 754-60.

Johannessen C U, Johannessen S I (2003) Valproate: past, present, and future. CNS drug reviews 9:199-216.

Josey B J, Inks E S, Wen X, Chou C J (2013) Structure-activity relationship study of Vitamin K derivatives yields highly potent neuroprotective agents. Journal of medicinal chemistry 56:1007-1022.

Kimmel, C. B.; Ballard, W. W.; Kimmel, S. R.; Ullmann, B.; Schilling, T. F. Stages of embryonic development of the zebrafish. *Dev Dyn* 1995, 203, 253-310.

Kokel D, Bryan J, Laggner C, White R, Cheung C Y, Mateus R, Healey D, Kim S, Werdich A A, Haggarty S J, Macrae C A, Shoichet B, Peterson R T (2010) Rapid behavior-based identification of neuroactive small molecules in the zebrafish. Nat Chem Biol.

Kroemer, G.; Reed, J. C. Mitochondrial control of cell death. *Nat Med* 2000, 6, 513-9.

Lee, Y. J.; Jeong, S. Y.; Karbowski, M.; Smith, C. L.; Youle, R. J. Roles of the mammalian mitochondrial fission and fusion mediators Fis1, Drp1, and Opa1 in apoptosis. *Mol Biol Cell* 2004, 15, 5001-11.

Lemasters, J. J.; Nieminen, A. L. Mitochondrial oxygen radical formation during reductive and oxidative stress to intact hepatocytes. *Biosci Rep* 1997, 17, 281-91.

Lheureux, P. E.; Hantson, P. Carnitine in the treatment of valproic acid-induced toxicity. *Clin Toxicol (Phila)* 2009, 47, 101-11.

Li, J.; Lin, J. C.; Wang, H.; Peterson, J. W.; Furie, B. C.; Furie, B.; Booth, S. L.; Volpe, J. J.; Rosenberg, P. A. Novel role of vitamin kin preventing oxidative injury to developing oligodendrocytes and neurons. *J Neurosci* 2003, 23, 5816-26.

Lifshitz, J.; Friberg, H.; Neumar, R. W.; Raghupathi, R.; Welsh, F. A.; Janmey, P.; Saatman, K. E.; Wieloch, T.; Grady, M. S.; McIntosh, T. K. Structural and functional damage sustained by mitochondria after traumatic brain injury in the rat: evidence for differentially sensitive populations in the cortex and hippocampus. *J Cereb Blood Flow Metab* 2003, 23, 219-31.

Lin, M. T.; Beal, M. F. Mitochondrial dysfunction and oxidative stress in neurodegenerative diseases. *Nature* 2006, 443, 787-95.

Livak K J, Schmittgen T D (2001) Analysis of relative gene expression data using real-time quantitative PCR and the 2-ddCt method. Methods 25:402-408.

Loscher W, Schmidt D (2011) Modern antiepileptic drug development has failed to deliver: ways out of the current dilemma. Epilepsia 52:657-678.

Maher, P.; Davis, J. B. The role of monoamine metabolism in oxidative glutamate toxicity. *Journal of Neuroscience* 1996, 16, 6394-401.

Mahmood F, Mozere M, Zdebik A A, Stanescu H C, Tobin J, Beales P L, Kleta R, Bockenhauer D, Russell C (2013) Generation and validation of a zebrafish model of EAST (epilepsy, ataxia, sensorineural deafness and tubulopathy) syndrome. Disease Models and Mechanisms 6.

*March's Advanced Organic Chemistry*: Reactions, Mechanisms, and Structure, 2007.

Mathiowitz et al., *Nature,* 386(6623):410-414, 1997.

Matsumoto, K.; Lo, E. H.; Pierce, A. R.; Halpern, E. F.; Newcomb, R. Secondary elevation of extracellular neurotransmitter amino acids in the reperfusion phase following focal cerebral ischemia. *J Cereb Blood Flow Metab* 1996, 16, 114-24.

Molyneux, P. The use of the stable free radical diphenylpi-crylhydrazyl (DPPH) for estimating antioxidant activity. *Songklanakarin J Sci. Technol.* 2003, 26.

Morimoto, B. H.; Koshland, D. E., Jr. Induction and expression of long- and short-term neurosecretory potentiation in a neural cell line. *Neuron* 1990, 5, 875-80.

Mugoni V, Postel R, Catanzaro V, De Luca E, Turco E, Digilio G, Silengo L, Murphy M P, Medana C, Stainier D Y, Bakkers J, Santoro M M (2013) Ubiad1 is an antioxidant enzyme that regulates eNOS activity by CoQ10 synthesis. Cell 152:504-518.

Murphy, T. H.; Miyamoto, M.; Sastre, A.; Schnaar, R. L.; Coyle, J. T. Glutamate toxicity in a neuronal cell line involves inhibition of cystine transport leading to oxidative stress. Neuron 1989, 2, 1547-58.

Nagai, S. 2-(Ureido or alkoxycarbonylamino)-1,4-naphthoquinones as agricultural fungicides. Jpn. Kokai Tokkyo Koho 1979.

Nguyen, T.; Nioi, P.; Pickett, C. B. The Nrf2-antioxidant response element signaling pathway and its activation by oxidative stress. J Biol Chem 2009, 284, 13291-5.

Orellana-Paucar A M, Serruys A S, Afrikanova T, Maes J, De Borggraeve W, Alen J, Leon-Tamariz F, Wilches-Arizabala I M, Crawford A D, de Witte P A, Esguerra C V (2012) Anticonvulsant activity of bisabolene sesquiterpenoids of Curcuma longa in zebrafish and mouse seizure models. Epilepsy & behavior: E&B 24:14-22.

Patel M N (2002) Oxidative stress, mitochondrial dysfunction, and epilepsy. Free radical research 36:1139-1146.

Pelgrims J, De Vos F, Van den Brande J, Schrijvers D, Prove A, Vermorken J B (2000) Methylene blue in the treatment and prevention of ifosfamide-induced encephalopathy: report of 12 cases and a review of the literature. British journal of cancer 82:291-294.

Perucca, E. Pharmacological and therapeutic properties of valproate: a summary after 35 years of clinical experience. CNS Drugs 2002, 16, 695-714.

Peterson R T, Fishman M C (2011) Designing zebrafish chemical screens. Methods in cell biology 105:525-541.

Phiel C J, Zhang F, Huang E Y, Guenther M G, Lazar M A, Klein P S (2001) Histone deacetylase is a direct target of valproic acid, a potent anticonvulsant, mood stabilizer, and teratogen. J Biol Chem 276:36734-36741.

Price, P. A. Role of vitamin-K-dependent proteins in bone metabolism. Annu Rev Nutr 1988, 8, 565-83.

Racine R J (1972) Modification of seizure activity by electrical stimulation. II. Motor seizure. Electroencephalogr Clin Neurophysiol 32:281-94.

Reichard, J. F.; Motz, G. T.; Puga, A. Heme oxygenase-1 induction by NRF2 requires inactivation of the transcriptional repressor BACH1. Nucleic Acids Res 2007, 35, 7074-86.

Remington: The Science and Practice of Pharmacy, 21$^{st}$ Ed. Lippincott Williams and Wilkins, 2005

Remington's Pharmaceutical Sciences, 15th Edition, pages 1035-1038 and 1570-1580

Remington's Pharmaceutical Sciences, 18th Ed. Mack Printing Company, 1990.

Riederer, P.; Sofic, E.; Rausch, W. D.; Schmidt, B.; Reynolds, G. P.; Jellinger, K.; Youdim, M. B. Transition metals, ferritin, glutathione, and ascorbic acid in parkinsonian brains. J Neurochem 1989, 52, 515-20.

Rogawski M A, Loscher W (2004) The neurobiology of antiepileptic drugs. Nature reviews Neuroscience 5:553-564.

Sagara, Y.; Schubert, D. The activation of metabotropic glutamate receptors protects nerve cells from oxidative stress. J Neurosci 1998, 18, 6662-71.

Sakaue, M.; Mori, N.; Okazaki, M.; Kadowaki, E.; Kaneko, T.; Hemmi, N.; Sekiguchi, H.; Maki, T.; Ozawa, A.; Hara, S.; Arishima, K.; Yamamoto, M. Vitamin K has the potential to protect neurons from methylmercury-induced cell death in vitro. J Neurosci Res 2011, 89, 1052-8.

Saneto, R. P.; Lee, I. C.; Koenig, M. K.; Bao, X.; Weng, S. W.; Naviaux, R. K.; Wong, L. J. POLG DNA testing as an emerging standard of care before instituting valproic acid therapy for pediatric seizure disorders. Seizure 2010, 19, 140-6.

Shearer, M. J.; Bach, A.; Kohlmeier, M. Chemistry, nutritional sources, tissue distribution and metabolism of vitamin K with special reference to bone health. J Nutr 1996, 126, 1181S-6S.

Shneyvays V, Leshem D, Shmist Y, Zinman T, Shainberg A (2005) Effects of menadione and its derivative on cultured cardiomyocytes with mitochondrial disorders. Journal of molecular and cellular cardiology 39:149-158.

Silva, M. F.; Aires, C. C.; Luis, P. B.; Ruiter, J. P.; Ijlst, L.; Duran, M.; Wanders, R. J.; Tavares de Almeida, I. Valproic acid metabolism and its effects on mitochondrial fatty acid oxidation: A review. J Inherit Metab Dis 2008.

Simonian, N. A.; Coyle, J. T. Oxidative stress in neurodegenerative diseases. Annu Rev Pharmacol Toxicol 1996, 36, 83-106.

Sims, N. R.; Muyderman, H. Mitochondria, oxidative metabolism and cell death in stroke. Biochim Biophys Acta 2010, 1802, 80-91.

Smimova, E.; Griparic, L.; Shurland, D. L.; van der Bliek, A. M. Dynamin-related protein Drp1 is required for mitochondrial division in mammalian cells. Mol Biol Cell 2001, 12, 2245-56.

Sofic, E.; Lange, K. W.; Jellinger, K.; Riederer, P. Reduced and oxidized glutathione in the substantia nigra of patients with Parkinson's disease. Neurosci Lett 1992, 142, 128-30.

Stables J P, Kupferberg H J (1997) The NIH anticonvulsant drug development (ADD) program: preclinical anticonvulsant screening project. In: Molecular and cellular targets for anti-epileptic drugs (Avanzini, G. et al., eds), pp 191-198 London, England: John Libbey & Company Ltd.

Stewart A M, Desmond D, Kyzar E, Gaikwad S, Roth A, Riehl R, Collins C, Monnig L, Green J, Kalueff A V. (2012) Perspectives of zebrafish models of epilepsy: what, how and where next? Brain Res Bull 87:135-143.

Stewart, J. D.; Horvath, R.; Baruffini, E.; Ferrero, I.; Bulst, S.; Watkins, P. B.; Fontana, R. J.; Day, C. P.; Chinnery, P. F. Polymerase gamma gene POLG determines the risk of sodium valproate-induced liver toxicity. Hepatology 2010, 52, 1791-6.

Sundaram, K. S.; Lev, M. Regulation of sulfotransferase activity by vitamin K in mouse brain. Arch Biochem Biophys 1990, 277, 109-13.

Suttie, J. W. Mechanism of action of vitamin K: synthesis of gamma-carboxyglutamic acid. CRC Crit Rev Biochem 1980, 8, 191-223.

Takenaga et al., J. Control Release, 52(1-2):81-87, 1998.

Tan, S.; Schubert, D.; Maher, P. Oxytosis: A novel form of programmed cell death. Curr Top Med Chem 2001, 1, 497-506.

Tandon, V. K.; Singh, R. V.; Yadav, D. B. Synthesis and evaluation of novel 1,4-naphthoquinone derivatives as antiviral, antifungal and anticancer agents. Bioorg Med Chem Lett 2004, 14, 2901-4.

Ten, V. S.; Starkov, A. Hypoxic-ischemic injury in the developing brain: the role of reactive oxygen species originating in mitochondria. Neurol Res Int 2012, 2012, 542976.

Tessier P, Smil D V, Wahhab A, Leit S, Rahil J, Li Z, Deziel R, Besterman J M (2009) Diphenylmethylene hydroxamic acids as selective class IIa histone deacetylase inhibitors. Bioorganic & medicinal chemistry letters 19:5684-5688.

Thijssen, H. H.; Drittij-Reijnders, M. J. Vitamin K status in human tissues: tissue-specific accumulation of phylloquinone and menaquinone-4. *Br J Nutr* 1996, 75, 121-7.

Topliss, J. G. Utilization of operational schemes for analog synthesis in drug design. *J Med Chem* 1972, 15, 1006-11.

Tsaioun, K. I. Vitamin K-dependent proteins in the developing and aging nervous system. *Nutr Rev* 1999, 57, 231-40.

Turnbull, D. M.; Bone, A. J.; Bartlett, K.; Koundakjian, P. P.; Sherratt, H. S. The effects of valproate on intermediary metabolism in isolated rat hepatocytes and intact rats. *Biochem Pharmacol* 1983, 32, 1887-92.

Valente, C.; Moreira, R.; Guedes, R. C.; Iley, J.; Jaffar, M.; Douglas, K. T. The 1,4-naphthoquinone scaffold in the design of cysteine protease inhibitors. *Bioorg Med Chem* 2007, 15, 5340-50.

Vos, M.; Esposito, G.; Edirisinghe, J. N.; Vilain, S.; Haddad, D. M.; Slabbaert, J. R.; Van Meensel, S.; Schaap, O.; De Stroop, B.; Meganathan, R.; Morais, V. A.; Verstreken, P. Vitamin K2 is a mitochondrial electron carrier that rescues pink1 deficiency. *Science* 2012, 336, 1306-10.

Waldbaum S, Patel M (2010) Mitochondrial dysfunction and oxidative stress: a contributing link to acquired epilepsy? J Bioenerg Biomembr 42:449-455.

Waldbaum, S.; Patel, M. Mitochondria, oxidative stress, and temporal lobe epilepsy. *Epilepsy Res* 2010, 88, 23-45.

Wang, Z.; Jiang, H.; Chen, S.; Du, F.; Wang, X. The mitochondrial phosphatase PGAM5 functions at the convergence point of multiple necrotic death pathways. *Cell* 2012, 148, 228-43.

Wen Y, Wenjun L, Poteet E C, Xie L, Tan C, Yan L, Ju X, Liu R, Qian H, Marvin M A, Goldberg M S, She H, Mao Z, Simpkins J W, Yan S (2011) Alternative mitochondrial electron transfer as a novel strategy for neuroprotection. J Biol Chem 286:16504-16515.

Westerfield, M. *The zebrafish book. A guide for the laboratory use of zebrafish (Danio rerio)*. 4th ed.; University of Oregon Press: Eugene, 2000.

White H S, Johnson M, Wolf H H, Kupferberg H J (1995) The early identification of anticonvulsant activity: role of the maximal electroshock and subcutaneous pentylenetetrazol seizure models. Italian journal of neurological sciences 16:73-77.

Zon, L. I.; Peterson, R. T. In vivo drug discovery in the zebrafish. *Nat Rev Drug Discov* 2005, 4, 35-44.

Zon, L. I.; Peterson, R. The new age of chemical screening in zebrafish. *Zebrafish* 2010, 7, 1.

---

What is claimed is:

1. A pharmaceutical preparation comprising a compound of the formula:

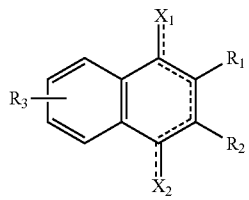

wherein $X_1$ and $X_2$ are each =O;
wherein $R_3$ is —H or halogen;
wherein $R_2$ is —H or $C_{1-6}$ alkyl;
wherein $R_1$ is

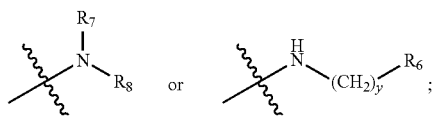

wherein y is 1-3;
wherein $R_7$ is —H or $C_{1-3}$ alkyl;
wherein $R_6$ is $C_{1-12}$ alkyl, $C_{2-10}$ alkynyl, or $C_{2-10}$ alkenyl;
wherein $R_8$ is $C_{1-12}$ alkyl $C_{2-10}$ alkenyl, or $C_{2-10}$ alkynyl or a pharmaceutically acceptable salt thereof; and an excipient.

2. The pharmaceutical preparation of claim 1, wherein the pharmaceutical preparation is formulated for oral delivery.

3. The pharmaceutical preparation of claim 2, wherein the pharmaceutical preparation comprises a tablet, capsule, or powder.

4. The pharmaceutical preparation of claim 1, wherein the pharmaceutical preparation is formulated for intravenous, peritoneal, subcutaneous, intrathecal, intracerebral, intraspinal, intrathecal, nasal, inhalational, sublingual, intramuscular, or per os delivery.

5. The pharmaceutical preparation of claim 1, wherein the compound is comprised in a liposome, unilamellar liposome, multilamellar liposome, multivesicular liposome, nanoparticle, emulsion, or lipid formulation.

6. The pharmaceutical preparation of claim 1, wherein $R_3$ is —H.

7. The pharmaceutical preparation of claim 1, wherein $R_2$ is —H.

8. The pharmaceutical preparation of claim 1, wherein $R_3$ is —H and $R_2$ is —H.

9. The pharmaceutical preparation of claim 8, wherein $R_1$ is

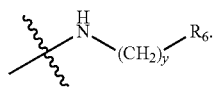

10. The pharmaceutical preparation of claim 9, wherein y=1.

11. The pharmaceutical preparation of claim 10, wherein $R_1$ is

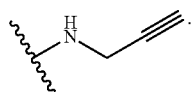

12. The pharmaceutical preparation of claim 1, wherein $R_1$ is

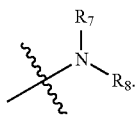

13. The pharmaceutical preparation of claim 12, wherein $R_7$ is H.

14. The pharmaceutical preparation of claim 13, wherein $R_8$ is $C_{2-10}$ alkenyl or $C_{2-10}$ alkynyl.

15. The pharmaceutical preparation of claim 1, wherein the compound is

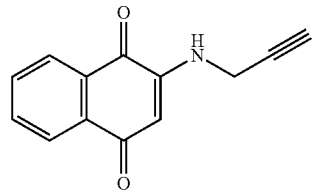 [SMILES: C#CCNC1=CC(=O)c2ccccc2C1=O]

or a salt thereof.

16. The pharmaceutical preparation of claim 9, wherein $R_6$ is $C_{2-10}$ alkenyl.

17. The pharmaceutical preparation of claim 16, wherein $R_6$ is heteroatom-unsubstituted $C_{2-10}$ alkenyl.

18. The pharmaceutical preparation of claim 17, wherein $R_6$ is heteroatom-unsubstituted $C_{10}$ alkenyl.

19. The pharmaceutical preparation of claim 9, wherein $R_6$ is $C_{2-10}$ alkynyl.

20. The pharmaceutical preparation of claim 19, wherein $R_6$ is heteroatom-substituted $C_{2-10}$ alkynyl.

21. The pharmaceutical preparation of claim 19, wherein $R_6$ is heteroatom-unsubstituted $C_{2-10}$ alkynyl.

22. The pharmaceutical preparation of claim 21, wherein $R_6$ is —C≡CH, —C≡CCH$_3$, or —C≡CC$_6$H$_5$.

23. The pharmaceutical preparation of claim 22, wherein $R_6$ is —C≡CCH$_3$.

24. The pharmaceutical preparation of claim 9, wherein y=2 and wherein $R_6$ is $C_{2-10}$ alkynyl.

25. The pharmaceutical preparation of claim 24, wherein $R_6$ is heteroatom-unsubstituted $C_{2-10}$ alkynyl.

26. The pharmaceutical preparation of claim 1, wherein the compound is

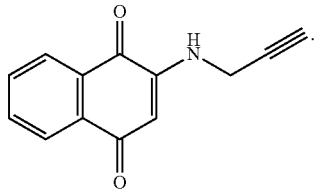 [SMILES: C#CCNC1=CC(=O)c2ccccc2C1=O]

* * * * *